(12) United States Patent
Mazur

(10) Patent No.: US 12,195,797 B2
(45) Date of Patent: *Jan. 14, 2025

(54) SYSTEMS AND METHODS FOR SEQUENCING ERROR CORRECTION VIA DOUBLE STRAND PRESERVATION

(71) Applicant: Ultima Genomics, Inc., Fremont, CA (US)

(72) Inventor: Daniel Mazur, San Diego, CA (US)

(73) Assignee: Ultima Genomics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/737,230

(22) Filed: Jun. 7, 2024

(65) Prior Publication Data

US 2024/0360501 A1     Oct. 31, 2024

Related U.S. Application Data

(63) Continuation of application No. 18/435,829, filed on Feb. 7, 2024, which is a continuation of application No. PCT/US2022/040935, filed on Aug. 19, 2022.

(Continued)

(51) Int. Cl.
    *C12Q 1/68*      (2018.01)
    *C12Q 1/6844*    (2018.01)
    *C12Q 1/6869*    (2018.01)

(52) U.S. Cl.
    CPC ......... *C12Q 1/6869* (2013.01); *C12Q 1/6844* (2013.01)

(58) Field of Classification Search
    CPC .................................................. C12Q 1/6869
    See application file for complete search history.

(56) References Cited

U.S. PATENT DOCUMENTS 5,409,811 A     4/1995  Tabor et al.
5,641,658 A     6/1997  Adams et al.
                (Continued)

FOREIGN PATENT DOCUMENTS

WO     WO-2021155371 A1     8/2021
WO     WO-2022040557 A2     2/2022
                (Continued)

OTHER PUBLICATIONS

Adessi, et al. Solid phase DNA amplification: characterisation of primer attachment and amplification mechanisms. Nucleic Acids Res. 2000, 28(20):E87:1-8.

(Continued)

*Primary Examiner* — Kenneth R Horlick
(74) *Attorney, Agent, or Firm* — Wilson Sonsini Goodrich & Rosati

(57) ABSTRACT

The present disclosure provides compositions, methods, and systems for preparing nucleic acid samples for sequencing, including attaching adapters to a template nucleic acid molecule having a first and second strands; attaching the template nucleic acid molecule to a support; detaching the first and second strands from each other; generating a reverse complement copy of the second strand using a primer coupled to the support; generating amplified copies of the first strand and the reverse complement copy of the second strand using primers coupled to the support; and identifying the sequences of the first strand and the reverse complement copy of the second strand. Further provided herein are methods of error correction by preserving both strands of a template nucleic acid molecule during amplification.

20 Claims, 37 Drawing Sheets

Specification includes a Sequence Listing.

Related U.S. Application Data

(60) Provisional application No. 63/235,451, filed on Aug. 20, 2021.

(56) References Cited

U.S. PATENT DOCUMENTS

| | | | |
|---|---|---|---|
| 5,674,716 | A | 10/1997 | Tabor et al. |
| 10,900,078 | B2 | 1/2021 | Almogy et al. |
| 11,447,818 | B2 | 9/2022 | Zhao et al. |
| 2006/0134633 | A1* | 6/2006 | Chen .................. G01N 21/253 435/6.11 |
| 2021/0079464 | A1 | 3/2021 | Beckett et al. |
| 2022/0042072 | A1 | 2/2022 | Almogy et al. |

FOREIGN PATENT DOCUMENTS

| | | |
|---|---|---|
| WO | WO-2023004421 A1 | 1/2023 |
| WO | WO-2023023357 A2 | 2/2023 |

OTHER PUBLICATIONS

Altschul, Stephen F. et al. Basic Local Alignment Search Tool. Journal of Molecular Biology 215(3):403-410 (1990).

Brenner, et al. Gene expression analysis by massively parallel signature sequencing (MPSS) on microbead arrays. Nat Biotechnol. Jun. 2000;18(6):630-4.

Brenner, S et al. In Vitro Cloning of Complex Mixtures of DNA on Microbeads: Physical Separation of Differentially Expressed cDNAs. Proceedings of the National Academy of Sciences of the United States of America vol. 97,4: pp. 1665-1670 (2000).

Co-pending U.S. Appl. No. 18/435,829, inventors Oberstrass; Florian et al., filed Feb. 7, 2024.

Dressman et al. Supplementary Information pp. 1-2 of article published 2003, PNAS 100(15:8817-22).

Lizardi, et al. Mutation detection and single-molecule counting using isothermal rolling-circle amplification. Nature Genetics vol. 19,3 (1998): 225-32.

Mitra, et al. Digital genotyping and haplotyping with polymerase colonies. Proceedings of the National Academy of Sciences of the United States of America vol. 100,10 (2003): 5926-31.

Mitra, et al. Fluorescent in situ sequencing on polymerase colonies. Analytical biochemistry vol. 320,1 (2003): 55-65.

Needleman, Saul B. and Christian wunsch D. A general method applicable to the search for similarities in the amino acid sequence of two proteins. Journal of Molecular Biology 48(3):444-453 (1970).

PCT/US2022/040935 International Preliminary Report on Patentability dated Feb. 29, 2024.

PCT/US2022/040935 International Search Report and Written Opinion dated Jun. 28, 2023.

Pemov, A. et al. DNA analysis with multiplex microarray-enhanced PCR. Nucleic acids research vol. 33:2 (2005): 1-9.

Raine, et al. SPlinted Ligation Adapter Tagging (SPLAT), a novel library preparation method for whole genome bisulphite sequencing. Nucleic Acids Research, vol. 45, No. 6 e36 (2017). Published online Nov. 29, 2016. 15 pages.

Reinartz, et al. Massively parallel signature sequencing (MPSS) as a tool for in-depth quantitative gene expression profiling in all organisms. Brief Funct Genomic Proteomic. Feb. 2002;1(1):95-104.

Schlingman, Daniel et al., A New Method for the Covalent Attachment of DNA to a Surface for Single-molecule Studies. Colloids and Surfaces B: Biointerfaces. 83(1):91-95 (2011).

Smith et al. Identification of common molecular subsequences. J Mol Biol 147:195-197 (1981).

Tabor, S. et al. Effect of manganese ions on the incorporation of dideoxynucleotides by bacteriophage T7 DNA polymerase and *Escherichia coli* DNA polymerase I, Proc. Natl. Acad. Sci. USA. (1989) 86:4076-80.

Troll et al. A Ligation-Based Single-Stranded Library Preparation Method to Analyze Cell-Free DNA and Synthetic Oligos. BMC Genomics 20(1):1023 (2019).

\* cited by examiner

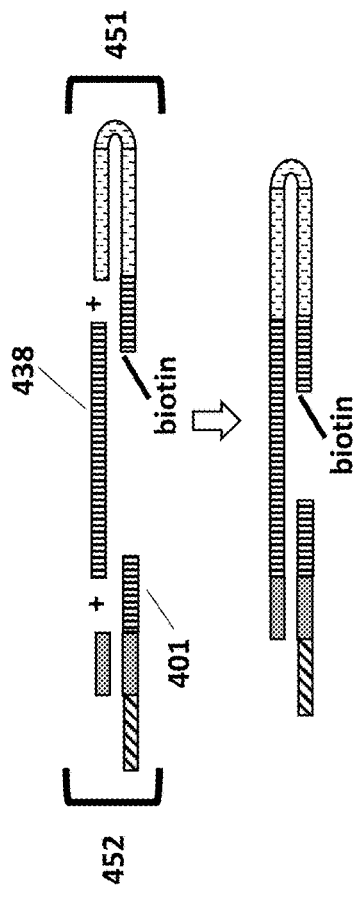
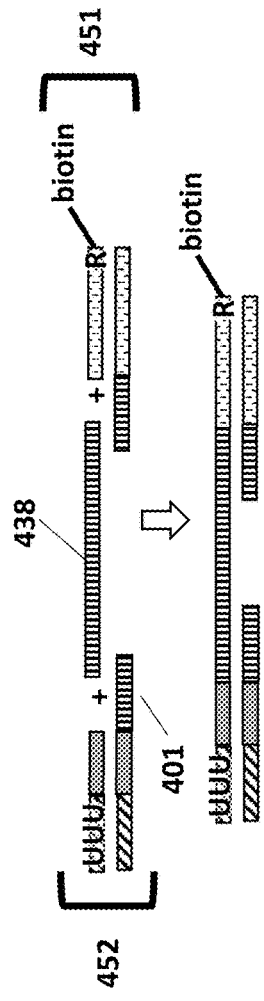
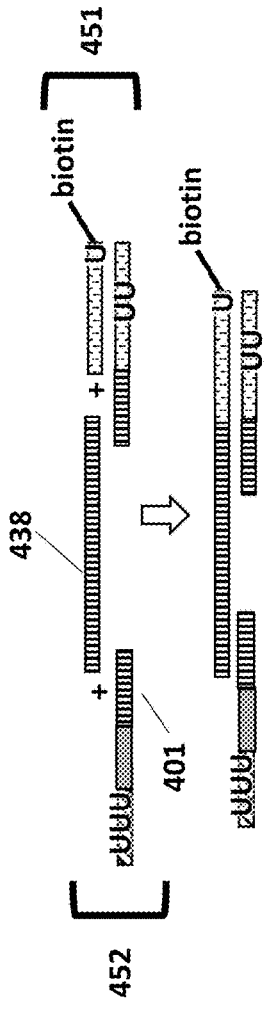
FIG. 4A
FIG. 4B
FIG. 4C

```
       CTGTCAGGGYCTTCC
  T T
  T T  GACAGTCGCCGGAAGG
   T
```
*FIG. 6A*
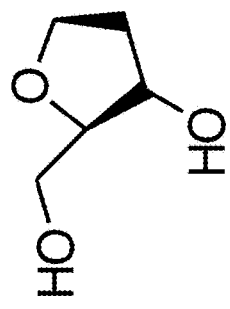
*FIG. 6B*
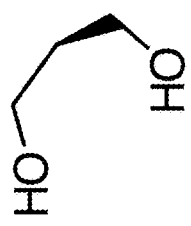
*FIG. 6C*

B1334

Std PE

2U Taq
50uM dNTP

10U Taq
50uM dNTP

58%   →   80%

MS081   B2 bridge   /5Phos/CCGCCTTCGCTGTCACCTGCTGATTTCT
MS082   PB28/B2 splint   /5Phos/GCGAGGCGGGAGACUGCCAAGGCCACAG*G/3C6/

FIG. 10

| | S1 | S2* | S3 | S4 | S5 | S6 | S7 |
|---|---|---|---|---|---|---|---|
| MS81 – B2 Bridge | 10 | 10 | 15 | 15 | 20 | 10 | 0 |
| MS82 – PB28/B2 Splint | 10 | 10 | 10 | 10 | 10 | 0 | 0 |
| MSB2 Library | 10 | 10 | 15 | 20 | 15 | 10 | 10 |
| Enrich % | 11.89% | 7.94% | 8.09% | 13.11% | 13.95% | 0.46% | 0.42% |
| % Left on SA Beads | 0.34% | 0.26% | 0.27% | 0.39% | 0.34% | 0.47% | 0.47% |

SYSTEMS AND METHODS FOR SEQUENCING ERROR CORRECTION VIA DOUBLE STRAND PRESERVATION

CROSS-REFERENCE

This application is a continuation of U.S. application Ser. No. 18/435,829, filed on Feb. 7, 2024, which is a continuation of the International Application No. PCT/US2022/040935, filed Aug. 19, 2022, which claims the priority benefit of U.S. Provisional Patent Application No. 63/235,451, filed Aug. 20, 2021, the contents of which are incorporated herein by reference in their entirety.

REFERENCE TO A SEQUENCE LISTING

The instant application contains a Sequence Listing which has been submitted electronically in XML format and is hereby incorporated by reference in its entirety. Said XML file, created on Feb. 10, 2023, is named Ultima_51024_766_601_SL.xml, and is 186,741 bytes in size.

BACKGROUND

Advances in the study of biological molecules have been led, in part, by improvements in technologies used to characterize molecules and/or their biological reactions. In particular, the study of nucleic acids has benefited from developing technologies used for sequence analysis. Sequencing of nucleic acids has various applications in the fields of molecular biology and medicine (e.g., diagnosis and treatment monitoring). Nucleic acid sequencing may provide information that may be used to diagnose a certain condition in a subject and/or tailor a treatment plan. Sequencing is widely used for molecular biology applications, including vector designs, gene therapy, vaccine design, industrial strain design and verification. The way in which an eventual sequence analysis is performed may play a role in the type and quality of information that may be obtained in such analysis.

SUMMARY

Recognized herein is the need for systems, methods, processes, and compositions for increasing the efficiency, sensitivity, and accuracy of methods for analyzing and/or processing nucleic acid samples. The present disclosure provides systems, methods, and compositions for analyzing and/or processing template (or sample) nucleic acid molecules (e.g., those found in biological samples) with high accuracy and sensitivity and efficient reagent usage. Provided herein are systems, methods, and compositions for attaching adapters to template inserts to prepare for amplification and/or sequencing. Provided herein are systems, methods, and compositions for amplifying nucleic acid molecules, such as in a library of template molecules, to prepare for sequencing. Provided herein are systems, methods, and compositions for sequencing templates and/or libraries prepared according to the methods described herein, as well as for analyzing sequencing information obtained from such sequencing.

Described herein are various methods for sample processing to correct sequencing errors, the methods comprising: providing a support-template assembly, wherein the support-template assembly comprises (i) a support comprising a first surface primer and a second surface primer and (ii) a template nucleic acid molecule comprising a first strand and a second strand, wherein the second strand comprises, at a 3' end, an overhang and a cleavable moiety, wherein at least a portion of the overhang is annealed to at least a portion of the first surface primer; cleaving the cleavable moiety from the second strand using at least an enzyme configured to cleave a DNA phosphodiester backbone at an AP site and generate a 3'-hydroxyl terminus in a cleaved second strand; extending the cleaved second strand using the first strand as a template to generate an extended second strand; and generating an extended support-template assembly comprising a second strand copy covalently bound to the support, by annealing the extended second strand to the second surface primer and extending the second surface primer using the extended second strand as a template. In some embodiments, the support is a bead. In some embodiments, prior to (b), the support is coupled to at most one template nucleic acid molecule amongst a library of template nucleic acid molecules. In some embodiments, the first strand is covalently bound to the support via ligation between the first strand and the first surface primer. In some embodiments, the extending in (c) is performed in a partition amongst a plurality of partitions. In some embodiments, the extending in (c) is performed in bulk solution in presence of at least one additional support-template assembly. In some embodiments, (d) is performed in a partition amongst a plurality of partitions. In some embodiments, the support comprises a plurality of surface primers including the first surface primer and the second surface primer, and further comprising subjecting the extended support-template assembly to amplification to generate an amplified support, wherein the amplified support comprises the first strand, copies of the first strand, the second strand copy, and copies of the second strand copies each covalently bound thereto. In some embodiments, the amplification is performed in a partition amongst a plurality of partitions. In some embodiments, the method further comprises subjecting the amplified support to sequencing. In some embodiments, the sequencing comprises annealing a plurality of sequencing primers to a plurality of strands of the amplified support, and extending the plurality of sequencing primers with sequential flow steps, wherein in a flow step of the sequential flow steps, a plurality of nucleotides of a single base are provided, and incorporation or lack thereof of the plurality of nucleotides are detected via sequencing signals. In some embodiments, the method further comprises detecting phasing at a particular flow step of the sequential flow steps, and ignoring or removing sequencing signals collected at that particular flow step and downstream of the particular flow step from base calling. In some embodiments, the method further comprises generating sequencing reads from non-removed sequencing signals, and aligning the sequencing reads to a reference. In some embodiments, the method further comprises identifying a single nucleotide polymorphism (SNP). In some embodiments, the cleavable moiety is a uracil residue. In some embodiments, the enzyme is an Apurinic/apyrimidinic Endonuclease 1 (APE1) enzyme. In some embodiments, (b) comprises providing a Uracil-DNA Glycosylase (UDG) enzyme. In some embodiments, (c) comprises using a Taq polymerase to extend the cleaved second strand.

Described herein are various methods for sample processing to correct sequencing errors, the methods comprising: obtaining a plurality of sequencing signals collected from performing a plurality of sequential sequencing flow steps on a support, wherein the support comprises a first strand of a template nucleic acid molecule, copies of the first strand, a second strand copy of a second strand of the template nucleic acid molecule, and copies of the second strand copies each covalently bound thereto; determining presence of phasing at a particular sequencing flow step of the plurality of sequential sequencing flow steps; ignoring or removing sequencing signals collected at that particular sequencing flow step and downstream of the particular sequencing flow step from base calling; and generating sequencing reads from non-removed sequencing signals of the plurality of sequencing signals. In some embodiments, the method further comprises identifying a base mismatch error at the particular sequencing flow step. In some embodiments, a base mismatch error comprises one of the following: a SNP, an indel, or an artificial base mismatch error. In some embodiments, identifying a base mismatch error comprises determining, for each sequencing flow step of the plurality of sequential sequencing flow steps, a read quality metric. In some embodiments, read quality metrics are determined based at least in part on one or more homopolymer probability values for the plurality of sequential sequencing flow steps. In some embodiments, for the one or more homopolymer probability values are other than a highest homopolymer probability value. In some embodiments, read quality metrics are determined based on a second highest probability value for the plurality of sequential sequencing flow steps. In some embodiments, determining presence of phasing at the particular sequencing flow step further comprises: determining a read quality metric moving average for the sequencing flow steps; selecting the particular sequencing flow step, wherein the particular sequencing flow step is the nth sequencing flow step having a moving average above a predetermined threshold, wherein n is a predefined number; and trimming at least a portion of the sequencing read comprising the particular sequencing flow step. In some embodiments, a predetermined number of consecutive sequencing flow steps prior to the selected sequencing flow step are trimmed. In some embodiments, the predetermined number of consecutive sequencing flow steps is a multiple of four. In some embodiments, the method further comprises storing the trimmed sequencing data in a non-transitory computer readable medium. In some embodiments, the method further comprises aligning sequencing reads in the trimmed sequencing data to a reference sequence. In some embodiments, the method further comprises obtaining, for each of a plurality of supports: obtaining a plurality of sequencing signals collected from performing a plurality of sequential sequencing flow steps on a support, wherein the support comprises a first strand of a template nucleic acid molecule, copies of the first strand, a second strand copy of a second strand of the template nucleic acid molecule, and copies of the second strand copies each covalently bound thereto; determining presence of phasing at a particular sequencing flow step of the plurality of sequential sequencing flow steps; ignoring or removing sequencing signals collected at that particular sequencing flow step and downstream of the particular sequencing flow step from base calling; and generating sequencing reads from non-removed sequencing signals of the plurality of sequencing signals. In some embodiments, the method further comprises, for a subset of the plurality of supports, identifying a base mismatch error, wherein, for at least one support of the subset of the plurality of supports, the base mismatch error is an artificial base mismatch error. In some embodiments, the artificial base mismatch error does not originate from a sample from which the template nucleic acid molecule originated from. In some embodiments, the artificial base mismatch error comprises an amplification error.

Described herein are various systems for sample processing to correct sequencing errors, the systems comprising: one or more computer processors, individually or collectively, configured to obtain a plurality of sequencing signals collected from performing a plurality of sequential sequencing flow steps on a support, wherein the support comprises a first strand of a template nucleic acid molecule, copies of the first strand, a second strand copy of a second strand of the template nucleic acid molecule, and copies of the second strand copies each covalently bound thereto; determine presence of phasing at a particular sequencing flow step of the plurality of sequential sequencing flow steps; ignore or remove sequencing signals collected at that particular sequencing flow step and downstream of the particular sequencing flow step from base calling; and generate sequencing reads from non-removed sequencing signals of the plurality of sequencing signals. In some embodiments, the one or more computer processors, individually or collectively, are further configured to identify an artificial base mismatch error at the particular sequencing flow step, which artificial base mismatch error does not originate from a sample from which the template nucleic acid molecule originated from.

Described herein are various methods for sample processing to correct sequencing errors, the methods comprising: providing a template insert molecule, a first adapter that is partially double-stranded, and a second adapter that is partially double-stranded, wherein the first adapter comprises a first strand and a second strand, the first strand comprising at a 5' end an overhang comprising a first capture sequence, wherein the first adapter comprises a barcode sequence, wherein the second adapter comprises a third strand and a fourth strand, the third strand comprising at a 3' end an overhang comprising a second capture sequence; attaching the first adapter and the second adapter to the template insert molecule to generate an adapter-ligated template insert molecule, via (i) annealing the first capture sequence and the second capture sequence, respectively, to the template insert molecule, and (ii) ligating the second strand and the fourth strand to the template insert molecule, respectively; generating a template nucleic acid molecule using the adapter-ligated template insert molecule, a first primer, and a second primer, wherein the first primer comprises a capture moiety at a 5' end, a cleavable moiety, and a first sequence corresponding to a sequence of the first adapter, wherein the second primer comprises a second sequence corresponding to a sequence of the second adapter, wherein the template nucleic acid molecule comprises the capture moiety at a first end; cleaving the cleavable moiety to generate a cleaved template nucleic acid molecule comprising an overhang; coupling the cleaved template nucleic acid molecule to a support by annealing the overhang to a surface primer of the support, to generate a support-template assembly; and isolating the support-template assembly, from a plurality of supports unbound to any template nucleic acid molecule of a library of template nucleic acid molecules, by capturing the capture moiety. In some embodiments, the support is a bead. In some embodiments, the capture moiety comprises a biotin. In some embodiments, the first capture sequence, the second capture sequence, or both comprises a random N-mer sequence. In some embodiments, the second adapter comprises in the fourth strand the following one or more sequence segments, in a 5' to 3' direction: [functional sequence 1] and in the third strand the following one or more sequence segments, in a 3' to 5' direction: [random N-mer], [functional sequence 1], wherein a sequence segment corresponds to a particular sequence or its complement. In some embodiments, the first adapter comprises in the second strand the following one or more sequence segments, in a 5' to 3' direction: [functional sequence 2], [barcode], [functional sequence 3] and in the first strand the following one or more sequence segments, in a 3' to 5' direction: [functional sequence 2], [barcode], [functional sequence 3], [random N-mer] wherein a sequence segment corresponds to a particular sequence or its complement. In some embodiments, the second primer comprises the following one or more sequence segments, in a 5' to 3' direction: [functional sequence 4], [functional sequence 2], wherein a sequence segment corresponds to a particular sequence or its complement. In some embodiments, the first primer comprises the following one or more sequence segments, in a 3' to 5' direction: [functional sequence 1], [functional sequence 5], wherein a sequence segment corresponds to a particular sequence or its complement. In some embodiments, the template nucleic acid molecule comprises a strand comprising the following one or more sequence segments, in a 5' to 3' direction: [functional sequence 4], [functional sequence 2], [barcode], [functional sequence 3], [insert], [functional sequence 1], [functional sequence 5], wherein a sequence segment corresponds to a particular sequence or its complement. In some embodiments, the cleavable moiety is a uracil. In some embodiments, the third strand of the second adapter comprises an amino blocking group at the 3' end. In some embodiments, the method further comprises a plurality of first adapters, wherein each of the plurality of first adapters comprises a different barcode sequence.

Described herein are various methods for sample processing to correct sequencing errors, the methods comprising: providing a template insert molecule, a first adapter that is partially double-stranded, and a second adapter that is partially double-stranded, wherein the first adapter comprises a first strand and a second strand, the first strand comprising at a 5' end an overhang comprising a first capture sequence, wherein the first adapter comprises a universal sequence, wherein the second adapter comprises a third strand and a fourth strand, the third strand comprising at a 3' end an overhang comprising a second capture sequence; attaching the first adapter and the second adapter to the template insert molecule to generate an adapter-ligated template insert molecule, via (i) annealing the first capture sequence and the second capture sequence, respectively, to the template insert molecule, and (ii) ligating the second strand and the fourth strand to the template insert molecule, respectively; generating a template nucleic acid molecule using the adapter-ligated template insert molecule, a first primer, and a second primer, wherein the first primer comprises a capture moiety at a 5' end, a cleavable moiety, and a first sequence corresponding to the universal sequence of the first adapter, wherein the second primer comprises a second sequence corresponding to a sequence of the second adapter, wherein the template nucleic acid molecule comprises the capture moiety at a first end; cleaving the cleavable moiety to generate a cleaved template nucleic acid molecule comprising an overhang; coupling the cleaved template nucleic acid molecule to a support by annealing the overhang to a surface primer of the support, to generate a support-template assembly; and isolating the support-template assembly, from a plurality of supports unbound to any template nucleic acid molecule of a library of template nucleic acid molecules, by capturing the capture moiety. In some embodiments, the support is a bead. In some embodiments, the capture moiety comprises a biotin. In some embodiments, the first capture sequence, the second capture sequence, or both comprises a random N-mer sequence. In some embodiments, the second adapter comprises in the fourth strand the following one or more sequence segments, in a 5' to 3' direction: [functional sequence 1] and in the third strand the following one or more sequence segments, in a 3' to 5' direction: [random N-mer], [functional sequence 1], wherein a sequence segment corresponds to a particular sequence or its complement. In some embodiments, the first adapter comprises in the second strand the following one or more sequence segments, in a 5' to 3' direction: [universal sequence], and in the first strand the following one or more sequence segments, in a 3' to 5' direction: [universal sequence], [random N-mer] wherein a sequence segment corresponds to a particular sequence or its complement. In some embodiments, the second primer comprises the following one or more sequence segments, in a 5' to 3' direction: [functional sequence 4], [functional sequence 2], [barcode], [functional sequence 3], [universal seq], wherein a sequence segment corresponds to a particular sequence or its complement. In some embodiments, the first primer comprises the following one or more sequence segments, in a 3' to 5' direction: [functional sequence 1], [functional sequence 5], wherein a sequence segment corresponds to a particular sequence or its complement. In some embodiments, the template nucleic acid molecule comprises a strand comprising the following one or more sequence segments, in a 5' to 3' direction: [functional sequence 4], [functional sequence 2], [barcode], [functional sequence 3], [universal sequence], [insert], [functional sequence 1], [functional sequence 5], wherein a sequence segment corresponds to a particular sequence or its complement. In some embodiments, the cleavable moiety is a uracil. In some embodiments, the third strand of the second adapter comprises an amino blocking group at the 3' end. In some embodiments, the method further comprises a plurality of first adapters, wherein each of the plurality of first adapters comprises the same universal sequence.

Described here are various methods for sample processing to correct sequencing errors, the methods comprising: providing a template insert molecule and a first adapter that is partially double-stranded, wherein the first adapter comprises a first strand and a second strand, the first strand comprising at a 3' end an overhang comprising a capture sequence; attaching the first adapter to the template insert molecule to generate an adapter-ligated template insert molecule, via (i) annealing the capture sequence to the template insert molecule, and (ii) ligating the second strand to the template insert molecule; generating an intermediary molecule using the adapter-ligated template insert molecule and a primer, wherein the primer comprises a first sequence corresponding to a sequence of the first adapter; generating a template nucleic acid molecule using the intermediary molecule and a second adapter that is partially double-stranded, wherein the second adapter comprises a third strand and a fourth strand, the third strand comprising a capture moiety at a 5' end, a cleavable moiety, and a second sequence, wherein the template nucleic acid molecule comprises the capture moiety at a first end; cleaving the cleavable moiety to generate a cleaved template nucleic acid molecule comprising an overhang; coupling the cleaved template nucleic acid molecule to a support by annealing the overhang to a surface primer of the support, to generate a support-template assembly; and isolating the support-template assembly, from a plurality of supports unbound to any template nucleic acid molecule of a library of template nucleic acid molecules, by capturing the capture moiety. In some embodiments, the support is a bead. In some embodiments, the capture moiety comprises a biotin. In some embodiments, the capture sequence comprises a random N-mer sequence. In some embodiments, the first adapter comprises in the second strand the following one or more sequence segments, in a 5' to 3' direction: [functional sequence 1], [functional sequence 5], and in the first strand the following one or more sequence segments, in a 3' to 5' direction: [random N-mer], [functional sequence 1], wherein a sequence segment corresponds to a particular sequence or its complement. In some embodiments, the primer comprises the following one or more sequence segments, in a 3' to 5' direction: [functional sequence 1], wherein a sequence segment corresponds to a particular sequence or its complement. In some embodiments, the second adapter comprises in the third strand the following one or more sequence segments, in a 5' to 3' direction: [functional sequence 4], [functional sequence 2], [barcode], [functional sequence 3], and in the first strand the following one or more sequence segments, in a 3' to 5' direction: [functional sequence 4], [functional sequence 2], [barcode], [functional sequence 3] wherein a sequence segment corresponds to a particular sequence or its complement. In some embodiments, the cleavable moiety is a uracil. In some embodiments, the first strand of the first adapter comprises an amino blocking group at the 3' end.

In some embodiments, the second adapter comprises (i) in a 5' to 3' direction, a functional sequence in the fourth strand, and (ii) in a 3' to 5' direction, a random N-mer and/or the functional sequence. In some embodiments, the functional sequence may comprise an adapter, a primer, an index, or barcode sequence. In some embodiments, the functional sequences may be any functional sequence described herein. In some embodiments, the functional sequences may be any functional sequence described herein and at least a portion of the [random N-mer] is an overhang.

Another aspect of the present disclosure provides a system comprising one or more computer processors and computer memory coupled thereto. The computer memory comprises machine executable code that, upon execution by the one or more computer processors, implements any of the methods above or elsewhere herein. Another aspect of the present disclosure provides a non-transitory computer readable medium comprising machine executable code that, upon execution by one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2A illustrates an example where adapters including one or more cleavable moieties (e.g., a uracil or a ribonucleotide) are used. FIG. 2B illustrates an example where adapters comprising one or more cleavable moieties of different types (e.g., a uracil and a ribonucleic acid) are used. FIG. 2C illustrates an example where different support species having surface primer sequences complementary to different adapter sequences can be used to bind to template nucleic acid molecules to decrease the possibility of different template nucleic acid molecules binding to the same support. FIG. 2D illustrates an alternative pre-enrichment process where pre-enrichment occurs via hybridization of complementary sequences.

FIGS. 4A-4C illustrate example adapter molecules which may be ligated to template sequences to generate template nucleic acid molecules (e.g., of a library of template nucleic acid molecules).

FIGS. 6A-6C shows example oligonucleotides or modified bases, as described herein. FIG. 6A shows an example hairpin oligonucleotide. FIG. 6B shows a dSpacer moiety and FIG. 6C shows a C3 Spacer (linker). Figure discloses SEQ ID NO: 44.

FIG. 10 shows an example splint oligonucleotide molecule. Figure discloses SEQ ID NOS 45-48, respectively, in order of appearance.

FIG. 11 shows example data of pre-enrichment efficiencies using a splint molecule and bridge molecule for attachment of template nucleic acid molecules to a support.

FIG. 13A shows additional example adapter sequences for generating template nucleic acid molecules (e.g., of a library of template nucleic acid molecules).

FIG. 17A shows addition of a first adapter sequence. FIG. 17B shows addition of a second adapter sequence. Figure discloses SEQ ID NOS 61-63, 62, 64-66 and 65-72, respectively, in order of appearance.

FIG. 25A illustrates an exemplary summary of detected signals after a number of exemplary flow cycles are performed, in accordance with some embodiments. Figure discloses SEQ ID NO: 83.

FIG. 25B illustrates an exemplary process for determining a preliminary sequence, in accordance with some embodiments. Figure discloses SEQ ID NO: 83.

DETAILED DESCRIPTION

Figure 1:
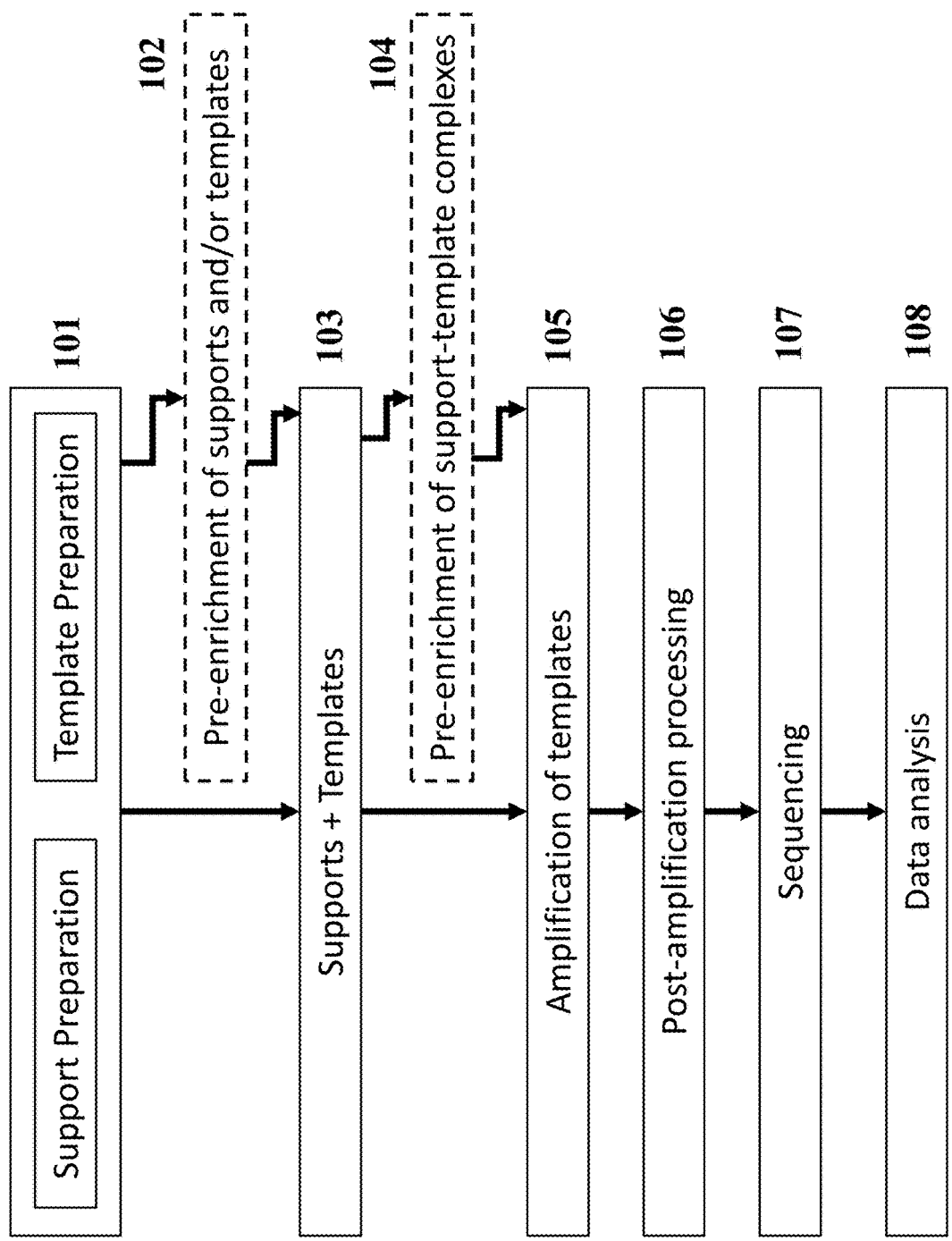
FIG. 1 illustrates an example workflow for processing a sample for sequencing.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the singular forms "a," "an," and "the" include the plural reference unless the context clearly dictates otherwise.

When a range of values is provided, it is to be understood that each intervening value between the upper and lower limit of that range, and any other stated or intervening value in that stated range is encompassed within the scope of the present disclosure. Where the stated range includes upper or lower limits, ranges excluding either of those included limits are also included in the present disclosure. Ranges may be expressed herein as from "about" one particular value, and/or to "about" another particular value. The terms "about" and "approximately" shall generally mean an acceptable degree of error or variation for a given value or range of values, such as, for example, a degree of error or variation that is within 20 percent (%), within 15%, within 10%, or within 5% of a given value or range of values.

The term "biological sample," as used herein, generally refers to any sample derived from a subject or specimen. The biological sample can be a fluid, tissue, collection of cells (e.g., cheek swab), hair sample, or feces sample. The fluid can be blood (e.g., whole blood), saliva, urine, or sweat. The tissue can be from an organ (e.g., liver, lung, or thyroid), or a mass of cellular material, such as, for example, a tumor. The biological sample can be a cellular sample or cell-free sample. Examples of biological samples include nucleic acid molecules, amino acids, polypeptides, proteins, carbohydrates, fats, or viruses. In an example, a biological sample is a nucleic acid sample including one or more nucleic acid molecules, such as deoxyribonucleic acid (DNA) and/or ribonucleic acid (RNA). The nucleic acid sample may comprise cell-free nucleic acid molecules, such as cell-free DNA or cell-free RNA. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides may be fetal in origin (via fluid taken from a pregnant subject) or may be derived from tissue of the subject itself. A biological sample may also refer to a sample engineered to mimic one or more properties (e.g., nucleic acid sequence properties, e.g., sequence identity, length, GC content, etc.) of a sample derived from a subject or specimen.

The term "subject," as used herein, generally refers to an individual from whom a biological sample is obtained. The subject may be a mammal or non-mammal. The subject may be human, non-human mammal, animal, ape, monkey, chimpanzee, reptilian, amphibian, avian, or a plant. The subject may be a patient. The subject may be displaying a symptom of a disease. The subject may be asymptomatic. The subject may be undergoing treatment. The subject may not be undergoing treatment. The subject can have or be suspected of having a disease, such as cancer (e.g., breast cancer, colorectal cancer, brain cancer, leukemia, lung cancer, skin cancer, liver cancer, pancreatic cancer, lymphoma, esophageal cancer, cervical cancer, etc.) or an infectious disease. The subject can have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease.

The term "analyte," as used herein, generally refers to an object that is the subject of analysis, or an object, regardless of being the subject of analysis, that is directly or indirectly analyzed during a process. An analyte may be synthetic. An analyte may be, originate from, and/or be derived from, a sample, such as a biological sample. In some examples, an analyte is or includes a molecule, macromolecule (e.g., nucleic acid, carbohydrate, protein, lipid, etc.), nucleic acid, carbohydrate, lipid, antibody, antibody fragment, antigen, peptide, polypeptide, protein, macromolecular group (e.g., glycoproteins, proteoglycans, ribozymes, liposomes, etc.), cell, tissue, biological particle, or an organism, or any engineered copy or variant thereof, or any combination thereof. The term "processing an analyte," as used herein, generally refers to one or more stages of interaction with one more samples. Processing an analyte may comprise conducting a chemical reaction, biochemical reaction, enzymatic reaction, hybridization reaction, polymerization reaction, physical reaction, any other reaction, or a combination thereof with, in the presence of, or on, the analyte. Processing an analyte may comprise physical and/or chemical manipulation of the analyte. For example, processing an analyte may comprise detection of a chemical change or physical change, addition of or subtraction of material, atoms, or molecules, molecular confirmation, detection of the presence of a fluorescent label, detection of a Forster resonance energy transfer (FRET) interaction, or inference of absence of fluorescence.

The terms "nucleic acid," "nucleic acid molecule," "nucleic acid sequence," "nucleic acid fragment," "oligonucleotide" and "polynucleotide," as used herein, generally refer to a polynucleotide that may have various lengths of bases, comprising, for example, deoxyribonucleotide, deoxyribonucleic acid (DNA), ribonucleotide, or ribonucleic acid (RNA), or analogs thereof. A nucleic acid may be single-stranded. A nucleic acid may be double-stranded. A nucleic acid may be partially double-stranded, such as to have at least one double-stranded region and at least one single-stranded region. A partially double-stranded nucleic acid may have one or more overhanging regions. An "overhang," as used herein, generally refers to a single-stranded portion of a nucleic acid that extends from or is contiguous with a double-stranded portion of a same nucleic acid molecule and where the single-stranded portion is at a 3' or 5' end of the same nucleic acid molecule. Non-limiting examples of nucleic acids include DNA, RNA, genomic DNA or synthetic DNA/RNA or coding or non-coding regions of a gene or gene fragment, loci (locus) defined from linkage analysis, exons, introns, messenger RNA (mRNA), transfer RNA, ribosomal RNA (rRNA), short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, and isolated RNA of any sequence. A nucleic acid can have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 20 kb, 30 kb, 40 kb, 50 kb, 100 kb, 200 kb, 300 kb, 400 kb, 500 kb, 1 megabase (Mb), 10 Mb, 100 Mb, 1 gigabase or more. A nucleic acid can comprise a sequence of four natural nucleotide bases: adenine (A); cytosine (C); guanine (G); and thymine (T) (or uracil (U) instead of thymine (T) when the nucleic acid is RNA). A nucleic acid may include one or more nonstandard nucleotide(s), nucleotide analog(s) and/or modified nucleotide(s).

The term "nucleotide," as used herein, generally refers to any nucleotide or nucleotide analog. The nucleotide may be naturally occurring or non-naturally occurring. The nucleotide may be a modified, synthesized, or engineered nucleotide. The nucleotide may include a canonical base or a non-canonical base. The nucleotide may comprise an alternative base. The nucleotide may include a modified polyphosphate chain (e.g., triphosphate coupled to a fluorophore). The nucleotide may comprise a label. The nucleotide may be terminated (e.g., reversibly terminated). Nonstandard nucleotides, nucleotide analogs, and/or modified analogs may include, but are not limited to, diaminopurine, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids and the like. In some cases, nucleotides may include modifications in their phosphate moieties, including modifications to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates) or modifications with selenium moieties (e.g., phosphoroselenoate nucleic acids). Nucleic acids may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acids may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Nucleotides may be capable of reacting or bonding with detectable moieties for nucleotide detection.

The term "sequencing," as used herein, generally refers to a process for generating or identifying a sequence of a biological molecule, such as a nucleic acid. The sequence may be a nucleic acid sequence which comprises a sequence of nucleic acid bases. As used herein, the term "template nucleic acid" generally refers to the nucleic acid to be sequenced. The template nucleic acid may be an analyte or be associated with an analyte. For example, the analyte can be a mRNA, and the template nucleic acid is the mRNA or a cDNA derived from the mRNA, or other derivative thereof. In another example, the analyte can be a protein, and the template nucleic acid is an oligonucleotide that is conjugated to an antibody that binds to the protein, or derivative thereof. Examples of sequencing include single molecule sequencing or sequencing by synthesis, for example. Sequencing may comprise generating sequencing signals and/or sequencing reads. Sequencing may be performed on template nucleic acids immobilized on a support, such as a flow cell, substrate, and/or one or more beads. In some cases, a template nucleic acid may be amplified to produce a colony of nucleic acid molecules attached to the support to produce amplified sequencing signals. In one example, (i) a template nucleic acid is subjected to a nucleic acid reaction, e.g., amplification, to produce a clonal population of the nucleic acid attached to a bead, the bead immobilized to a substrate, (ii) amplified sequencing signals from the immobilized bead are detected from the substrate surface during or following one or more nucleotide flows, and (iii) the sequencing signals are processed to generate sequencing reads. The substrate surface may immobilize multiple beads at distinct locations, each bead containing distinct colonies of nucleic acids, and upon detecting the substrate surface, multiple sequencing signals may be simultaneously or substantially simultaneously processed from the different immobilized beads at the distinct locations to generate multiple sequencing reads. In some sequencing methods, the nucleotide flows comprise non-terminated nucleotides. In some sequencing methods, the nucleotide flows comprise terminated nucleotides.

The term "nucleotide flow" as used herein, generally refers to a temporally distinct instance of providing a nucleotide-containing reagent to a sequencing reaction space. The term "flow" as used herein, when not qualified by another reagent, generally refers to a nucleotide flow. For example, providing two flows may refer to (i) providing a nucleotide-containing reagent (e.g., an A-base-containing solution) to a sequencing reaction space at a first time point and (ii) providing a nucleotide-containing reagent (e.g., G-base-containing solution) to the sequencing reaction space at a second time point different from the first time point. A "sequencing reaction space" may be any reaction environment comprising a template nucleic acid. For example, the sequencing reaction space may be or comprise a substrate surface comprising a template nucleic acid immobilized thereto; a substrate surface comprising a bead immobilized thereto, the bead comprising a template nucleic acid immobilized thereto; or any reaction chamber or surface that comprises a template nucleic acid, which may or may not be immobilized. A nucleotide flow can have any number of base types (e.g., A, T, G, C; or U), for example 1, 2, 3, or 4 canonical base types. A "flow order," as used herein, generally refers to the order of nucleotide flows used to sequence a template nucleic acid. A flow order may be expressed as a one-dimensional matrix or linear array of bases corresponding to the identities of, and arranged in chronological order of, the nucleotide flows provided to the sequencing reaction space:

(e.g., [A T G C A T G C A T G A T G A T G A T G C A T G C (SEQ ID NO: 2)]).

Such one-dimensional matrix or linear array of bases in the flow order may also be referred to herein as a "flow space." A flow order may have any number of nucleotide flows. A "flow position," as used herein, generally refers to the sequential position of a given nucleotide flow entry in the flow space (e.g., an element in the one-dimensional matrix or linear array). A "flow cycle," as used herein, generally refers to the order of nucleotide flow(s) of a sub-group of contiguous nucleotide flow(s) within the flow order. A flow cycle may be expressed as a one-dimensional matrix or linear array of an order of bases corresponding to the identities of, and arranged in chronological order of, the nucleotide flows provided within the sub-group of contiguous flow(s) (e.g., [A T G C], [A A T T G G C C], [A T], [A/T A/G], [A A], [A], [A T G], etc.). A flow cycle may have any number of nucleotide flows. A given flow cycle may be repeated one or more times in the flow order, consecutively or non-consecutively. Accordingly, the term "flow cycle order," as used herein, generally refers to an ordering of flow cycles within the flow order and can be expressed in units of flow cycles. For example, where [A T G C] is identified as a $1^{st}$ flow cycle, and [A T G] is identified as a $2^{nd}$ flow cycle, the flow order of [A T G C A T G C A T G A T G A T G A T G C A T G C (SEQ ID NO: 2)] may be described as having a flow-cycle order of [$1^{st}$ flow cycle; $1^{st}$ flow cycle; $2^{nd}$ flow cycle; $2^{nd}$ flow cycle; $2^{nd}$ flow cycle; $1^{st}$ flow cycle; $1^{st}$ flow cycle]. Alternatively or in addition, the flow cycle order may be described as [cycle 1, cycle, 2, cycle 3, cycle 4, cycle 5, cycle 6], where cycle 1 is the $1^{st}$ flow cycle, cycle 2 is the $1^{st}$ flow cycle, cycle 3 is the $2^{nd}$ flow cycle, etc.

The terms "amplifying," "amplification," and "nucleic acid amplification" are used interchangeably and generally refer to generating one or more copies, or an extension product (e.g., a product of a primer extension reaction on the nucleic acid molecule), of a nucleic acid or a template. Amplification of a nucleic acid may be linear, exponential, or a combination thereof. Amplification may be emulsion based or non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification (RCA), recombinase polymerase reaction (RPA), loop mediated isothermal amplification (LAMP), nucleic acid sequence-based amplification (NASBA), self-sustained sequence replication (3SR), and multiple displacement amplification (MDA). Where PCR is used, any form of PCR may be used, with non-limiting examples that include real-time PCR, allele-specific PCR, assembly PCR, asymmetric PCR, digital PCR, emulsion PCR (ePCR or emPCR), dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, and touchdown PCR. Amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C. C. PNAS, 1989, 86, 4076-4080 and U.S. Pat. Nos. 5,409,811 and 5,674,716, each of which is herein incorporated by reference in its entirety. Useful methods for clonal amplification from single molecules include rolling circle amplification (RCA) (Lizardi et al., Nat. Genet. 19:225-232 (1998), which is incorporated herein by reference), bridge PCR (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Adessi et al., Nucl. Acids Res. 28:E87 (2000); Pemov et al., Nucl. Acids Res. 33:e11(2005); or U.S. Pat. No. 5,641,658, each of which is incorporated herein by reference), polony generation (Mitra et al., Proc. Natl. Acad. Sci. USA 100:5926-5931 (2003); Mitra et al., Anal. Biochem. 320:55-65(2003), each of which is incorporated herein by reference), and clonal amplification on beads using emulsions (Dressman et al., Proc. Natl. Acad. Sci. USA 100:8817-8822 (2003), which is incorporated herein by reference) or ligation to bead-based adapter libraries (Brenner et al., Nat. Biotechnol. 18:630-634 (2000); Brenner et al., Proc. Natl. Acad. Sci. USA 97:1665-1670 (2000)); Reinartz, et al., Brief Funct. Genomic Proteomic 1:95-104 (2002), each of which is incorporated herein by reference). Amplification products from a nucleic acid may be identical or substantially identical. A nucleic acid colony resulting from amplification may have identical or substantially identical sequences. An amplicon can be single-stranded or double-stranded irrespective of whether the initial template is single-stranded or double-stranded.

The terms "reference genome" and "reference sequence," as used herein, generally refer to a standardized genomic sequence or a portion thereof (e.g., any genome known in the art). A reference genome may be a representative example of a set of genes. A reference sequence may be a portion of a reference genome (e.g., a representative example of a gene). In some instances, a reference genome is generalized to a species (e.g., *Homo sapiens*) and is determined from one or more assembled or partially assembled genome sequences of one or more individuals of said species. In some instances, a reference genome is specific to an individual of a species, and in such instances the reference genome may be determined from one or more assembled or partially assembled genome sequences from said individual. A reference genome may be any portion of a genomic nucleic acid sequence (e.g., a targeted panel of genes, one or more chromosomes, an entire genome of a species, etc.) that is used as a comparison for generated nucleic acid sequencing data (e.g., sequencing information generated according to sequencing methods described herein). Examples of human reference genomes include NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38). Additional reference genomes can be found online in the National Center for Biotechnology Information (NCBI) of the University of California, Santa Cruz (UCSC) genome browsers.

As used herein, the terms "identical" or "percent identity," when used with respect to two or more nucleic acid or polypeptide sequences, refer to two or more sequences that are the same or, alternatively, have a specified percentage of amino acid residues or nucleotides that are the same, when compared and aligned for maximum correspondence, as measured using any one or more of the following sequence comparison algorithms: Needleman-Wunsch (see, e.g., Needleman, Saul B.; and Wunsch, Christian D. (1970). "A general method applicable to the search for similarities in the amino acid sequence of two proteins" Journal of Molecular Biology 48 (3):443-53); Smith-Waterman (see, e.g., Smith, Temple F.; and Waterman, Michael S., "Identification of Common Molecular Subsequences" (1981) Journal of Molecular Biology 147:195-197); or BLAST (Basic Local Alignment Search Tool; see, e.g., Altschul S F, Gish W, Miller W, Myers E W, Lipman D J, "Basic local alignment search tool" (1990) J Mol Biol 215 (3):403-410). As used herein, the terms "substantially identical" or "substantial identity" when used with respect to two or more nucleic acid or polypeptide sequences, refer to two or more sequences or subsequences (such as biologically active fragments) that have at least 60%, at least 70%, at least 75%, at least 80%, at least 85%, at least 90%, at least 95%, at least 96%, at least 97%, at least 98%, or at least 99% nucleotide or amino acid residue identity, when compared and aligned for maximum correspondence, as measured using a sequence comparison algorithm or by visual inspection. Substantially identical sequences are typically considered to be homologous without reference to actual ancestry. In some embodiments, "substantial identity" exists over a region of the sequences being compared. In some embodiments, substantial identity exists over a region of at least 25 residues in length, at least 50 residues in length, at least 100 residues in length, at least 150 residues in length, at least 200 residues in length, or greater than 200 residues in length. In some embodiments, the sequences being compared are substantially identical over the full length of the sequences being compared. Typically, substantially identical nucleic acid or protein sequences include less than 100% nucleotide or amino acid residue identity, and as such sequences would generally be considered "identical."

The term "clonal," as used herein, generally refers to a population of nucleic acids for which a substantial portion (e.g., greater than 50%, 60%, 70%, 80%, 90%, 95%, or 99%) of its members have substantially identical sequences. Members of a clonal population of nucleic acid molecules may have sequence homology to one another, to a template nucleic acid molecule, or to a complement of the template nucleic acid molecule (e.g., if single-stranded). Members of the clonal population may be double-stranded or single-stranded. Members of a population may not be 100% identical or complementary because, e.g., "errors" may occur during the course of synthesis such that a minority of a given population may not have sequence homology with a majority of the population. For example, at least 50%, 60%, 70%, 80%, 90%, 95%, 99% or more of the members of a population may be substantially identical to each other or to a reference nucleic acid molecule (i.e., a molecule of defined sequence used as a basis for a sequence comparison).

The term "complementary sequence," as used herein, generally refers to a sequence that hybridizes to another sequence or has sequence complementarity with such other sequence. Hybridization between two single-stranded nucleic acid molecules may involve the formation of a double-stranded structure that is stable under certain conditions. Two single-stranded polynucleotides may be considered to be hybridized if they are bonded to each other by two or more sequentially adjacent base pairings. A substantial proportion of nucleotides in one strand of a double-stranded structure may undergo Watson-Crick base-pairing with a nucleoside on the other strand. Hybridization may also include the pairing of nucleoside analogs, such as deoxyinosine, nucleosides with 2-aminopurine bases, and the like, that may be employed to reduce the degeneracy of probes, whether or not such pairing involves formation of hydrogen bonds.

The term "denaturation," as used herein, generally refers to separation of a double-stranded molecule (e.g., DNA) into single-stranded molecules. Denaturation may be complete or partial denaturation. In partial denaturation, a single-stranded region may form in a double-stranded molecule by denaturation of the two deoxyribonucleic acid (DNA) strands flanked by double-stranded regions in DNA.

The terms "polymerase," "polymerizing enzyme, or "polymerization enzyme," as used herein, generally refer to an enzyme capable of catalyzing a polymerization reaction. A polymerizing enzyme may be used to extend a nucleic acid primer paired with a template strand by incorporation of nucleotides or nucleotide analogs. A polymerizing enzyme may add a new strand of DNA by extending the 3' end of an existing nucleotide chain, adding new nucleotides matched to the template strand one at a time via the creation of phosphodiester bonds. A polymerizing enzyme may be a polymerase such as a nucleic acid polymerase. A polymerase may be naturally occurring or synthesized. A polymerase may have relatively high processivity, namely the capability of the polymerase to consecutively incorporate nucleotides into a nucleic acid template without releasing the nucleic acid template. A polymerizing enzyme may be a transcriptase. Examples of polymerases include, but are not limited to, a DNA polymerase, an RNA polymerase, a thermostable polymerase, a wild-type polymerase, a modified polymerase, E. coli DNA polymerase I, T7 DNA polymerase, bacteriophage T4 DNA polymerase, Φ29 (phi29) DNA polymerase, Taq polymerase, Tth polymerase, Tli polymerase, Pfu polymerase, Pwo polymerase, VENT polymerase, DEEPVENT polymerase, EXTaq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. A polymerase may be a single subunit polymerase. The polymerase may have high processivity, namely the capability of the polymerase to consecutively incorporate nucleotides in a nucleic acid template without releasing the nucleic acid template.

The term "coupled to," as used herein, generally refers to an association between two or more objects that may be temporary or substantially permanent. A first object may be reversibly or irreversibly coupled to a second object. For example, a nucleic acid molecule may be reversibly coupled to a particle or support. A reversible coupling may comprise, for example, a releasable coupling (e.g., in which a first object may be released from a second object to which it is coupled). A first object releasably coupled to a second object may be separated from the second object, e.g., upon application of a stimulus, which stimulus may comprise a photostimulus (e.g., ultraviolet light), a thermal stimulus, a chemical stimulus (e.g., reducing agent), or any other useful stimulus. Coupling may encompass immobilization to a support (e.g., as described herein). Similarly, coupling may encompass attachment, such as attachment of a first object to a second object. A coupling may comprise any interaction that affects an association between two objects, including, for example, a covalent bond, a non-covalent interaction (e.g., electrostatic interaction [e.g., hydrogen bonding, ionic interaction, and halogen bonding], π-interaction [e.g., π-π interaction, polar-π interaction, cation-π interaction, and anion-π interaction], van der Waals force-based interactions [e.g., dipole-dipole interactions, dipole-induced dipole interactions, and induced dipole-induced dipole interactions], hydrophobic interaction), a magnetic interaction (e.g., magnetic dipole-dipole interaction, indirect dipole-dipole coupling), an electromagnetic interaction, adsorption, or any other useful interaction. For example, a particle may be coupled to a planar support via an electrostatic interaction. In another example, a particle may be coupled to a planar support via a magnetic interaction. In another example, a particle may be coupled to a planar support via a covalent interaction. Similarly, a nucleic acid molecule may be coupled to a particle via a covalent interaction. Alternatively or additionally, a nucleic acid molecule may be coupled to a particle via a non-covalent interaction. A coupling between a first object and a second object may comprise a labile moiety, such as an moiety comprising an ester, vicinal diol, phosphodiester, peptidic, glycosidic, sulfone, Diels-Alder, or similar linkage. The strength of a coupling between a first object and a second object may be indicated by a dissociation constant, $K_d$, which indicates the inclination of a coupled object comprising a first object and a second object to dissociate into the uncoupled first and second objects and may be expressed as a ratio of dissociated (e.g., uncoupled) objects to coupled objects. A smaller dissociation constant is generally indicative of a stronger coupling between coupled objects.

Coupled objects and their corresponding uncoupled components may exist in dynamic equilibrium with one another. For example, a solution comprising a plurality of coupled objects each comprising a first object and a second object may also include a plurality of first objects and a plurality of second objects. At a given point in time, a given first object and a given second object may be coupled to one another or the objects may be uncoupled; the relative concentrations of coupled and uncoupled components throughout the solution will depend upon the strength of the coupling between the first and second objects (reflected in the dissociation constant). For example, a binding moiety may be coupled to a nucleic acid molecule to provide a binding complex. In a solution comprising a plurality of binding complexes each comprising a binding moiety coupled to a nucleic acid molecule, the plurality of binding complexes may exist in equilibrium with their constituent nucleic acid molecules and binding moieties. The association between a given nucleic acid molecule and a given binding moiety may be such that, at a given point in time, at least 50%, such as at least 60%, 65%, 70%, 75%, 80%, 85%, 90%, 95%, 98%, or more, of the nucleic acid molecules may be components of a binding complex of the plurality of binding complexes.

The term "detector," as used herein, generally refers to a device that is capable of detecting a signal, including a signal indicative of the presence or absence of one or more incorporated nucleotides or fluorescent labels. The detector may simultaneously or substantially simultaneously detect multiple signals. The detector may detect the signal in real-time during, substantially during a biological reaction, such as a sequencing reaction (e.g., sequencing during a primer extension reaction), or subsequent to a biological reaction. In some cases, a detector can include optical and/or electronic components that can detect signals. Non-limiting examples of detection methods, for which a detector is used, include optical detection, spectroscopic detection, electrostatic detection, electrochemical detection, acoustic detection, magnetic detection, and the like. Optical detection methods include, but are not limited to, light absorption, ultraviolet-visible (UV-vis) light absorption, infrared light absorption, light scattering, Rayleigh scattering, Raman scattering, surface-enhanced Raman scattering, Mie scattering, fluorescence, luminescence, and phosphorescence. Spectroscopic detection methods include, but are not limited to, mass spectrometry, nuclear magnetic resonance (NMR) spectroscopy, and infrared spectroscopy. Electrostatic detection methods include, but are not limited to, gel-based techniques, such as, for example, gel electrophoresis. Electrochemical detection methods include, but are not limited to, electrochemical detection of amplified product after high-performance liquid chromatography separation of the amplified products. A detector may be a continuous area scanning detector. For example, the detector may comprise an imaging array sensor capable of continuous integration over a scanning area where the scanning is electronically synchronized to the image of an object in relative motion. A continuous area scanning detector may comprise a time delay and integration (TDI) charge coupled device (CCD), Hybrid TDI, complementary metal oxide semiconductor (CMOS) pseudo TDI device, or TDI line-scan camera.

The term "support" or "substrate," as used herein, generally refers to any solid or semi-solid article on which reagents such as nucleic acid molecules may be immobilized. Nucleic acid molecules may be synthesized, attached, ligated, or otherwise immobilized. Nucleic acid molecules may be immobilized on a substrate by any method including, but not limited to, physical adsorption, by ionic or covalent bond formation, or combinations thereof. A substrate may be 2-dimensional (e.g., a planar 2D substrate) or 3-dimensional. In some cases, a substrate may be a component of a flow cell and/or may be included within or adapted to be received by a sequencing instrument. A substrate may include a polymer, a glass, or a metallic material. Examples of substrates include a membrane, a planar substrate, a microtiter plate, a bead (e.g., a magnetic bead), a filter, a test strip, a slide, a cover slip, and a test tube. A substrate may comprise organic polymers such as polystyrene, polyethylene, polypropylene, polyfluoroethylene, polyethyleneoxy, and polyacrylamide (e.g., polyacrylamide gel), as well as co-polymers and grafts thereof. A substrate may comprise latex or dextran. A substrate may also be inorganic, such as glass, silica, gold, controlled-pore-glass (CPG), or reverse-phase silica. The configuration of a support may be, for example, in the form of beads, spheres, particles, granules, a gel, a porous matrix, or a substrate. In some cases, a substrate may be a single solid or semi-solid article (e.g., a single particle), while in other cases a substrate may comprise a plurality of solid or semi-solid articles (e.g., a collection of particles). Substrates may be planar, substantially planar, or non-planar. Substrates may be porous or non-porous and may have swelling or non-swelling characteristics. A substrate may be shaped to comprise one or more wells, depressions, or other containers, vessels, features, or locations. A plurality of substrates may be configured in an array at various locations. A substrate may be addressable (e.g., for robotic delivery of reagents), or by detection approaches, such as scanning by laser illumination and confocal or deflective light gathering. For example, a substrate may be in optical and/or physical communication with a detector. Alternatively, a substrate may be physically separated from a detector by a distance. An amplification substrate can be placed within or on another substrate, for example, where beads used as amplification substrates are disposed (e.g., immobilized) on a planar surface, or where beads used as amplification substrates are disposed (e.g., immobilized) inside of wells.

The term "bead," as described herein, generally refers to a solid support, resin, gel (e.g., hydrogel), colloid, or particle of any shape and dimensions. A bead may comprise any suitable material such as glass or ceramic, one or more polymers, and/or metals. Examples of suitable polymers include, but are not limited to, nylon, polytetrafluoroethylene, polystyrene, polyacrylamide, agarose, cellulose, cellulose derivatives, or dextran. Examples of suitable metals include paramagnetic metals, such as iron. A bead may be magnetic or non-magnetic. For example, a bead may comprise one or more polymers bearing one or more magnetic labels. A magnetic bead may be manipulated (e.g., moved between locations or physically constrained to a given location, e.g., of a reaction vessel such as a flow cell chamber) using electromagnetic forces. A bead may have one or more different dimensions including a diameter. A dimension of the bead (e.g., the diameter of the bead) may be less than about 1 mm, less than about 0.1 mm, less than about 0.01 mm, less than about 0.005 mm, from about 1 nm to about 100 nm, from about 1 μm to about 100 μm, or from about 1 mm to about 100 mm.

The term "adapter" as used herein, generally refers to a molecule (e.g., polynucleotide) that is adapted to permit a sequencing instrument to sequence a target polynucleotide, such as by interacting with a target nucleic acid molecule to facilitate sequencing (e.g., next generation sequencing (NGS)). The sequencing adapter may permit the target nucleic acid molecule to be sequenced by the sequencing instrument. For instance, the sequencing adapter may comprise a nucleotide sequence that hybridizes or binds to a capture polynucleotide attached to a solid support of a sequencing system, such as a bead or a flow cell. The sequencing adapter may comprise a nucleotide sequence that hybridizes or binds to a polynucleotide to generate a hairpin loop, which permits the target polynucleotide to be sequenced by a sequencing system. The sequencing adapter may include a sequencer motif, which may be a nucleotide sequence that is complementary to a flow cell sequence of another molecule (e.g., a polynucleotide) and usable by the sequencing system to sequence the target polynucleotide. The sequencer motif may also include a primer sequence for use in sequencing, such as sequencing by synthesis. The sequencer motif may include the sequence(s) for coupling a library adapter to a sequencing system and sequence the target polynucleotide (e.g., a sample nucleic acid). An adapter may have a first sub-part and a second sub-part. The first sub-part and the second sub-part may have sequence complementarity. An adapter as described herein may be a paired-end adapter useful for generating paired-end sequence reads.

The term "barcode" or "barcode sequence," as used herein, generally refers to one or more nucleotide sequences that may be used to identify one or more particular nucleic acids. A barcode may comprise at least 1, 2, 3, 4, 5, 6, 7, 8, 9, 10, 11, 12, 13, 14, 15, 16, 17, 18, 19, 20 or more nucleotides (e.g., consecutive nucleotides). A barcode may comprise at least about 10, about 20, about 30, about 40, about 50, about 60, about 70, about 80, about 90, about 100 or more consecutive nucleotides. All of the barcodes used for an amplification and/or sequencing process (e.g., NGS) may be different. The diversity of different barcodes in a population of nucleic acids comprising barcodes may be randomly generated or non-randomly generated.

A barcode may be comprised of one or more segments. For example, a barcode may comprise a first segment that has a first nucleic acid sequence and a second segment that has a second nucleic acid sequence. The first nucleic acid sequence may be the same or different than the second nucleic acid sequence. Barcode sequences comprising multiple segments may be assembled in a combinatorial fashion according to a split-pool scheme, in which a plurality of different first segments are distributed amongst a plurality of first partitions, the contents which are then pooled and distributed amongst a plurality of second partitions. A plurality of different second segments are then distributed amongst the plurality of second partitions and linked to the plurality of different first segments within the plurality of second partitions, and then the contents of the plurality of second partitions are pooled. The process may be repeated any number of times using any number of different segments and partitions to provide any level of barcode diversity. In some cases, the first segment of a barcode sequence may be coupled to a bead.

As described herein, the use of barcodes may permit high-throughput analysis of multiple samples using next generation sequencing techniques. Multiple samples or multiple portions of a sample may be barcoded. In an example, a sample comprising a plurality of nucleic acid molecules may be distributed throughout a plurality of partitions (e.g., droplets in an emulsion), where each partition comprises a nucleic acid barcode molecule comprising a unique barcode sequence. The sample may be partitioned such that all or a majority of the partitions of the plurality of partitions include at least one nucleic acid molecule of the plurality of nucleic acid molecules. A nucleic acid molecule and nucleic acid barcode molecule of a given partition may then be used to generate one or more copies and/or complements of at least a sequence of the nucleic acid molecule (e.g., via nucleic acid amplification reactions), which copies and/or complements comprise the barcode sequence of the nucleic acid barcode molecule or a complement thereof. The contents of the various partitions (e.g., amplification products or derivatives thereof) may then be pooled and subjected to sequencing. In some cases, nucleic acid barcode molecules may be coupled to beads. In such cases, the copies and/or complements may also be coupled to the beads. Nucleic acid barcode molecules, and copies and/or complements may be released from the beads within the partitions or after pooling to facilitate nucleic acid sequencing using a sequencing instrument. Because copies and/or complements of the nucleic acid molecules of the plurality of nucleic acid molecules each include a unique barcode sequence or complement thereof, sequencing reads obtained using a nucleic acid sequencing assay may be associated with the nucleic acid molecule of the plurality of nucleic acid molecules to which they correspond. This method may be applied to nucleic acid molecules included within cells divided amongst a plurality of partitions, and/or nucleic acid molecules deriving from a plurality of different samples. Alternatively, a sample comprising a plurality of nucleic acid molecules may be barcoded without the use of partitions. For example, different nucleic acid molecules may be immobilized to different beads within an open reaction space or bulk reaction mixture, wherein each bead comprises a different barcode sequence (e.g., unique bead species).

The methods described herein may be conducted in a reaction vessel (e.g., a droplet in an emulsion, or a well among a plurality of wells). Any suitable reaction vessel may be used. A reaction vessel may comprise a body that includes an interior surface, an exterior surface, and, in some cases, an open end and an opposing closed end. In some cases, a reaction vessel may not comprise an open or closed end. For example, a reaction vessel may be a droplet. In other cases, a reaction vessel may comprise a cap, which cap may be configured to contact the body at an open end, such that when contact is made the open end of the reaction vessel is closed. The cap may be permanently associated with the reaction vessel such that it remains attached to the reaction vessel in open and closed configurations. The cap may be removable, such that when the reaction vessel is open, the cap is separated from the reaction vessel. A reaction vessel such as a flow cell chamber (e.g., a flow cell chamber comprising a water-in-oil emulsion or a plurality of wells) may comprise one or more inlets or outlets, which inlets or outlets may be used to provide and remove reagents for use in a reaction. Reagents may be moved in and out of the chamber via pressure and vacuum controls. A reaction vessel as used herein may be sealed, optionally hermetically sealed (e.g., a sealed microwell plate).

A reaction vessel may be of varied size, shape, weight, and configuration. Some reaction vessels may be substantially round or oval tubular shaped. Some reaction vessels may be rectangular, square, diamond, circular, elliptical, or triangular shaped. A reaction vessel may be regularly shaped or irregularly shaped. For example, a reaction vessel that is a droplet (e.g., a droplet in an emulsion, such as an aqueous droplet) may be substantially spherical. A closed end of a reaction vessel (e.g., a well of a microwell plate or flow cell) may have a tapered, rounded, or flat surface. Non-limiting examples of types of a reaction vessel include a tube, a well, a capillary tube, a cartridge, a cuvette, a centrifuge tube, a droplet, or a pipette tip. Reaction vessels may be comprised of any suitable material with non-limiting examples of such materials that include glasses, metals, plastics, immiscible fluids, and combinations thereof. In an example, a reaction vessel may be a droplet, such as an aqueous droplet in an immiscible fluid such as an oil. A reaction vessel may be of any suitable size. For example, a reaction vessel may be an approximately spherical droplet having a diameter of at least about 1 nanometer (nm), 10 nm, 50 nm, 100 nm, 1 micron ($\mu$m), 10 $\mu$m, 50 $\mu$m, 100 $\mu$m, 1 millimeter (mm), 10 mm, 50 mm, 100 mm, or 1 centimeter (cm). Alternatively, a reaction vessel may be a well having a diameter of at least about 100 $\mu$m, 1 mm, 5 mm, or 10 mm. The depth of a well may be the same as or different than the diameter of the well. For example, the well may have a diameter of about 5 mm and a depth of about 10 mm.

A reaction vessel may be part of a collection or an array of reaction vessels. A collection or an array of reaction vessels may be particularly useful for automating methods and/or simultaneously processing multiple samples. A reaction vessel may be a well of a microwell plate comprised of a number of wells. A reaction vessel may be held in a well of a thermal block of a thermocycler, wherein the block of the thermal cycle comprises multiple wells each capable of receiving a sample vessel. A collection or an array comprised of reaction vessels (e.g., droplets or microwells) may comprise any appropriate number of reaction vessels. A collection or an array of reaction vessels may include at least 1, 2, 3, 4, 5, 6, 7, 8, 9, 10, 20, 30, 40, 50, 100, 200, 300, 400, 500, 1,000, 10,000 or more vessels. For example, a collection or an array of reaction vessels may comprise at least 2, 4, 6, 8, 10, 12, 14, 16, 18, 20, 25, 35, 48, 96, 144, 384, or more reaction vessels. A reaction vessel part of a collection or an array of reaction vessels (e.g., microwells) may also be individually addressable by a fluid handling device, such that the fluid handling device may correctly identify a reaction vessel and dispense appropriate fluid materials into the reaction vessel. Fluid handling devices may be useful in automating the addition of fluid materials to reaction vessels.

In some cases, one or more reaction vessels may be included within another reaction vessel. For example, a plurality of droplets may be included in a container such as a beaker, test tube, flow cell chamber, or other container, or a plurality of wells (e.g., of a microwell plate or flow cell) may be included in a container, such as a flow cell chamber. In an example, a plurality of wells may be provided on a surface of a flow cell chamber, such that a nucleic acid reaction may take place directly on a flow cell. In another example, one or more droplets may be physically constrained to a given area, such as a surface of a container. Droplets may be physically constrained via, for example, an electromagnetic force, such as via a magnetic attraction between a material (e.g., surface) of the container and a material included within the droplet (e.g., a paramagnetic bead or a magnetic label coupled to a bead) or via the use of optical tweezers. In an example, droplets may be constrained within wells (e.g., of a microwell plate or flow cell).

I. Sample Processing Workflow

The present disclosure provides methods for analyzing and/or processing a biological sample (e.g., biological sample or cell-free biological sample), in particular a nucleic acid sample comprising one or more template nucleic acid molecules. Systems and methods for processing a sample are also described in International Patent Pub. No. WO2022/040557, which is entirely incorporated herein by reference. Described herein are devices, systems, methods, compositions, and kits for processing samples, such as to prepare a sample for sequencing, to sequence a sample, and/or to analyze sequencing data. FIG. 1 illustrates an example sequencing workflow 100, according to the devices, systems, methods, compositions, and kits of the present disclosure.

Supports and/or template nucleic acids may be prepared and/or provided (101) to be compatible with downstream sequencing operations (e.g., 107). A support (e.g., bead) may be used to help facilitate sequencing of a template nucleic acid on a substrate. The support may help immobilize a template nucleic acid to a substrate, such as when the template nucleic acid is coupled to the support, and the support is in turn immobilized to the substrate. The support may further function as a binding entity to retain molecules of a colony of the template nucleic acid (e.g., copies comprising identical or substantially identical sequences as the template nucleic acid) together for any downstream processing, such as for sequencing operations. This may be particularly useful in distinguishing a colony from other colonies (e.g., on other supports) and generating amplified sequencing signals for a template nucleic acid sequence.

A support that is prepared and/or provided may comprise an oligonucleotide comprising one or more functional nucleic acid sequences. For example, the support may comprise a capture sequence configured to capture or be coupled to a template nucleic acid (or processed template nucleic acid). For example, the support may comprise the capture sequence, a primer sequence, a barcode sequence, a sample index sequence, a unique molecular identifier (UMI), a flow cell adapter sequence, an adapter sequence, a binding sequence for any molecule (e.g., splint, primer, template nucleic acid, capture sequence, etc.), or any other functional sequence useful for a downstream operation, or any combination thereof. The oligonucleotide may be single-stranded, double-stranded, or partially double-stranded.

A support may comprise one or more capture entities, where a capture entity is configured for capture by a capturing entity. A capture entity may be coupled to an oligonucleotide coupled to the support. A capture entity may be coupled to the support. For example, the capturing entity may comprise streptavidin (SA) when the capture moiety comprises biotin. In another example, the capturing entity may comprise a complementary capture sequence when the capture entity comprises a capture sequence (e.g., a capture oligonucleotide that is complementary to the complementary capture sequence). In another example, the capturing entity may comprise an apparatus, system, or device configured to apply a magnetic field when the capture entity comprises a magnetic particle. In another example, the capturing entity may comprise an apparatus, system, or device configured to apply an electrical field when the capture entity comprises a charged particle. In some instances, the capturing entity may comprise one or more other mechanisms configured to capture the capture entity. A capture entity and capturing entity may bind, couple, hybridize, or otherwise associate with each other. The association may comprise formation of a covalent bond, non-covalent bond, and/or releasable bond (e.g., cleavable bond that is cleavable upon application of a stimulus). In some cases, the association may not form any bond. For example, the association may increase a physical proximity (or decrease a physical distance) between the capturing entity and capture entity. In some instances, a single capture entity may be capable of associating with a single capturing entity. Alternatively, a single capture entity may be capable of associating with multiple capturing entities. Alternatively or in addition, a single capturing entity may be capable of associating with multiple capture entities. The capture entity may be capable of linking to a nucleotide. Chemically modified bases comprising biotin, an azide, cyclooctyne, tetrazole, and a thiol, and many others are suitable as capture entities. The capture entity/capturing entity pair may be any combination. The pair may include, but is not limited to, biotin/streptavidin, azide/cyclooctyne, and thiol/maleimide. It will be appreciated that either of the pair may be used as either the capture entity or the capturing entity. In some instances, the capturing entity may comprise a secondary capture entity, for example, for subsequent capture by a secondary capturing entity. The secondary capture entity and secondary capturing entity may comprise any one or more of the capturing mechanisms described elsewhere herein (e.g., biotin and streptavidin, complementary capture sequences, etc.). In some instances, the secondary capture entity can comprise a magnetic particle (e.g., magnetic bead) and the secondary capturing entity can comprise a magnetic system (e.g., magnet, apparatus, system, or device configured to apply a magnetic field, etc.). In some instances, the secondary capture entity can comprise a charged particle (e.g., charged bead carrying an electrical charge) and the secondary capturing entity can comprise an electrical system (e.g., magnet, apparatus, system, or device configured to apply an electric field, etc.).

A support may comprise one or more cleaving moieties. The cleavable moiety may be part of or attached to an oligonucleotide coupled to the support. The cleavable moiety may be coupled to the support. A cleavable moiety may comprise any useful cleavable or excisable moiety that can be used to cleave an oligonucleotide (or portion thereof) from the support. For example, the cleavable moiety may comprise a uracil, a ribonucleotide, or other modified nucleotide that is excisable or cleavable using an enzyme (e.g., UDG, RNAse, endonuclease, exonuclease, etc.). The cleavable moiety may comprise an abasic site or an analog of an abasic site (e.g., dSpacer), a dideoxyribose. The cleavable moiety may comprise a spacer, e.g., C3 spacer, hexanediol, triethylene glycol spacer (e.g., Spacer 9), hexaethyleneglycol spacer (e.g., Spacer 18), or combinations or analogs thereof. The cleavable moiety may comprise a photocleavable moiety. The cleavable moiety may comprise a modified nucleotide, e.g., a methylated nucleotide. The modified nucleotide may be recognized specifically by an enzyme (e.g., a methylated nucleotide may be recognized by MspJI). The cleavable moiety may be cleaved enzymatically (e.g., using an enzyme such as UDG, RNAse, APE1, MspJI, etc.). Alternatively, or in addition to, the cleavable moiety may be cleavable using one or more stimuli, e.g., photostimulus, chemical stimulus, thermal stimulus, etc.

In some examples, a single support comprises copies of a single species of oligonucleotide, which are identical or substantially identical to each other. In some examples, a single support comprises copies of at least two species of oligonucleotides (e.g., comprising different sequences). For example, a single support may comprise a first subset of oligonucleotides configured to capture a first adapter sequence of a template nucleic acid and a second subset of oligonucleotides configured to capture a second adapter sequence of a template nucleic acid.

In some examples, a population of a single species of supports may be prepared and/or provided, where all supports within a species of supports is identical (e.g., has identical oligonucleotide composition (e.g., sequence), etc.). In some examples, a population of multiple species of supports may be prepared and/or provided. For example, a population of supports may be prepared to comprise a plurality of unique support species, where each unique support species comprises a primer sequence unique to said support species. When attaching template nucleic acids to supports, only a template nucleic acid comprising a given adapter sequence compatible with (e.g., at least partially complementary to) a given primer sequence may be capable of attaching to a given support of a support species comprising the given primer sequence. In another example, a population of supports may be prepared, such that each unique support species comprises a plurality of primer sequences (e.g., a pair of primer sequences) unique to said support species. In some embodiments, the systems and methods disclosed herein can include a population of supports that comprise two, three, four, five, six, seven, eight, nine, ten or more unique support species. Each unique support species can comprise a unique primer sequence that allows selective interactions between the respective support species with an intended binding partner (e.g., a complementary nucleic acid sequence within an adapter region of a template nucleic acid or an intermediary primer sequence which can subsequently bind to a complementary nucleic acid sequence within an adapter region of a sample nucleic acid). A population of multiple species of supports may be prepared by first preparing distinct populations of a single species of supports, all different, and mixing such distinct populations of single species of supports to result in the final population of multiple species of supports. A concentration of the different support species within the final mixture may be adjusted accordingly. Devices, systems, methods, compositions, and kits for preparing and using support species are described in further detail in U.S. Patent Pub. No. 2022/0042072A1 and International Patent Pub. No. WO2022040557A2, each of which is entirely incorporated herein by reference for all purposes.

A template nucleic acid may include an insert sequence sourced from a biological sample. In some cases, the insert sequence may be derived from a larger nucleic acid in the biological sample (e.g., an endogenous nucleic acid), or reverse complement thereof, for example by fragmenting, transposing, and/or replicating from the larger nucleic acid. The template nucleic acid may be derived from any nucleic acid of the biological sample and result from any number of nucleic acid processing operations, such as but not limited to fragmentation, degradation or digestion, transposition, ligation, reverse transcription, extension, etc. A template nucleic acid that is prepared and/or provided may comprise one or more functional nucleic acid sequences. In some cases, the one or more functional nucleic acid sequences may be disposed at one end of the insert sequence. In some cases, the one or more functional nucleic acid sequences may be separated and disposed at both ends of an insert sequence, such as to sandwich the insert sequence. In some cases, a nucleic acid molecule comprising the insert sequence, or complement thereof, may be ligated to one or more adapter oligonucleotides that comprise such functional nucleic acid sequence(s). In some cases, a nucleic acid molecule comprising the insert sequence, or complement thereof, may be hybridized to a primer comprising such functional nucleic acid sequence(s) and extended to generate a template nucleic acid comprising such functional nucleic acid sequence(s). In some cases, a nucleic acid molecule comprising the insert sequence, or complement thereof, may be hybridized to a primer comprising one or more functional nucleic acid sequence(s) and extended to generate an intermediary molecule, and the intermediary molecule hybridized to a primer comprising additional functional nucleic acid sequence(s) and extended, and so on for any number of extension reactions, to generate a template nucleic acid comprising one or more functional nucleic acid sequence(s). For example, the template nucleic acid may comprise an adapter sequence configured to be captured by a capture sequence on an oligonucleotide coupled to a support. For example, the template nucleic acid may comprise a capture sequence, a primer sequence, a barcode sequence, a sample index sequence, a unique molecular identifier (UMI), a flow cell adapter sequence, the adapter sequence, a binding sequence for any molecule (e.g., splint, primer, template nucleic acid, capture sequence, etc.), or any other functional sequence useful for a downstream operation, or any combination thereof. The template nucleic acid may be single-stranded, double-stranded, or partially double-stranded.

A template nucleic acid may comprise one or more capture entities that are described elsewhere herein. In some cases, in the workflow, only the supports comprise capture entities and the template nucleic acids do not comprise capture entities. In other cases, in the workflow, only the template nucleic acids comprise capture entities and the supports do not comprise capture entities. In other cases, both the template nucleic acids and the supports comprise capture entities. In other cases, neither the supports nor the template nucleic acids comprise capture entities.

A template nucleic acid may comprise one or more cleaving moieties that are described elsewhere herein. In some cases, in the workflow, only the supports comprise cleavable moieties and the template nucleic acids do not comprise cleavable moieties. In other cases, in the workflow, only the template nucleic acids comprise cleavable moieties and the supports do not comprise cleavable moieties. In other cases, both the template nucleic acids and the supports comprise cleavable moieties. In other cases, neither the supports nor the template nucleic acids comprise cleavable moieties. A cleavable moiety may be strategically placed based on a desired downstream amplification workflow, for example.

In some examples, a library of insert sequences are processed to provide a population of template sequences with identical configurations, such as with identical sequences and/or locations of one or more functional sequences. For example, a population of template sequences may comprise a plurality of nucleic acid molecules each comprising an identical first adapter sequence ligated to a same end. In some examples, a library of insert sequences are processed to provide a population of template sequences with varying configurations, such as with varying sequences and/or locations of one or more functional sequences. For example, a population of template sequences may comprise a first subset of nucleic acid molecules each comprising an identical first adapter sequence at a first end, and a second subset of nucleic acid molecules each comprising an identical second adapter sequence at the second end, where the second adapter sequence is different form the first adapter sequence. In some instances, a population of template sequences with varying configurations (e.g., varying adapter sequences) may be used in conjunction with a population of multiple species of supports, such as to reduce polyclonality problems during downstream amplification. A population of multiple configurations of template nucleic acids may be prepared by first preparing distinct populations of a single configuration of template nucleic acids, all different, and mixing such distinct populations of single configurations of template nucleic acids to result in the final population of multiple configurations of template nucleic acids. A concentration of the different configurations of template nucleic acids within the final mixture may be adjusted accordingly.

Optionally, the supports and/or template nucleic acids may be pre-enriched (102). For example, a support comprising a distinct oligonucleotide sequence is isolated from a mixture comprising support(s) that do not have the distinct oligonucleotide sequence. Alternatively, a support population may be provided to comprise substantially uniform supports, where each support comprises an identical surface primer molecule immobilized thereto. For example, template nucleic acids comprising a distinct configuration (e.g., comprising a particular adapter sequence) is isolated from a mixture comprising template nucleic acids that do not have the distinct configuration. Alternatively, a template nucleic acid population may be provided to comprise substantially uniform configurations. In some cases, the capture entit(ies) on the supports and/or template nucleic acids are used for pre-enrichment.

Subsequent to preparation of the supports and template nucleic acids, the two may be attached (103). A template nucleic acid may be coupled to a support via any method(s) that results in a stable association between the template nucleic acid and the support. For example, the template nucleic acid may hybridize to an oligonucleotide on the support. In another example, the template nucleic acid may hybridize to one or more intermediary molecules, such as a splint, bridge, and/or primer molecule, which hybridizes to an oligonucleotide on the support. Alternatively or in addition, a template nucleic acid may be ligated to one or more nucleic acids on or coupled to the support. Alternatively or in addition, a template nucleic acid may be hybridized to an oligonucleotide on a support, which oligonucleotide comprises a primer sequence, and subsequent extension form the primer sequence is performed. Once attached, a plurality of support-template complexes may be generated.

Optionally, support-template complexes may be pre-enriched (104), wherein a support-template complex is isolated from a mixture comprising support(s) and/or template nucleic acid(s) that are not attached to each other. In some cases, the capture entit(ies) on the supports and/or template nucleic acids are used for pre-enrichment.

Subsequent to attachment of the template nucleic acid molecule to the support, the template nucleic acids may be subjected to amplification reactions (105) to generate a plurality of amplification products immobilized to the support. For example, such amplification reactions may comprise performing polymerase chain reaction (PCR) or any other amplification methods described herein, including but not limited to emulsion PCR (ePCR or emPCR), isothermal amplification (e.g., recombinase polymerase amplification (RPA)), bridge amplification, template walking, etc. In some cases, amplification reactions can occur while the support is immobilized to a substrate. In other cases, amplification reactions can occur off the substrate, such as in solution, or on a different surface or platform. In some cases, amplification reactions can occur in isolated reaction volumes, such as within multiple droplets in an emulsion during emulsion PCR (ePCR or emPCR), or in wells. Emulsion PCR methods are described in further detail in U.S. Patent Pub. No. 20220042072A1 and International Patent Pub. No. WO2022040557A2, each of which is entirely incorporated by reference herein.

Subsequent to amplification, the supports (e.g., comprising the template nucleic acids) may be subjected to post-amplification processing (106). Often, subsequent to amplification, a resulting mixture may comprise a mix of positive supports (e.g., those comprising a template nucleic acid molecule) and negative supports (e.g., those not attached to template nucleic acid molecules). Enrichment procedure(s) may isolate positive supports from the mixtures. Example methods of enrichment of amplified supports are described in U.S. Pat. Nos. 10,900,078, U.S. Patent Pub. No. 20210079464A1, and International Patent Pub. No. WO2022040557A2, each of which is entirely incorporated by reference herein. For example, an on-substrate enrichment procedure may immobilize only the positive supports onto the substrate surface to isolate the positive supports. In some instances, the positive supports may be immobilized to desired locations on the substrate surface (e.g., individually addressable locations), as distinguished from undesired locations (e.g., spacers between the individually addressable locations). In some instances, positive supports and/or negative supports may be processed to selectively remove unamplified surface primers (on the support(s)), such that a resulting positive support retains the template nucleic acid molecule, and a resulting negative support is stripped of the unamplified surface primers. Subsequently, the template nucleic acid(s) on the positive supports may be used to enrich for the positive supports, e.g., by capturing the template nucleic acids.

Subsequent to post-amplification processing, the template nucleic acids may be subject to sequencing (107). The template nucleic acid(s) may be sequenced while attached to the support. Alternatively, the template nucleic acid molecules may be free of the support when sequenced and/or analyzed. In some instances, the template nucleic acids may be sequenced while attached to the support which is immobilized to a substrate. Examples of substrate-based sample processing systems are described elsewhere herein. Any sequencing method described elsewhere herein may be used. In some cases, sequencing by synthesis (SBS) is performed.

In one example (Example A), an SBS method comprises flowing nucleotide reagents according to a flow order comprising a repeat of one 4-base flow (e.g., [A/T/G/C]), where each nucleotide is reversibly terminated (e.g., dideoxynucleotide), and where each base is labeled with a different dye (yielding different optical signals). With each flow, other sequencing reagents, e.g., sequencing primer, polymerase, buffer, etc. are present to provide sufficient conditions for incorporation of the reversibly terminated, labeled nucleotide into a growing strand hybridized to a template nucleic acid. After each flow, an incorporation event or lack thereof of each base can be detected by interrogating the different dyes in 4 channels. After the incorporation events of a flow, in which at most one nucleotide is incorporated into each growing strand due to the terminated state, the termination can be reversed (e.g., cleaving a terminating moiety) to allow for subsequent stepwise incorporation events in subsequent flows. After each or one or more detection events, the labels may be removed (e.g., cleaved) to reduce signal noise for the next detection. In another example (Example B), an SBS method comprises flowing nucleotide reagents according to a flow order comprising a repeat of a flow cycle of 4 single base flows (e.g., [A T G C]), where each nucleotide is reversibly terminated, and where each base is labeled with a same dye (yielding same frequency optical signals). With each flow, other sequencing reagents, e.g., sequencing primer, polymerase, buffer, etc. are present to provide sufficient conditions for incorporation of the reversibly terminated, labeled nucleotide into a growing strand hybridized to a template nucleic acid. After each flow, an incorporation event or lack thereof of the particular base in that flow can be detected by interrogating the wavelength of the dye. After the incorporation events of a flow, in which at most one nucleotide is incorporated into each growing strand due to the terminated state, the termination can be reversed (e.g., cleaving a terminating moiety) to allow for subsequent stepwise incorporation events in subsequent flows. After each or one or more detection events, the labels may be removed (e.g., cleaved) to reduce signal noise for the next detection. In another example (Example C), an SBS method comprises flowing nucleotide reagents according to a flow order comprising a repeat of a flow cycle of 4 single base flows (e.g., [A T G C]), where each nucleotide is not terminated, and where each base is labeled with a same dye (yielding same frequency optical signals). With each flow, other sequencing reagents, e.g., sequencing primer, polymerase, buffer, etc. are present to provide sufficient conditions for incorporation of the labeled nucleotide into a growing strand hybridized to a template nucleic acid. After each flow, an incorporation event or lack thereof of the particular base in that flow can be detected by interrogating the wavelength of the dye. Because the nucleotides are not terminated, if the growing strand is extending through a homopolymer region (e.g., polyT region, etc.) of the template nucleic acid, multiple nucleotides may be incorporated during one flow. After each or one or more detection events, the labels may be removed (e.g., dyes are cleaved) to reduce signal noise for the next detection. In another example (Example D), an SBS method comprises flowing nucleotide reagents according to a flow order comprising a repeat of a flow cycle of 4 single base flows (e.g., [A T G C]), where each nucleotide is not terminated, and where only a fraction of the bases in each flow (e.g., less than 90%, 80%, 70%, 60%, 50%, 40%, 30%, 20%, 10%, 9%, 8%, 7%, 6%, 5%, 4%, 3%, 2%, 1%, etc.) is labeled with a same dye (yielding same frequency optical signals). With each flow, other sequencing reagents, e.g., sequencing primer, polymerase, buffer, etc. are present to provide sufficient conditions for incorporation of the nucleotide into a growing strand hybridized to a template nucleic acid. After each flow, an incorporation event or lack thereof of the particular base in that flow can be detected by interrogating the wavelength of the dye. Because the nucleotides are not terminated, if the growing strand is extending through a homopolymer region (e.g., polyT region, etc.) of the template nucleic acid, multiple nucleotides may be incorporated during one flow. After each or one or more detection events, the labels may be removed (e.g., dyes are cleaved) to reduce signal noise for the next detection. In another example (Example E), an SBS method comprises flowing nucleotide reagents according to a flow order comprising a repeat of a flow cycle of 8 single base flows, with each of the 4 canonical base types flowed twice consecutively within the flow cycle, (e.g., [A A T T G G C C]), where each nucleotide is not terminated, and where only a fraction of the bases in every other flow in the flow cycle (e.g., less than 90%, 80%, 70%, 60%, 50%, 40%, 30%, 20%, 10%, 9%, 8%, 7%, 6%, 5%, 4%, 3%, 2%, 1%, etc.) is labeled with a same dye (yielding same frequency optical signals) and the nucleotides in the alternating other flow is unlabeled. With each flow, other sequencing reagents, e.g., sequencing primer, polymerase, buffer, etc. are present to provide sufficient conditions for incorporation of the nucleotide into a growing strand hybridized to a template nucleic acid. After one or both of the flows for each canonical base type, an incorporation event or lack thereof of the particular base in that flow can be detected by interrogating the wavelength of the dye. Because the nucleotides are not terminated, if the growing strand is extending through a homopolymer region (e.g., polyT region) of the template nucleic acid, multiple nucleotides may be incorporated during one flow. A first flow of a canonical base type (e.g., A) followed by a second flow of the same canonical base type (e.g., A) may help facilitate completion of incorporation reactions across each growing strand such as to reduce phasing problems. After each or one or more detection events, the labels may be removed (e.g., dyes are cleaved) to reduce signal noise for the next detection.

Labeled nucleotides may comprise a dye, fluorophore, or quantum dot. Non-limiting examples of dyes include SYBR green, SYBR blue, DAPI, propidium iodine, Hoechst, SYBR gold, ethidium bromide, acridine, proflavine, acridine orange, acriflavine, fluorocoumarin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5-(or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, Atto 390, 425, 465, 488, 495, 532, 565, 594, 633, 647, 647N, 665, 680 and 700 dyes, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores, Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare); Dy-Quenchers (Dyomics), such as DYQ-660 and DYQ-661; and ATTO fluorescent quenchers (ATTO-TEC GmbH), such as ATTO 540Q, 580Q, 612Q, 532, and 633, or other fluorophores and quenchers. In some cases, the label may be one with linkers. For instance, a label may have a disulfide linker attached to the label. Non-limiting examples of such labels include Cy5-azide, Cy-2-azide, Cy-3-azide, Cy-3.5-azide, Cy5.5-azide and Cy-7-azide. In some cases, a linker may be a cleavable linker. In some cases, the label may be a type that does not self-quench or exhibit proximity quenching. Non-limiting examples of a label type that does not self-quench or exhibit proximity quenching include Bimane derivatives such as Monobromobimane. Alternatively, the label may be a type that self-quenches or exhibits proximity quenching. Non-limiting examples of such labels include Cy5-azide, Cy-2-azide, Cy-3-azide, Cy-3.5-azide, Cy5.5-azide and Cy-7-azide. In some instances, a blocking group of a reversible terminator may comprise the dye.

It will be appreciated that the combinations of termination states on the nucleotides, label types (e.g., types of dye or other detectable moiety), fraction of labeled nucleotides within a flow, type of nucleotide bases in each flow, type of nucleotide bases in each flow cycle, and/or the order of flows in a flow cycle and/or flow order, other than enumerated in Examples A-E, can be varied for different SBS methods.

Subsequent to sequencing, the sequencing signals collected and/or generated may be subjected to data analysis (108). The sequencing signals may be processed to generate base calls and/or sequencing reads. In some cases, the sequencing signals may be processed to filter out low quality and/or low confidence base calls and/or sequencing reads. In some cases, the sequencing reads may be processed to generate diagnostics data to the biological sample, or the subject from which the biological sample was derived from.

While the sequencing workflow 100 with respect to FIG. 1 has been described with respect to the use of supports to bind template molecules, it will be appreciated that the different supports may be effectively replaced by using spatially distinct locations on one or more surfaces, which do not necessarily have to be the surfaces of individual supports (e.g., beads). For example, a first spatially distinct location on a surface may be capable of directly immobilizing a first colony of a first template nucleic acid and a second spatially distinct location on the same surface (or a different surface) may be capable of directly immobilizing a second colony of a second template nucleic acid to distinguish from the first colony. In some cases, the surface comprising the spatially distinct locations may be a surface of the substrate on which the sample is sequenced, thus streamlining the amplification-sequencing workflow.

It will be appreciated that in some instances, the different operations described in the sequencing workflow 100 may be performed in a different order. It will be appreciated that in some instances, one or more operations described in the sequencing workflow 100 may be omitted or replaced with other comparable operation(s). It will be appreciated that in some instances, one or more additional operations described in the sequencing workflow 100 may be performed.

The different operations described with respect to sequencing workflow 100 may be performed with the help of open substrate systems described herein.

II. Pre-Enrichment and Adapter Attachment

Figure 2A:
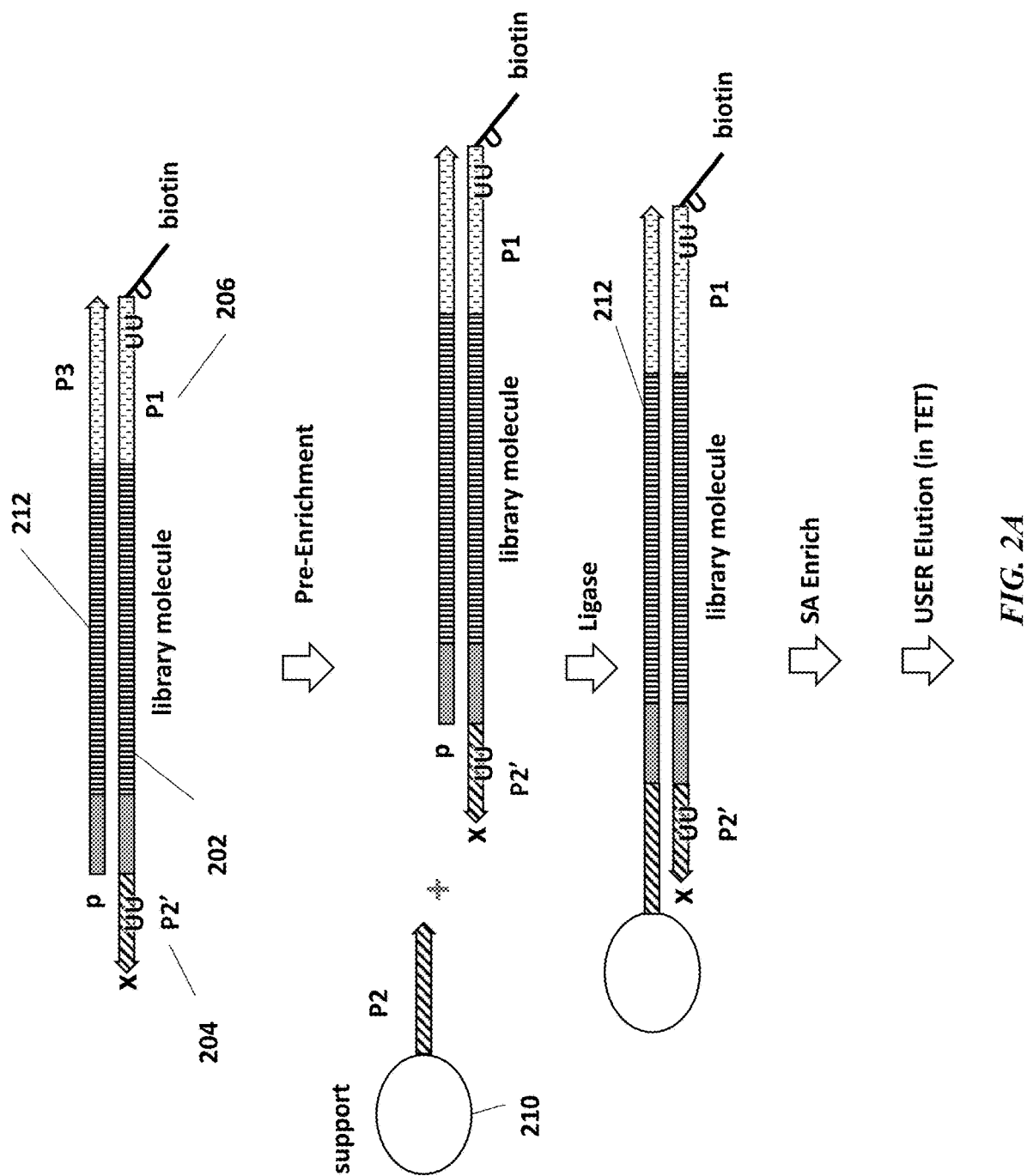
FIGS. 2A-2D illustrate example workflows for pre-enrichment of template nucleic acid molecules, in accordance with some embodiments of the present disclosure.
Figure 2B:
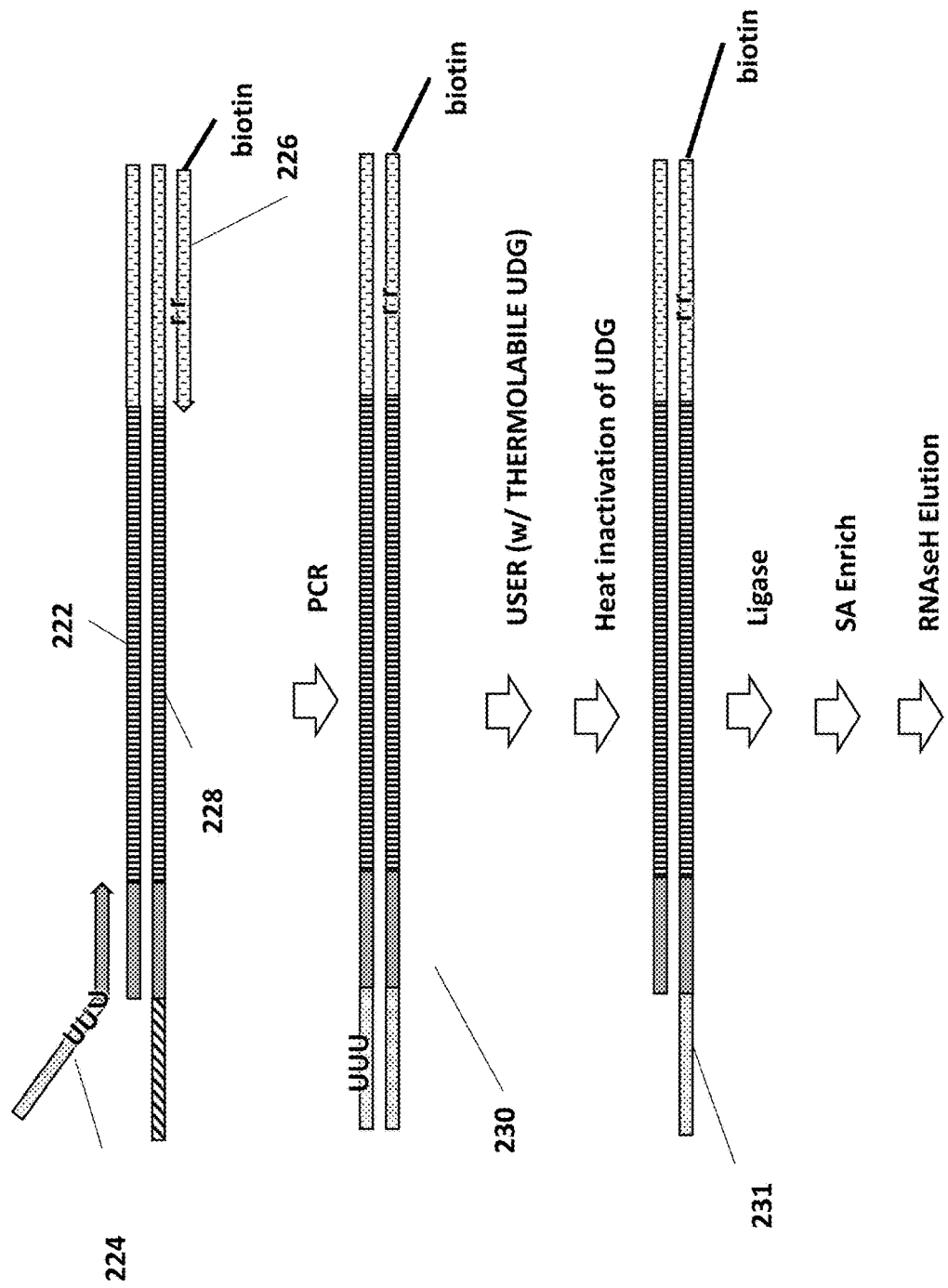
Figure 2C:
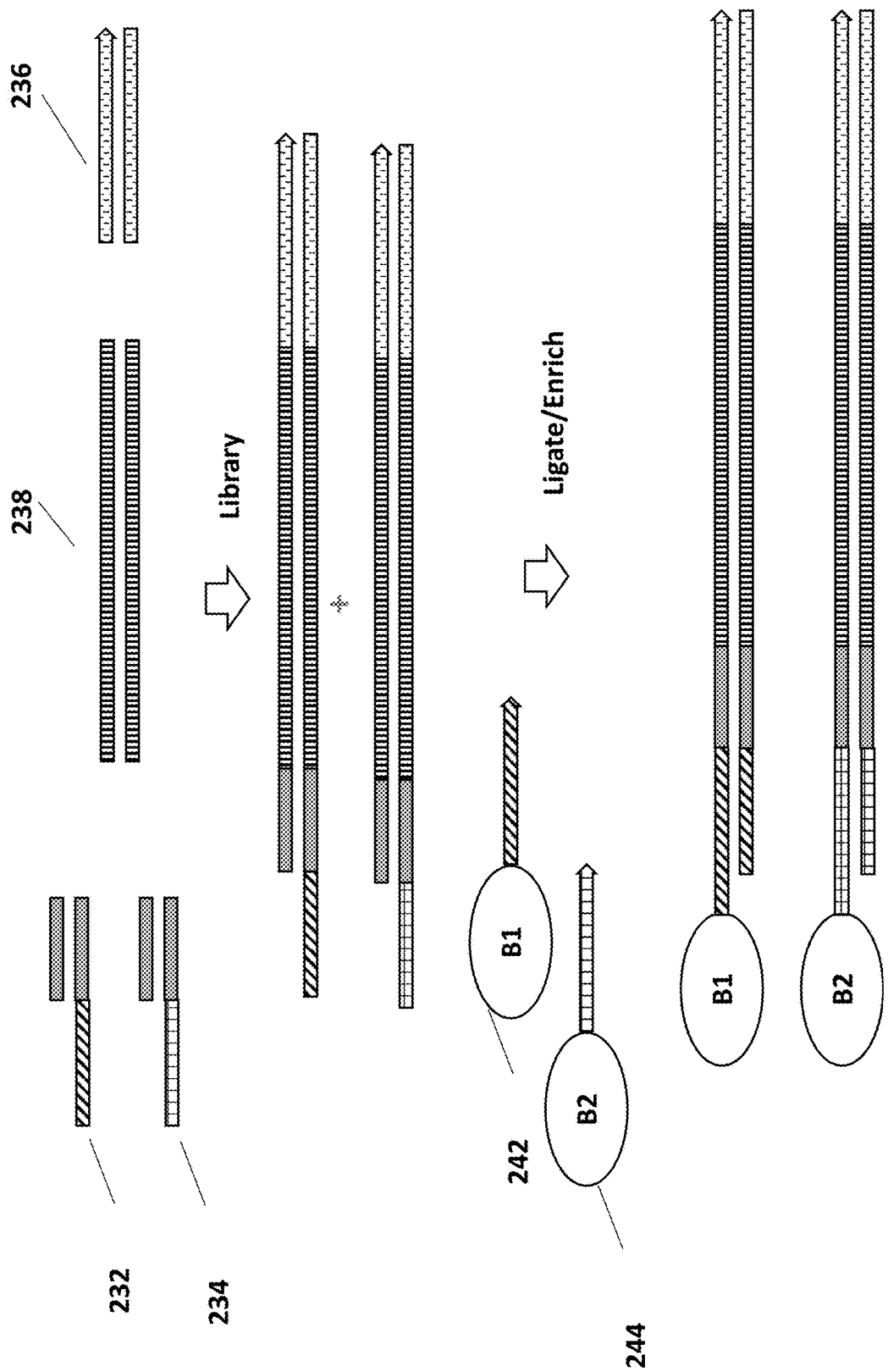
Figure 2D:
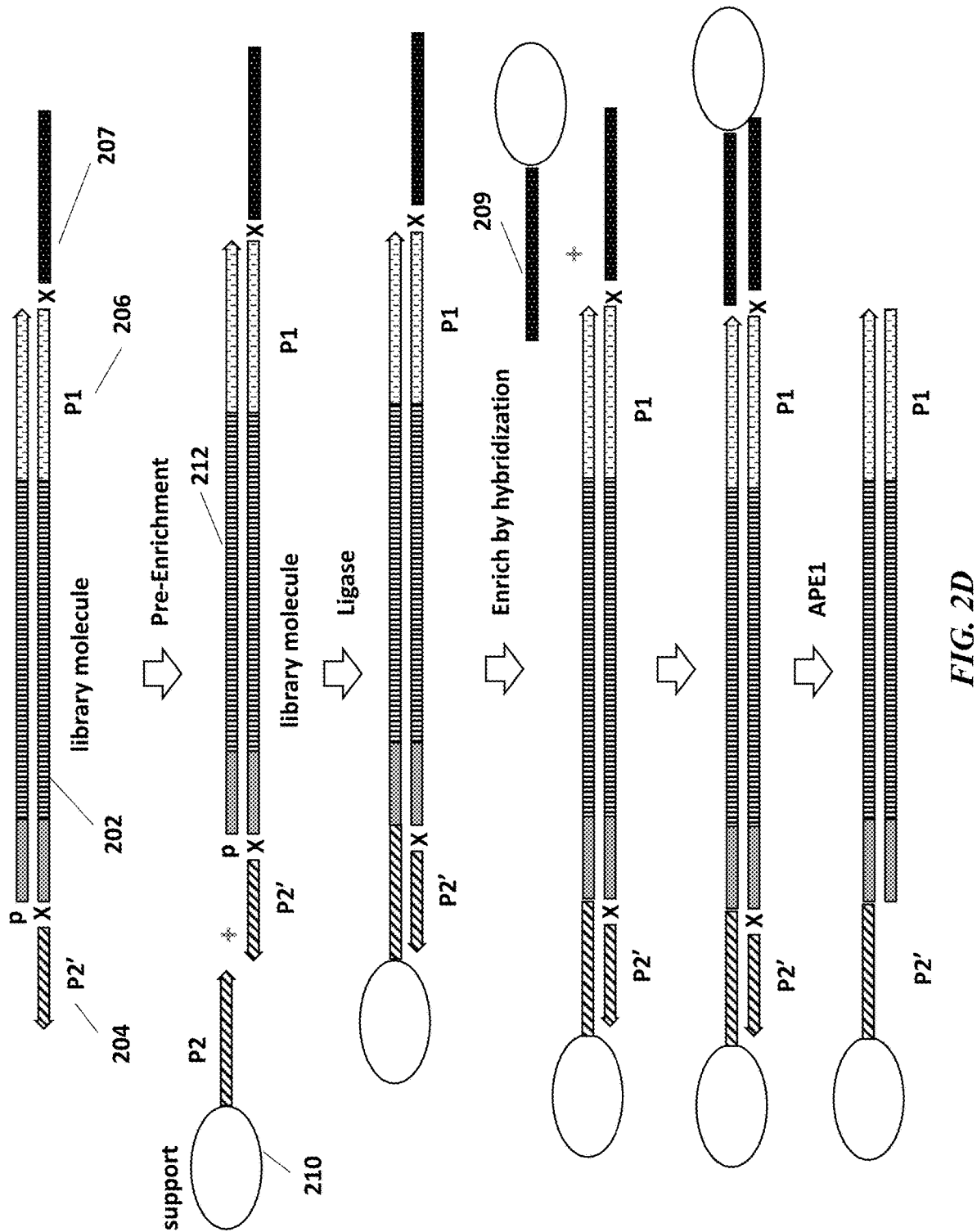

FIGS. 2A-2D show examples of pre-enrichment (e.g., 102, 104) schemes that can be used in combination with one or more of the other methods described herein. As illustrated in FIG. 1, pre-enrichment (102, 104) can occur prior to amplification and sequencing. FIG. 2A illustrates an example where adapters including one or more cleavable moieties (e.g., a uracil or a ribonucleotide) are used. FIG. 2B illustrates an example where adapters comprising one or more cleavable moieties of different types (e.g., a uracil and a ribonucleic acid) are used. FIG. 2C illustrates an example where different support species having surface primer sequences complementary to different adapter sequences can be used to bind to template nucleic acid molecules to decrease the possibility of different template nucleic acid molecules binding to the same support. FIG. 2D illustrates an alternative pre-enrichment process where pre-enrichment occurs via hybridization of complementary sequences.

As shown in FIG. 2A, in some embodiments, a double-stranded template nucleic acid molecule (e.g., of a library of template nucleic acid molecules) comprises, ligated at each end, an adapter containing one or more cleavable moieties (e.g. uracils). The methods for pre-enrichment described herein may comprise generating such double-stranded template nucleic acid molecules. The double-stranded template nucleic acid molecule may comprise a template sequence. The double-stranded template nucleic acid molecule may comprise different sequences at the 5' and 3' ends. For example, the 5' and 3' ends of a first strand (e.g., strand 202) of the double-stranded template nucleic acid molecule may comprise different overhang sequences. In this example, each of the 5' and 3' ends comprises an adapter with a plurality of uracils. In some embodiments, one adapter containing one or more cleavable moieties (e.g., uracils) may be on a first strand (e.g., a top strand) and another adapter containing one or more cleavable moieties (e.g., uracils) may be on a second strand (e.g., a bottom strand) of the double-stranded template nucleic acid molecule (e.g., both adapters may be on 5' ends or both may be on 3' ends). On the 5' end of the first strand 202, sequence P1 (e.g., sequence 206) comprises an overhang comprising one or more uracils, where the overhang is connected to a biotin molecule (e.g., the 5' end of first strand is biotinylated). On the 3' end of the first strand 202, sequence P2' (e.g., sequence 204) comprises an overhang sequence including one or more cleavable moieties (e.g., a uracil or a ribonucleotide). In some embodiments, as described for example below, other cleavable sequences (comprising one or more cleavable moieties) can be used at either of both of the 3' and 5' ends of the first strand 202 (e.g., in place of the pluralities of uracils in sequence 204 and sequence 206). The sequence P2' is at least partially complementary to a sequence P2 bound to support 210, such as a bead. In some embodiments, the biotin molecule instead of being connected to the first strand at the 5' end, may be connected to a second strand of the double-stranded template nucleic acid molecule (e.g., at the 3' end via sequence P3, modified with a cleavable sequence). Optionally, a polymerase (e.g., Taq polymerase or another polymerase with 5'-3' exonuclease activity) and reaction reagents (e.g., nucleotide bases) may be used to process the double-stranded template nucleic acid molecule, e.g., to facilitate hybridization or ligation of the double-stranded template nucleic acid molecule to the support 210. For example, the polymerase may cleave off any remaining uncleaved moieties (e.g., ribonucleotides, uracil), generating a phosphorylated end (e.g., phosphorylated 5' end) of the template nucleic acid molecules. After the template nucleic acid molecule hybridizes to support 210, a ligase is used to repair the nick such that the second strand 2212 is covalently attached to support 210. An advantage of this uracil-based protocol is that, after enrichment, the nucleic acid molecule fragment (e.g., second strand 212) bound to support 210, such as a bead, is the original fragment. Thus, for example, one fewer PCR amplification step is required, thus reducing the potential for introducing sequencing errors. In addition to one or more cleavable moieties, sequence 206 can further comprises an affinity tag such as a biotin. The affinity tag may comprise any appropriate capture moiety, configured for capture by a capturing moiety, as described elsewhere herein. After strand 212 is covalently linked to support 210, magnetic beads each comprising a capturing moiety (e.g., streptavidin) may be introduced to a reaction mixture containing numerous supports (some of which are covalently linked with template nucleic acid molecules and some of which are not). Supports covalently linked to a template nucleic acid molecule may have the affinity tag (e.g., a biotin tag) that binds to the capturing moiety (e.g., streptavidin), and therefore can be selectively pulled down or otherwise isolated using the magnetic beads comprising the capturing moiety, such as via applying a magnetic field. As a result, the supports comprising the respective template nucleic acid molecules coupled thereto (e.g., covalently linked thereto) may be isolated and enriched from the other supports that do not have a template nucleic acid molecule attached. USER (Uracil-Specific Excision Reagent) enzymes can then be added to the reaction mixture to cleave off the uracils that are 3' to the biotin tag before the bead-template nucleic acid complexes are further processed (e.g., amplified and sequenced).

As shown in FIG. 2B, in some embodiments, template nucleic acid molecules are already attached to adapters that may not be compatible with a pre-enrichment scheme as disclosed herein. A template nucleic acid molecule may be generated from a duplex template molecule using a combination of primers comprising different cleavable moieties (e.g., a uracil-containing primer and a ribonucleic acid-containing primer). For example, a first primer (e.g., primer 224) that is complementary to a first strand 222 of the duplex template molecule comprises a plurality of uracils (e.g., a uracil-based cleavage point). A second primer (e.g., primer 226) that is complementary to second strand 228 comprises a plurality of ribonucleic acid bases. A PCR amplification operation is performed to generate a double-stranded intermediate template nucleic acid molecule 230. An enzyme (e.g., USER with a thermolabile UDG: uracil DNA glycosylase) may then be used to cleave the one or more cleavable moieties (e.g., a uracil) in the sequence corresponding to the first primer 224. After the enzyme treatment, a 3' overhang 231 is generated which can then bind to a complementary sequence on a support, as described elsewhere herein. Optionally, a polymerase (e.g., Taq polymerase) and reaction reagents (e.g., nucleotide bases) may be used to process the double-stranded template nucleic acid molecule, e.g., to facilitate hybridization or downstream ligation of the double-stranded template nucleic acid molecule to the support 210. Similarly, a ligase can be added to covalently attach the first strand 222 to the support. The reaction mixture can then be processed as described above with respect to FIG. 2A.

FIG. 2C illustrates that, in some embodiments, double-stranded template nucleic acid molecules (e.g., from a library of template nucleic acid molecules) can be ligated to supports (e.g., beads) having different surface primers attached thereon (e.g., a population of different bead species with at least 2 different surface primer sequences, at least 3 different surface primer sequences, at least 5 different surface primer sequences, etc.). FIG. 2C shows annealing of template nucleic acid molecules to two bead species with two different surface primer sequences (e.g., bead species 242 and 244). Similar to the protocol presented in FIG. 2A, double-stranded template molecules (e.g., 238) may each be ligated to a different adapter at each end. For example, provided a population of initial template molecules (238), a first adapter 236 (e.g., barcoded adapter) can be added at one end and a mixture of two different types of second adapters (e.g., adapters 232 and 234) can be added and ligated to the other end of the template molecules 238. The second adapters may comprise 5' bead adapter primers. The ligation of the second adapters may occur prior to, during, or after the ligation of the first adapters. The mixture of second adapters may comprise adapters with different sequences. The mixture of second adapters may be in equimolar concentrations of the adapters with different sequences. Alternatively, the mixture of second adapters may be in any other concentrations (e.g., engineered for the subsequent operations). Alternatively or in addition, a sample comprising the template molecules 238 are divided in two portions and the two different second adapters (232 and 234) can be ligated to the template molecules in separate reactions (e.g., in separate reaction spaces). In some embodiments, one or more of the adapters (e.g., 232, 234, and 236) can include a barcode sequence. The resulting template nucleic acid molecules can selectively bind to supports (e.g., beads) comprising sequences that are complementary to the overhang sequences in adapter 232 or 234. This permits the ligation of different support species (e.g., bead 242 and bead 244) to different populations of template molecules in the library, thus permitting different types of downstream analysis. Though not illustrated in FIG. 2C, enrichment schemes as disclosed in FIGS. 2A and 2B can be used for the template nucleic acid molecules generated in accordance with FIG. 2C. For example, one or more uracils and an affinity tag (e.g., streptavidin) can be included in first adapter 236, thus allowing template loaded beads to be pulled down or otherwise isolated by capturing moieties (e.g., streptavidin bound magnetic beads). Similarly, one or more uracils can be included in the bottom strand of the second adapters 232, 234, as depicted in FIG. 2A.

FIG. 2D schematically shows, similar to FIG. 2A, an additional pre-enrichment workflow. In some embodiments, a double-stranded template nucleic acid molecule comprises, ligated at each end, an adapter containing one or more cleavable moieties (e.g., an excisable nucleotide such as uracil, a dSpacer, a C3 spacer, or other abasic site, a methylated nucleotide, etc., illustrated as "X"). The methods for pre-enrichment described herein may comprise generating such double-stranded template nucleic acid molecules. The double-stranded template nucleic acid molecule may comprise a template sequence. In such an example, the 5' and 3' ends of a first strand (e.g., strand 202) of the double-stranded template nucleic acid molecule may comprise different overhang sequences. For example, each of the 5' and 3' ends may comprise an adapter with a single or plurality of cleavable moieties (e.g., C3 spacer, methylated nucleotide). On the 5' end of the first strand 202, sequence P1 (e.g., sequence 206) comprises an overhang comprising a cleavable moiety (such as a C3 spacer, e.g., "X"), and an overhang sequence 207, which may be used in downstream capture. On the 3' end of the first strand 202, sequence P2' (e.g., sequence 204) comprises an overhang sequence including one or more cleavable moieties (e.g., a C3 spacer, e.g., "X"). In some embodiments, as described for example below, other cleavable sequences (comprising one or more cleavable moieties) can be used at either or both of the 3' and 5' ends of the first strand 202 (e.g., in place of the C3 spacers in sequence 204 and sequence 206). Similar to FIG. 2A, the sequence P2' is at least partially complementary to a sequence P2 bound to support 210, such as a bead. Optionally, a polymerase (e.g., Taq polymerase) and reaction reagents (e.g., nucleotide bases) may be used to process the double-stranded template nucleic acid molecule, e.g., to facilitate hybridization of the double-stranded template nucleic acid molecule to the support 210. After the template nucleic acid molecule hybridizes to support 210, a ligase is used to repair the nick such that the second strand 212 is covalently attached to support 210.

In addition to one or more cleavable moieties, sequence 206 can comprise an overhang sequence 207 or any appropriate capture moiety. In some examples, the overhang sequence is configured for capture by a capturing moiety, e.g., a capture oligonucleotide. After strand 212 is covalently linked to support 210, capture beads (e.g., magnetic beads) each comprising a capture oligonucleotide 209 may be introduced to a reaction mixture containing numerous supports (some of which are covalently linked with template nucleic acid molecules and some of which are not). In some instances, at least a portion of the capture oligonucleotide 209 is complementary to the overhang sequence 207 of strand 202. Supports that are covalently linked to a template nucleic acid molecule may have the overhang sequence 207 that binds to the capture oligonucleotide 209, and therefore can be selectively pulled down or otherwise isolated using the capture beads (e.g., magnetic beads) comprising the capturing moiety, such as via applying a magnetic field. As a result, the supports comprising the respective template nucleic acid molecules coupled thereto (e.g., covalently linked thereto) may be isolated and enriched from the other supports that do not have a template nucleic acid molecule attached. An enzyme, such as an endonuclease, e.g., APE1, MspJI, etc., can then be added to the reaction mixture to cleave off the C3 spacers (or methylated nucleotides) that are 3' to the overhang sequence 207 before the support-template nucleic acid complexes are further processed (e.g., amplified and sequenced).

As described herein, the cleavable moiety may comprise any useful cleavable or excisable moiety. For example, the cleavable moiety may comprise a uracil, a ribonucleotide, or other modified nucleotide that is excisable or cleavable using an enzyme (e.g., UDG, RNAse, endonuclease, etc.). The cleavable moiety may comprise an abasic site or an analog of an abasic site (e.g., dSpacer), a dideoxyribose. The cleavable moiety may comprise a spacer, e.g., C3 spacer, hexanediol, triethylene glycol spacer (e.g., Spacer 9), hexaethyleneglycol spacer (e.g., Spacer 18), or combinations or analogs thereof. The cleavable moiety may comprise a modified nucleotide, e.g., a methylated nucleotide. The modified nucleotide may be recognized specifically by an enzyme (e.g., a methylated nucleotide may be recognized by MspJI). The cleavable moiety may be cleaved enzymatically (e.g., using an enzyme such as UDG, RNAse, APE1, MspJI, etc.). Alternatively, or in addition to, the cleavable moiety may be cleavable using a stimulus, e.g., photo-stimulus, chemical stimulus, thermal stimulus, etc., as described elsewhere herein.

It will be appreciated that combinations of cleavable moieties may be attached (e.g., via ligation or amplification of adapter molecules) to the template nucleic acid molecules. For example, referring to FIGS. 2A-2D, the first strand (e.g., 202) may comprise the same or different cleavable moieties at the 5' end and the 3' end. In some examples, the first strand comprises one or more cleavable uracil moieties at an end (5' or 3') and one or more ribonucleotides at the opposite (3' or 5') end. In another example, the first strand comprises one or more C3 spacer moieties at an end, and also a C3 spacer at the opposite end. It will be appreciated that any combination of cleavable moieties (e.g., uracils, ribonucleotides, spacers, abasic sites, enzyme-specific modified nucleotides, such as methylated nucleotides, etc.) may be incorporated at either or both the 5' end and 3' end of the template nucleic acid molecule. Similarly, in instances where the template nucleic acid molecule is double-stranded, the cleavable moieties may be disposed on different strands. For example, one strand may comprise a cleavable moiety at the 5' end and the other strand may comprise a cleavable moiety at the 5' end. Alternatively, one strand may comprise a cleavable moiety at the 3' end and the other strand may comprise a cleavable moiety at the 3' end. As different moiety types and locations are possible, the methods described herein may also provide for orthogonal cleavage mechanisms, such that one moiety at one end of a template nucleic acid molecule may be cleavable but another cleavable moiety on the other end of the template nucleic acid molecule may not be cleavable by the same mechanism. Such orthogonal cleavage mechanisms may be beneficial in multiple processing operations; for example, the template molecule may comprise different cleavable moieties (e.g., a first moiety and a second moiety) at each end. Accordingly, attachment of template molecules to supports may be facilitated by cleavage or excision of the first moiety that does not affect the second moiety. Subsequent ligation and pre-enrichment may be performed, and elution of the supports may be facilitated by cleavage of the second moiety. In some embodiments, following elution of the supports, amplification of the template molecules is performed on the support, as is described elsewhere herein. In such instances, it may be useful to have a different cleavable moiety, e.g., on the template nucleic acid molecule, e.g., at or proximal to the support, or on the primer coupled to the support.

Referring again to FIG. 2D, an overhang sequence of an adapter on the template nucleic acid molecule may be used for purification or pre-enrichment via capture using a bead with a complementary oligonucleotide. The overhang sequence of the adapter can be any useful length, e.g., 1, 2, 3, 4, 5, 6, 7, 8, 9, 10, 20, 30, 40, 50, 60, 70, 80, 90, 100 or greater base pairs. The overhang sequence may be at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 100 or greater base pairs. Alternatively, the overhang sequence may be at most 100, at most 90, at most 80, at most 70, at most 60, at most 50, at most 40, at most 30, at most 20, at most 10, at most 9, at most 8, at most 7, at most 6, at most 5, at most 4, at most 3, at most 2, or at most 1 base pair in length. In some instances, the complementary oligonucleotide (e.g., coupled to bead) may comprise a sequence that is complementary to the entire overhang sequence of the template nucleic acid molecule, or a portion thereof.

Figure 2E:
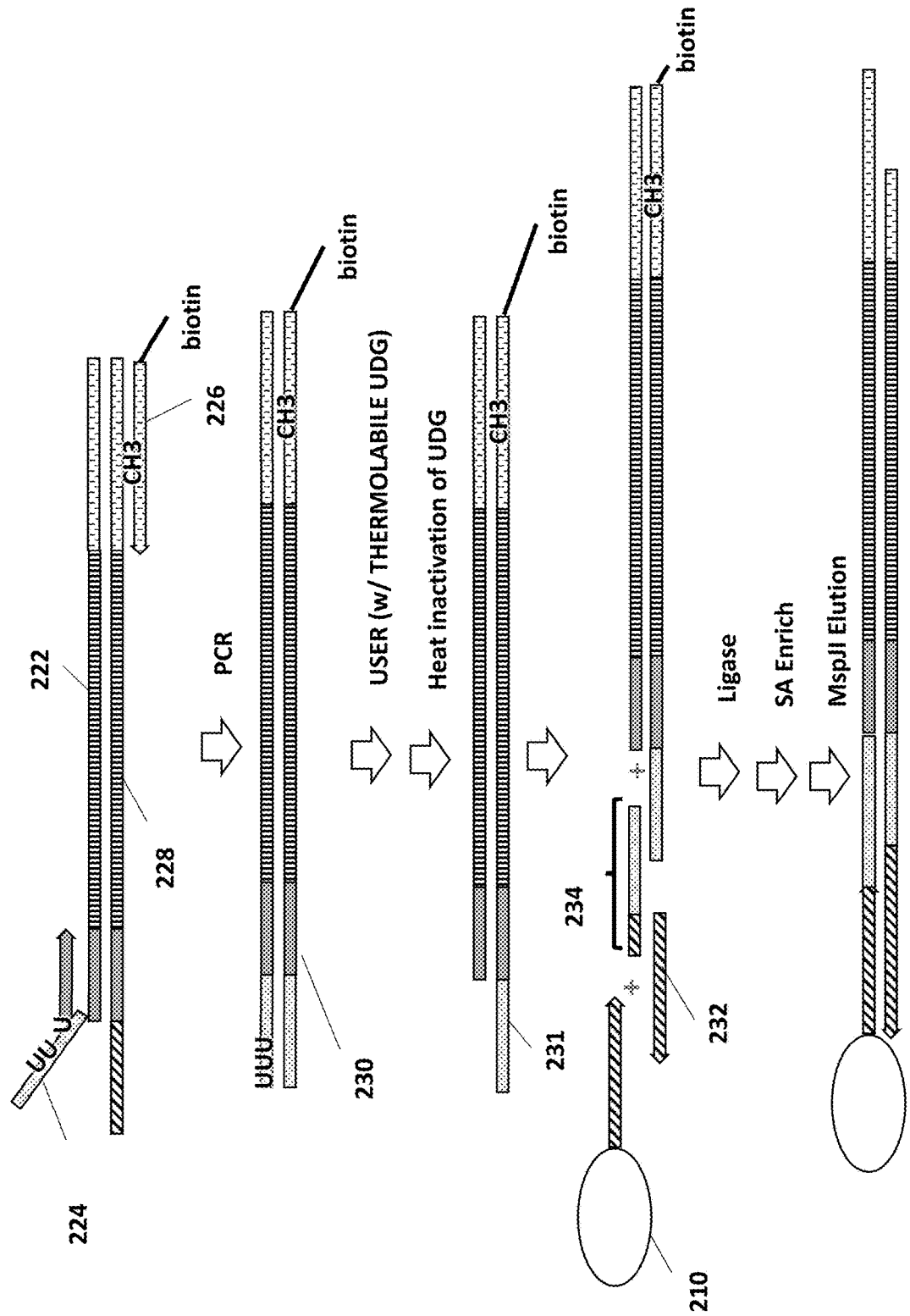
FIGS. 2E-2F illustrate example workflows for processing template nucleic acid molecules using a splint oligonucleotide and optionally, a bridge molecule.
Figure 2F:
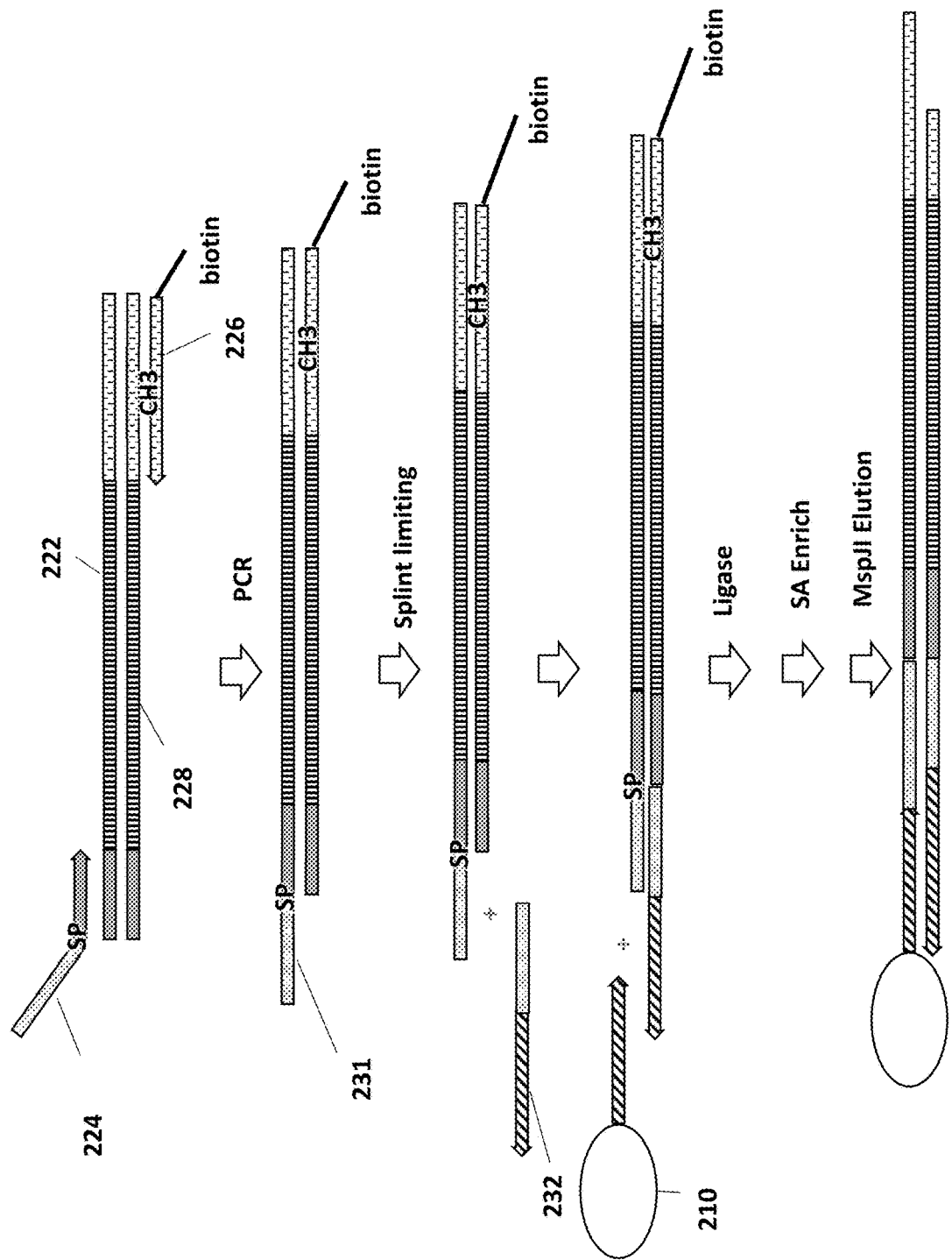

In some embodiments, the template nucleic acid molecules (e.g., from a library of template nucleic acid molecules) attach indirectly to the supports, e.g., via intermediary molecules such as splint and/or bridge oligonucleotides. As shown in FIGS. 2E-2F, attachment of the template nucleic acid molecules may be facilitated by a splint oligonucleotide 232 and optionally, a bridge molecule 234. For example, FIG. 2E shows an example workflow, similar to FIG. 2B, in which a template nucleic acid molecule is generated from a duplex template molecule using a combination of primers comprising different cleavable moieties (e.g., a uracil-containing primer 224 and a methylated nucleotide-containing primer 226). Following amplification, the template nucleic acid molecules may be contacted with an enzyme (e.g., USER with a thermolabile UDG) to cleave one or more cleavable moieties (e.g., uracil) of the template nucleic acid molecule, thus generating a 3' overhang 231. The overhang 231 may not be complementary to a sequence on a support 210. Attachment of the overhang 231 may be facilitated by a bridge oligonucleotide 234 and a splint oligonucleotide 232. The bridge oligonucleotide 234 may comprise a sequence complementary to at least a portion of the overhang 231 and another sequence that is complementary to at least a portion of the splint oligonucleotide 232. The splint oligonucleotide 232 may comprise a sequence complementary to a sequence on the support 210. Accordingly, hybridization of the template nucleic acid molecule to the bridge oligonucleotide 234 and the splint oligonucleotide 232 may facilitate attachment of the template nucleic acid molecule to the support 210. Following hybridization, a ligase and optionally a polymerase may be added to covalently attach the first strand 222 to the support 210. Subsequent processing (e.g., enrichment, treatment with an enzyme to cleave one or more cleavable moieties (e.g., MspJI to cleave methylated nucleotides) may be performed, as is described elsewhere herein.

FIG. 2F shows an alternative scheme for attachment of a template nucleic acid molecule to a support using a splint oligonucleotide (also referred to herein as "splint molecule"). Similar to FIG. 2B and FIG. 2E, a template nucleic acid molecule is generated from a duplex template sequence using a combination of primers comprising different cleavable moieties (e.g., a spacer-containing primer 224 and a methylated nucleotide-containing primer 226, the spacer denoted "SP"). In some instances, one of the primers 224 may comprise a moiety that inhibits amplification (e.g., a spacer moiety). The amplification-inhibiting moiety may be the same as the cleavable moiety. Following amplification, the template nucleic acid molecule may comprise an overhang sequence 231. A splint molecule 232 may be contacted with the template nucleic acid molecule. The splint molecule 232 may comprise a sequence complementary to the overhang 231 as well as a sequence complementary to a sequence of a support 210. Accordingly, hybridization of the template nucleic acid molecule to the splint oligonucleotide 232 may facilitate attachment of the template nucleic acid molecule to the support 210. Following hybridization of the splint oligonucleotide 232 to the sequence of the support 210, a ligase and optionally a polymerase may be added to covalently attach the first strand 222 to the support 210. Subsequent processing, e.g., enrichment, treatment with an enzyme to cleave one or more cleavable moieties (e.g., MspJI to cleave methylated nucleotides) may be performed, as is described elsewhere herein.

While FIGS. 2E-2F illustrate the splint and bridge molecules provided as separate items, it will be appreciated that the splint molecule and/or bridge molecule may be provided as a pre-annealed complex. For instance, referring the FIG. 2E, the bridge molecule 234 may be provided pre-annealed to the splint molecule 232. Alternatively, or in addition to, the splint molecule 232 may be provided pre-annealed to the support 210. Similarly, referring to FIG. 2F, the splint molecule 232 may be provided as pre-annealed to the support 210.

As shown in FIGS. 2E-2F, in some instances, hybridization and attachment of the template nucleic acid molecule to the support may only occur if a splint (and, in some cases, a bridge) is provided. Accordingly, the ratio of support-to-template nucleic acid molecule attachment may be controlled by controlling the amount of splint (and bridge) molecules that is provided. For example, where an excess of template nucleic acid molecules is provided, any useful support-to-template nucleic acid molecule ratio may be achieved by controlling the amount of splint (and bridge) molecules that is provided. As the splint oligonucleotide (and bridge) is the rate-limiting reagent, using such a splint-mediated process may obviate the need to quantify or quantitate the number of ligatable template nucleic acid molecules (e.g., UDG-treated template nucleic acid molecules that have 3' ligatable ends). Since these ligatable molecules may be challenging to quantitate, using the splint-mediated attachment approach can overcome this challenge, since the attachment ratio of the template nucleic acid molecule to the support is controlled by the splint (and bridge) concentration. See also, Example 15. In other instances, the template nucleic acid molecules may be quantitated (e.g., using qPCR) and the attachment ratio to the supports may be controlled using the splint and/or bridge molecule concentration.

In some examples, the ratio of the splint (and/or bridge) molecule-to-template nucleic acid molecule ratio may be about 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100 or less. In other examples, it may be useful to capture as many of the template nucleic acid molecules on the supports, and accordingly, the ratio of the splint (and/or bridge) molecule-to-template nucleic acid molecule ratio may be greater than 1, e.g., about 2 times (×), about 3×, about 4×, about 5×, about 6×, about 7×, about 8×, about 9×, about 10×, or greater. It will be appreciated that a range of concentrations of the splint, bridge, template nucleic acid molecules, and supports may be varied according to a designated attachment ratio of the template nucleic acid molecule to the support. As described above, in some instances, the bead is provided at a lower concentration than the concentration of the template (and/or splint and bridge molecules), which may facilitate generation of monoclonal support populations.

The bridge or splint molecule may comprise any useful number of nucleotide bases, e.g., between about 10-100 nucleotide bases. The bridge or splint molecule, or both, may comprise at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 200 or more nucleotide bases. The bridge or splint molecule, or both, may comprise at most about 200, at most 100, at most 90, at most 80, at most 70, at most 60, at most 50, at most 40, at most 30, at most 20, at most 10, at most 9, at most 8, at most 7, at most 6, at most 5, at most 4, at most 3, at most 2, or at most 1 nucleotide base. It will be appreciated that the bridge or splint molecule, or both, may comprise a range of nucleotide base lengths, e.g., about 30 bases. The bridge molecule may have the same length (e.g., number of bases) as the splint molecule, or the bridge molecule may have a different length than the splint molecule. The bridge molecule and the splint molecule may comprise complementary sequences to facilitate hybridization; such complementary sequences may be any useful length, e.g., about 1, about 2, about 3, about 4, about 5, about 6, about 7, about 8, about 9, about 10, about 15, about 20, about 30, about 40, about 50 or more nucleotides in length. The complementary sequences may be at least 1, at least 2, at least 3, at least 4, at least 5, at least 6, at least 7, at least 8, at least 9, at least 10, at least 20, at least 30, at least 40, at least 50 or more nucleotides in length. Alternatively, the complementary sequences may be at most 50, at most 40, at most 30, at most 20, at most 10, at most 9, at most 8, at most 7, at most 6, at most 5, at most 4, at most 3, at most 2 or fewer nucleotides in length.

The bridge and splint molecules may comprise any useful nucleotide sequence. For instance, it may be useful to have a predefined GC content to facilitate annealing or hybridization. Accordingly, the bridge and splint molecule composition and sequence may be altered according to any useful application (e.g., for attachment of the template nucleic acid molecule to a support). Similarly, the nucleotide sequence of the bridge and splint molecule may be adjusted to achieve a specified annealing and/or melting temperature.

The methods for pre-enrichment described herein may additionally comprise generating the template nucleic acid molecules, e.g., prior to attachment of the template nucleic acid molecules to a support. The template nucleic acid molecules may be single-stranded, double-stranded, or partially double-stranded. As illustrated in FIGS. 2A-2F, the double-stranded template nucleic acid molecules may be generated by attaching one or more adapters to an initial template sequence (e.g., 238), e.g., via ligation or amplification. In some instances, the one or more adapters may be ligated to the initial template sequence using a splint ligation method. Examples of splint ligation methods can be found in Single Reaction Single-stranded Library (SRSLY) (see, e.g., C. J. Troll et al. *BMC Genomics*, 20, 1023 (2019) or Splinted Ligation Adapter Tagging (SPLAT) approach (see, e.g., A. Raine et al. *Nucl. Acids Research*, vol 45, no. 6 (2017), each of which is hereby incorporated by reference herein in its entirety). In such instances, the adapters may comprise a sequence that is complementary to a strand of the initial template sequence. In some examples, the adapters may comprise additional functional sequences (e.g., primer sequences) or moieties (e.g., blocking moieties).

Figure 3:
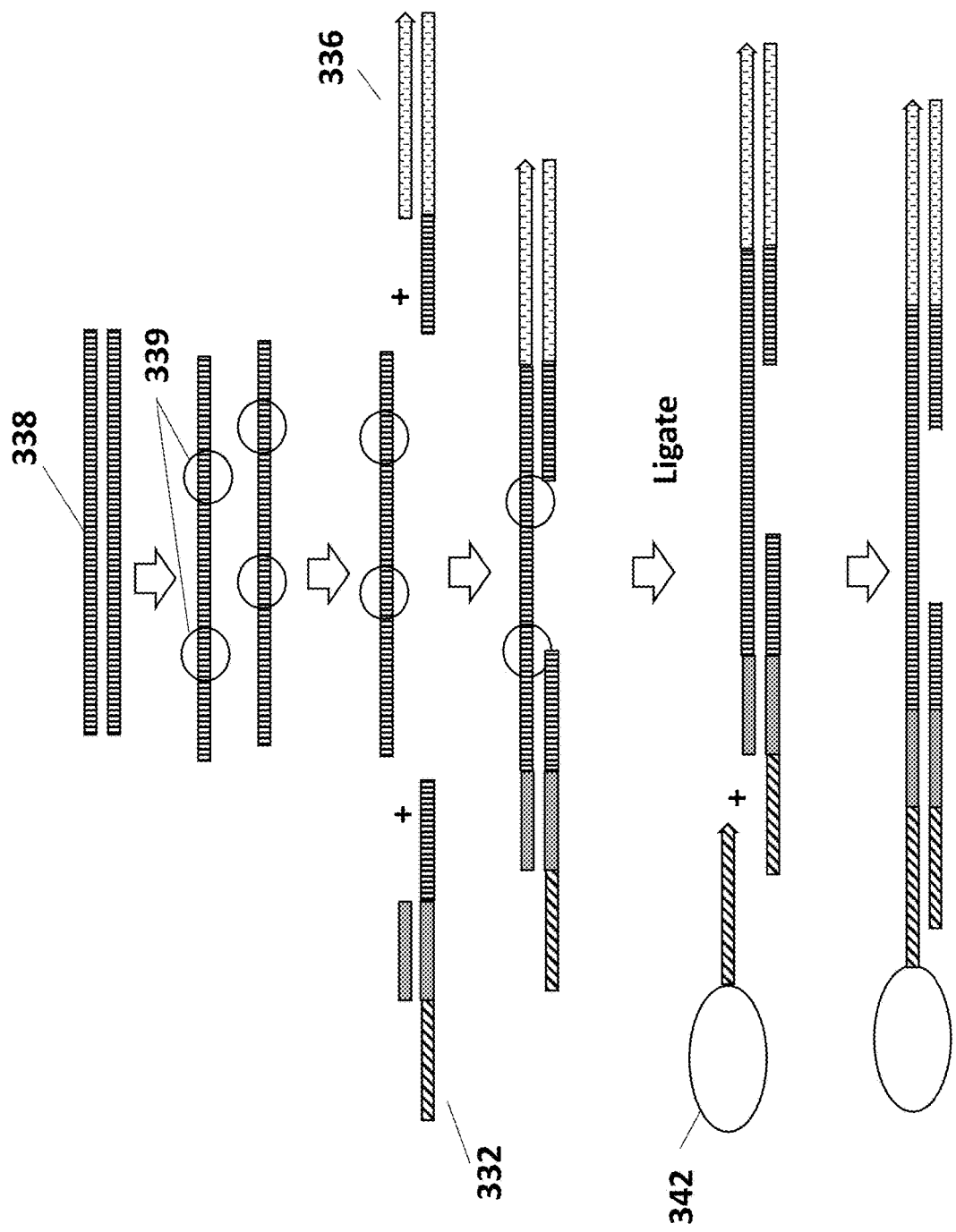
FIG. 3 shows an example workflow for generating a template nucleic acid molecule (e.g., of a library of template nucleic acid molecules) by ligating adapter molecules to template sequences.

FIG. 3 shows an example workflow of generating a partially double-stranded template nucleic acid molecule, which can subsequently be attached to a support (e.g., bead) and further processed (e.g., pre-enriched, sequenced, etc.). A template sequence (e.g., double-stranded template sequence) 338 may be subjected to conditions sufficient to generate single-stranded template sequences. In some instances, the conditions comprise using heat or a chemical denaturant to generate the single-stranded template sequences. Alternatively or in addition to, a protein such as a single-stranded nucleic acid binding protein 339 may be provided to generate or maintain the single-stranded-ness of the template sequences 338. The single-stranded template sequences may be ligated to one or more adapters at each end. For example, a first adapter 336 may be ligated at one end and a second adapter 332 may be ligated at the other end. In some instances, the first adapter 336 and/or the second adapter 332 are partially double-stranded. The first adapter 336 and/or second adapter 332 may comprise a single-stranded overhang sequence, which may be complementary and may hybridize to a portion of the single-stranded template sequence. The overhang sequence may comprise, for example, a random N-mer or a targeted sequence (e.g., targeted primer sequence). In some instances, the overhang sequence of the first adapter 336 may be disposed at the 5' terminus, and the overhang sequence of the second adapter 332 may be disposed at the 3' terminus, such that the polarity or directionality of the initial template sequence is maintained in subsequent processing operations (e.g., amplification, pre-enrichment, sequencing, etc.). For instance, the first adapter 336 may comprise a reverse primer sequence and a 5' overhang sequence, and the second adapter 332 may comprise a forward primer sequence and a 3' overhang sequence, such that subsequent pre-enrichment may be performed in the absence of amplification. Alternatively or in addition to, the ligation of the first adapter 336 and the second adapter 332 may maintain the directionality of the initial template sequence. In some instances, the first adapter 336 and/or the second adapter 332 comprises a blocked end (e.g., for preventing ligation or extension). See, Example 6.

The overhang sequences of the first adapter 336 and/or the second adapter 332 may anneal to a portion of the single-stranded template sequence. Subsequent to annealing, ligation of the adapters to the single-stranded template sequence may be performed to generate a template nucleic acid molecule. In some instances, phosphorylation may be performed, e.g., using an enzyme such as a kinase (e.g., T4 polynucleotide kinase) prior to ligation of the adapters to the single-stranded template sequence. The ligated molecule may subsequently be attached to a support (e.g., bead) 342, as described elsewhere herein. Alternatively, the template nucleic acid molecule may be attached to the support and then subjected to ligation. Beneficially, utilizing a splint ligation approach may simplify template nucleic acid preparation workflows, e.g., by obviating, in some instances, the need for amplification processes to add the adapter sequences. Such approaches may also allow for ligation of adapters within a single reaction mixture while maintaining directionality of the template sequences. Such an approach may also be compatible with the pre-enrichment operations described herein and, in some instances, obviate the need for amplification prior to sequencing.

In another example, a SPLAT approach may be used to attach adapters to template sequences. In such an example, the template sequences may be subjected to conditions sufficient to generate nicks in the template sequences and/or to fragment the template sequences (e.g., via amplification in the presence of uracil and using a uracil-excising enzyme to excise the uracil, bisulfite conversion of the template sequences, etc.). Other approaches to fragment the template sequences may be performed, e.g., mechanical fragmentation (e.g., shearing, ultrasonication, vortexing, acoustic shearing (e.g., Covaris® shearing), etc.), which may optionally be followed by bisulfite treatment or other enzymatic conversion of non-methylated cytosines to uracil.

Subsequent priming and extension, e.g., in the presence of the first adapter and the second adapter, may be performed to generate a template nucleic acid molecule. Alternatively or in addition to, the adapters may be ligated to an end of the nicked or fragmented template sequence. For example, a first adapter may comprise a sequence (e.g., random N-mer) that may hybridize to a sequence of the template sequence. In some instances, the first adapter may be ligated to a 3' terminus of the nicked or fragmented template sequence, and prior to, concurrently, or subsequently, a second adapter may be ligated to a 5' terminus of the nicked or fragmented template sequence, e.g., via hybridization of a complementary sequence (e.g., random N-mer). The template nucleic acid molecule may then be attached to a support, as described herein, and subjected to further processing, e.g., pre-enrichment.

FIGS. 4A-4C schematically illustrates non-limiting examples of adapter molecules which may be ligated, e.g., using a splint ligation approach, to a template sequence. FIG. 4A shows a pair of adapters in which a first adapter 451 comprises a hairpin sequence and a capture moiety (e.g., biotin) and a second adapter 452 comprises an overhang sequence 401 that may anneal to a support. FIG. 4B shows a pair of adapters in which a first adapter 451 comprises a cleavable ribonucleotide sequence and a capture moiety (e.g., biotin) and a second adapter 452 comprises an overhang sequence 401 that may anneal to a support and a cleavable moiety (e.g., uracil). FIG. 4C shows a pair of adapters in which a first adapter 451 comprises one or more cleavable moieties (e.g., uracil) and a capture moiety (e.g., biotin) and a second adapter 452 comprises an overhang sequence 401 that may anneal to a support and a cleavable moiety (e.g., uracil). In FIGS. 4A-4C, each pair of adapters or each adapter may comprise an overhang sequence capable of annealing to a portion of the template sequence 438 and optionally, a blocking moiety (e.g., amino group). Subsequent annealing and optional ligation of the adapters to the template sequences 438 may be performed to generate a template nucleic acid molecule that may subsequently be attached to a support and subjected to pre-enrichment.

It will be appreciated that the first adapter or second adapter can comprise any combination of functional sequences (e.g., primer sequences, sequencing primers) as well as functional moieties (e.g., blocking moieties, cleavable moieties, capture moieties, etc.). For example, the first adapter or the second adapter may be single-stranded, double-stranded, or partially double-stranded. The first adapter or the second adapter may be configured to hybridize to a splint adapter comprising a sequence complementary to a sequence of the first adapter or the second adapter. Any of the adapters may comprise a cleavable moiety (e.g., uracil, ribonucleotide, methylated nucleotide, spacer, etc.), a capture moiety (e.g., biotin, a capture oligonucleotide sequence, etc.), a blocking moiety, or combinations thereof. The first adapter or the second adapter may comprise a blunt end, an overhang sequence, or combinations thereof. Alternatively or in addition to, the first adapter or the second adapter may comprise a complementary sequence (e.g., a binding sequence) that is complementary to a sequence (e.g., capture sequence) on a support, which may allow for attachment of the adapter or (or adapter-ligated template nucleic acid molecule) to the support. See Example 7.

In some instances, hybridization and attachment of the template nucleic acid molecule to the support may be modulated by adjusting the concentration of one or more adapters that are used to generate the template nucleic acid molecule. For example, the ratio of support-to-template nucleic acid molecule attachment may be controlled by controlling the amount of an adapter (e.g., that is ligated to the 5' end of the template sequence) that is provided. For example, where an excess of template sequences is provided, any useful support-to-template nucleic acid molecule ratio may be achieved by controlling the amount of adapter molecules that is provided. As the adapter molecule is the rate-limiting reagent, using such an adapter-mediated process may obviate the need to quantify or quantitate the number of ligatable template nucleic acid molecules (e.g., UDG-treated template nucleic acid molecules that have 3' ligatable ends). Thus, methods and systems for sample preparation may comprise providing a mixture of a plurality of supports, a plurality of template nucleic acid molecules, and a plurality of adapters, wherein respective concentrations of one or all three of the above are predetermined and/or optimized in the mixture based on a desired output of support-to-template nucleic acid molecule ratio. Since these ligatable molecules may be challenging to quantitate, using the adapter-concentration mediated attachment approach can overcome this challenge, since the attachment ratio of the template nucleic acid molecule to the support is controlled by the adapter concentration. In other instances, the template nucleic acid molecules may be quantitated (e.g., using qPCR) and the attachment ratio to the supports may be controlled using the adapter concentration. The methods and system may further comprise performing of a pre-enrichment operation, or multiple pre-enrichment operations, using a capture moiety on the adapter and/or the template nucleic acid molecule. The pre-enrichment operation may isolate supports that are positively attached to template nucleic acid molecules from supports that have not.

As described herein, a combination of enzymes may be used to facilitate attachment of the template nucleic acid molecules to a support. For example, double-stranded template nucleic acid molecules comprising adapter sequences may be attached to a support using a ligase and optionally, a polymerase (e.g., Taq polymerase). Use of a polymerase in combination with a ligase may facilitate attachment of the template nucleic acid molecules to supports, e.g., by removing excess cleavable moieties or by rendering the template nucleic acid molecule ligatable. For example, in some instances, the template nucleic acid molecule may lack a ligatable feature (e.g., lacking a 5' phosphate group), such that following hybridization of the template nucleic acid molecule to a support (or primer coupled to the support), the template nucleic acid molecule cannot be ligated to the support (or the primer coupled thereto). In such instances, a polymerase may be used to generate a phosphorylated end (e.g., 5' end) of the template nucleic acid molecule, thereby allowing ligation of the template nucleic acid molecule to the support (or primer coupled thereto). In other examples, the polymerase may cleave off excess cleavable moieties (e.g., ribonucleotides or uracil). For example, a template nucleic acid molecule may be generated via amplification using primers comprising the cleavable moieties (e.g., as shown in FIG. 2B). In some instances, the enzymes (e.g., USER or RNase) may not completely remove the cleavable moieties and the template nucleic acid molecule is thus not ligatable to the support (or primer coupled thereto). In such instances, a polymerase may be used to cleave off the excess moieties (e.g., uracil, ribonucleotides) and render the template nucleic acid molecule ligatable to the support (or primer coupled thereto). Use of a polymerase prior to or during the ligation process may increase the number of supports ligated to template nucleic acid molecules (see, e.g., Example 14).

III. Double Strand Preservation for Error Correction

Further provided herein are systems, methods, and compositions for error correction by preserving both strands of a template nucleic acid molecule during amplification. The methods described herein may be particularly advantageous in improving SNP error rates. Referring to FIG. 1, at operations 101-104, the supports and templates may be prepared as illustrated in FIG. 21A-B.

Figure 21A:
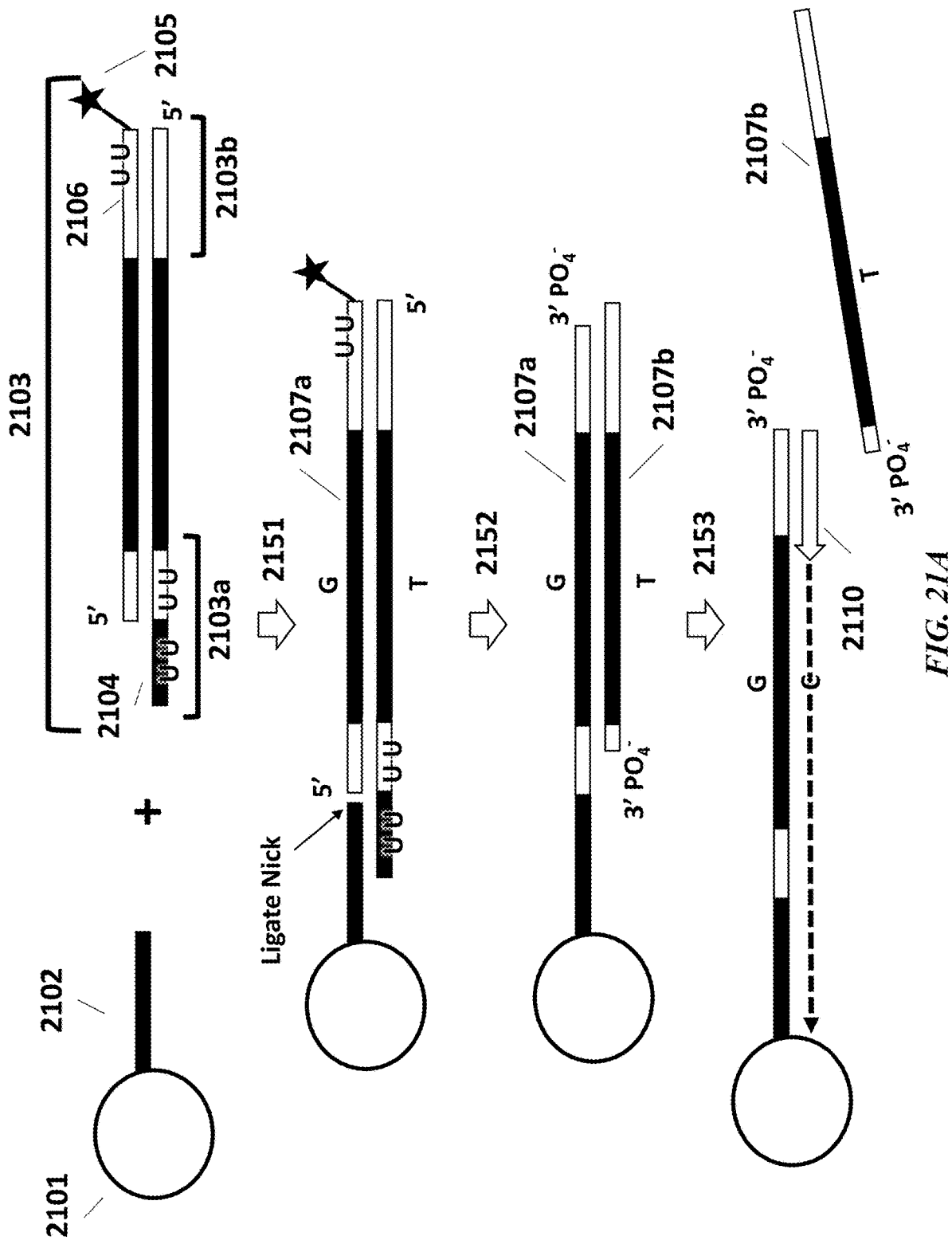
FIG. 21A illustrates a first workflow for extension and amplification on a support.

FIG. 21A illustrates a first workflow for extension and amplification on a support. A support 2101 and template nucleic acid molecule 2103 may be provided. The support 2101 may comprise a plurality of surface primers, e.g., 2102 (only one illustrated in FIG. 21A for clarity), which may be identical and/or comprise a common primer sequence. The template nucleic acid molecule 2103 may comprise a first adapter 2103*a* attached at one end and a second adapter 2103*b* attached at another end. The first adapter may be a partially double-stranded adapter comprise an overhang 2104 configured to bind to surface primer 2102. One or more strands of the first adapter may comprise one or more cleavable moieties (denoted as "U"), such as uracil residues. In the example illustrated in FIG. 21A, the overhang-containing strand comprises the cleavable moieties. The second adapter 2103*b* may be a double-stranded adapter. The second adapter may comprise a capture moiety 2105, such as biotin, and one or more cleavable moieties 2106 (denoted as "U"), such as uracil residues, which are disposed 5' of the cleavable moieties. In the example illustrated in FIG. 21A, the overhang of the first adapter and the capture moiety of the second adapter are attached to different strands of the template insert of the template nucleic acid molecule 2103. The template nucleic acid molecule 2103 may be attached to the support 2101 by annealing the overhang 2104 with the surface primer 2102 and ligating the nick (2151) in the top strand 2107*a*. Prior to or subsequent to nicking, pre-enrichment may be performed where the capture moiety is used to isolate support-template assemblies from negative supports (unbound to a template). In an example, the capture moiety is biotin, and streptavidin-magnetic beads are used to capture the biotin. Then, the U-based cleavage sites may be cleaved using a mix of Uracil-DNA Glycosylase (UDG) and Endonuclease VIII enzymes (2152). The UDG may catalyze the hydrolysis of the N-glycosidic bond from deoxyuridine to release uracil, and Endonuclease VIII may cleave the DNA phosphodiester backbone at AP, creating a 1-nucleotide DNA gap with 5' and 3' phosphate termini. That is, use of the UDG/Endo VIII enzyme combination results in a blocked 3' end of the bottom strand 2107*b* of the template. Prior to, during, or subsequent to commencement of extension and/or amplification reactions (2153), the blocked bottom strand 2107*b* may be detached from the top strand 2107*a* which is covalently bound to the bead 2101. A primer 2110 may anneal to the top strand 2107*a* and a primer extension reaction may commence using the top strand 2107*a* as a template. The template and/or copied strand may then be extended and/or amplified such that the a plurality of surface primers on the support 2101 is extended to copy the top strand 2107*a*. The extension and/or amplification reactions may be performed in partitions (e.g., wells, emulsions) or in bulk. In the workflow of FIG. 21A, one of the template strands because of its blocked end does not get extended, and thus the resulting amplified support includes only derivatives (e.g., copies) of only one of the strands (top strand 2107*a*). This means that certain errors, such as an error SNP, (e.g., FIGS. 21A-B illustrate an artificial SNP of a G/T locus that was introduced during a deamination reaction), are carried forward (or their sources lost) during the extension and/or amplification phase as the support retains information only from a first strand (e.g., only the 'G' of the G/T locus). The errors may be sequencing or processing errors (e.g., chimeric byproducts, etc.) that contaminate the original template sequence (as sourced from the sample). The error may be a base mismatch error, such as a SNP, an indel, or an artificial base mismatch error. It will be appreciated that alternative enzymes that perform the same or similar functions as those described herein (e.g., any enzyme which cleaves the DNA phosphodiester backbone at AP, creating a 1-nucleotide DNA gap with 5' and 3' phosphate termini) may be used in the alternative or in addition. In another example, the cleavable moiety may comprise a ribonucleotide and the enzyme may comprise ribonuclease HII (RNase HII), where upon nicking, a polymerase is used to fill in downstream.

Figure 21B:
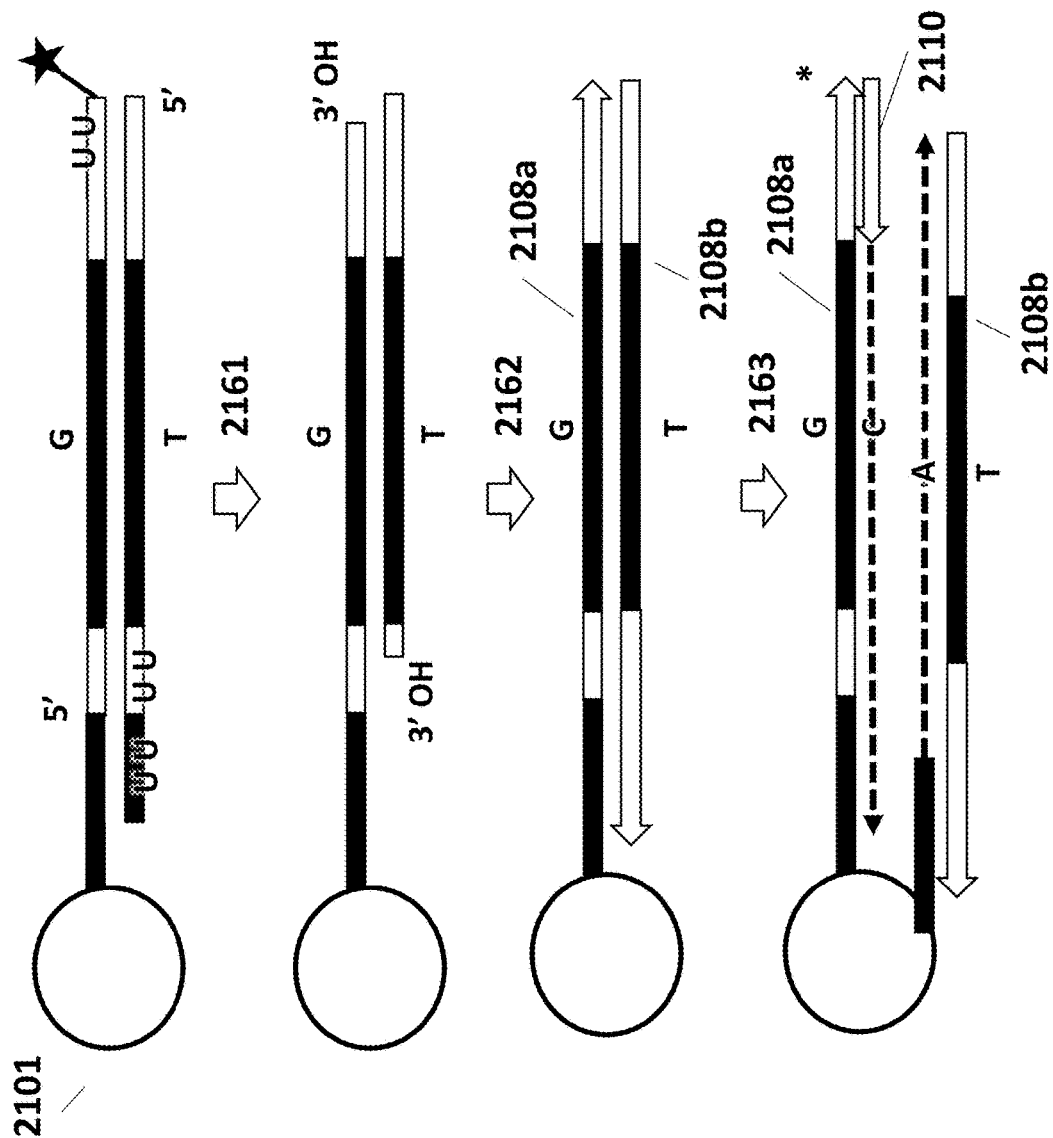
FIG. 21B illustrates a second workflow for extension and amplification on a support.

FIG. 21B illustrates a second workflow for extension and amplification on a support. The support 2101 and template nucleic acid molecule 2103 may be attached together, and pre-enrichment performed as described with respect to FIG. 21A. The U-based cleavage sites may be cleaved using a mix of Uracil-DNA Glycosylase (UDG) and Apurinic/apyrimidinic Endonuclease 1 (APE1) (2161). The UDG may catalyze the hydrolysis of the N-glycosidic bond from deoxyuridine to release uracil, and the APE1 may cleave the DNA phosphodiester backbone at AP sites via hydrolysis leaving a 1-nucleotide gap with 3'-hydroxyl and 5' deoxyribose phosphate (dRP) termini. That is, use of the UDG/APE1 enzyme combination results in an extendable 3' end of the bottom strand 2108*b* of the template. Taq or similar polymerizing enzymes and dNTPs may be added to extend the 3'-hydroxyl site (2162). The bottom strand 2108*b* may be extended using the top strand 2108*a* bound to the support 2101 as a template to generate an extended bottom strand which includes a sequence complementary to the surface primer 2102. Then, the extended bottom strand 2108*b* may be detached from the top strand 2107*a* and anneal to another surface primer on support 2101. A primer 2110 may anneal to the top strand 2108*a* and a primer extension reaction may commence using the top strand 2108*a* as a template (2163). Separately, the other surface primer annealed to the extended bottom strand may be extended using the extended bottom strand as a template (2163). The template strands, and/or their copies, may be extended and/or amplified such that a plurality of surface primers on the support 2101 is extended to copy the top strand 2108*a* and the bottom strand 2108*b*. The extension and/or amplification reactions may be performed in partitions (e.g., wells, emulsions) or in bulk. In some cases, only the first stage extension reaction (e.g., extending the bottom strand 2108*b* to generate the extended bottom strand) may be performed out of partition and the next stage extension reaction(s) may be performed in partition, such that within the partition a support comprising one copy of the top strand and one copy of the bottom strand is subjected to amplification. In the workflow of FIG. 21B, unlike in the workflow of FIG. 21A, both template strands are extended, and thus the resulting amplified support includes derivatives (e.g., copies) from both strands (top strand 2108*a*, bottom strand 2108*b*). This means that certain sequencing information, such as an artificial base mismatch error, (e.g., FIGS. 21A-B illustrate an artificial SNP of a G/T locus that was introduced during a deamination reaction), is retained on the support via the first strand copies (e.g., 'G' of the G/T locus) and the second strand copies (e.g., 'T' of the G/T locus). It will be appreciated that alternative enzymes that perform the same or similar functions as those described herein (e.g., any enzyme which cleaves the DNA phosphodiester backbone at AP sites via hydrolysis leaving a 1-nucleotide gap with 3'-hydroxyl and 5' deoxyribose phosphate (dRP) termini) may be used in the alternative or in addition. In another example, the cleavable moiety may comprise a ribonucleotide and the enzyme may comprise RNase HII, where upon nicking, a polymerase is used to fill in downstream.

The resulting amplified support may be a pseudo-polyclonal bead wherein a first set of strands covalently attached to the support are copies of the top strand 2108*a* and a second set of strands covalently attached to the support are copies of the bottom strand 2108*b*. The ratio of top strand and/or top strand copies in all extended strands on the support may be at least about 0.001, 0.01, 0.1, 0.2, 0.3, 0.4, 0.5, 0.6, 0.7, 0.8, 0.9, 0.99, 0.999. The ratio of top strand and/or top strand copies in all extended strands on the support may be at most about 0.001, 0.01, 0.1, 0.2, 0.3, 0.4, 0.5, 0.6, 0.7, 0.8, 0.9, 0.99, 0.999. The ratio of bottom strand and/or bottom strand copies in all extended strands on the support may be at least about 0.001, 0.01, 0.1, 0.2, 0.3, 0.4, 0.5, 0.6, 0.7, 0.8, 0.9, 0.99, 0.999. The ratio of bottom strand and/or bottom strand copies in all extended strands on the support may be at most about 0.001, 0.01, 0.1, 0.2, 0.3, 0.4, 0.5, 0.6, 0.7, 0.8, 0.9, 0.99, 0.999. In some cases, the ratio of top strand copies to bottom strand copies may be approximately 5:5.

A plurality of supports prepared in this manner may be subjected to sequencing, such as via the sequencing methods described elsewhere herein. Sequencing may be flow-based sequencing, where each sequencing run comprises a plurality of flow steps (which may or may not be provided in flow cycles), a template is annealed to a primer and the primer is extended in a stepwise manner with distinct flow steps, and in a distinct flow step, nucleotides of a single base are flown in and their incorporation or lack thereof by the extending primer is detected, which incorporation or lack thereof is determined from sequencing signals. In some cases, detection comprises detection of a fluorescently labeled nucleotide (e.g., fluorescence-based sequencing signals). In some cases, the nucleotide flows comprise non-terminated nucleotides. In some cases, the nucleotide flows comprise terminated nucleotides. A support comprising amplification products from a template, as described herein, may be used to amplify the sequencing signals detected per template by aggregating and/or averaging the total signals from all the copies on the support.

Figures 25A, 25B:
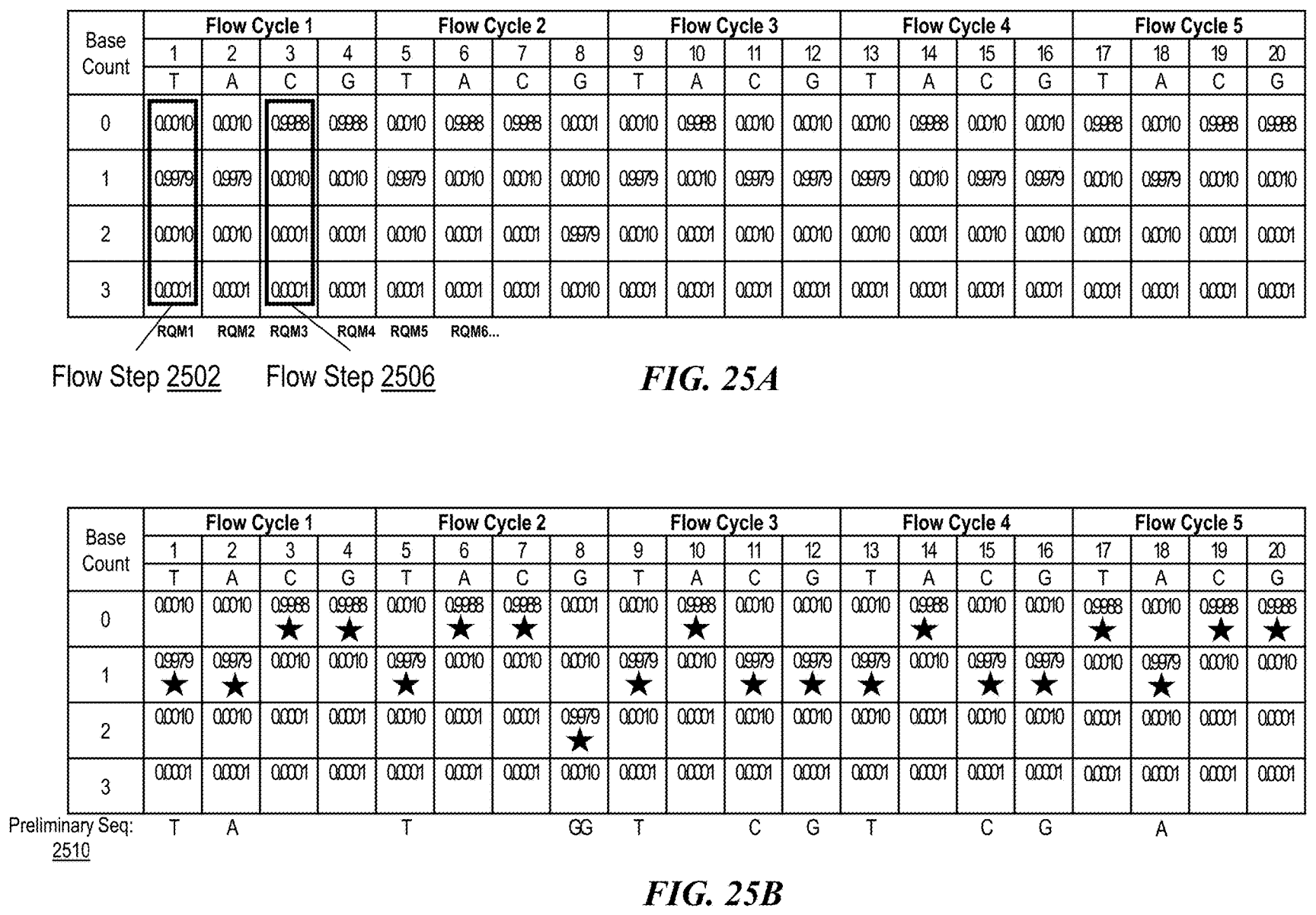

Flow-based sequencing, as described herein, results in sequencing information for each flow, for each support (e.g., for each amplified colony of a template nucleic acid molecule). FIG. 25A illustrates an exemplary flowgram of detected sequencing signals after five exemplary flow cycles are performed, each flow cycle comprising the use of non-terminated nucleotide flows, in accordance with some embodiments. Solely by way of example, a primer extended along a template using a repeating flow-cycle order of T-A-C-G may result in a sequencing data flowgram set shown in FIG. 25A. Each column in FIG. 25A corresponds to a flow step and the values in each column collectively represent the detected signal intensity in the corresponding flow step, as described below.

In each flow step, the flow signal can be determined from an analog signal that is detected during the sequencing process, such as a fluorescent signal of the one or more bases incorporated into the sequencing primer during sequencing. Although an integer number of zero or more bases are incorporated at any given flow position, a given analog signal many not perfectly match with the analog signal. Therefore, in some embodiments, for a given flow step (e.g., flow step 2502), the detected signal intensity can be expressed in probabilistic terms. Specifically, the detected signal intensity can be expressed in four likelihood values corresponding to 0 base, 1 base, 2 bases, and 3 bases, respectively.

In the depicted example, for flow step 2502, the detected signal intensity is expressed by a first likelihood value of 0.001 for 0 base, a second likelihood value of 0.9979 for 1 base, a third likelihood value of 0.001 for 3 bases, and a fourth likelihood value of 0.0001 for 4 bases. This can be interpreted to indicate that there is a high statistical likelihood that one nucleotide base has been incorporated. In the depicted example, the incorporation is a T since the flow step introduced labeled T nucleotides, which means there is an A in the template.

On the other hand, in flow step 2506, the detected signal intensity is expressed by a first likelihood value of 0.9988 for 0 base, a second likelihood value of 0.001 for 1 base, a third likelihood value of 0.001 for 3 bases, and a fourth likelihood value of 0.0001 for 4 bases. This can be interpreted to indicate that there is a high likelihood that no nucleotide base has been incorporated. In the depicted example, no C has been incorporated.

Accordingly, the flowgram set in FIG. 25A is formatted as a sparse matrix, with a flow signal represented by a plurality of likelihood values indicating a plurality of likelihoods for a plurality of base homopolymer length counts (e.g., 0 base count, 1 base count, 2 base counts, and 3 base counts) at each flow position.

The homopolymer length likelihood may vary, for example, based on the noise or other artifacts present during detection of the analog signal during sequencing. In some embodiments, if the homopolymer length likelihood statistical parameter or likelihood is below a predetermined threshold, the parameter may be set to a predetermined non-zero value that is substantially zero (i.e., some very small value or negligible value) to aid the downstream statistical analysis further discussed herein, wherein a true zero value may give rise to a computational error or insufficiently differentiate between levels of unlikelihood, e.g., very unlikely (0.0001) and inconceivable (0).

With reference to FIG. 25B, a preliminary sequence can be determined based on the flowgram in FIG. 25A. For example, the most likely sequence can be determined by selecting the base count with the highest likelihood at each flow position, as shown by the stars in FIG. 25B. Thus, the preliminary sequence 2510 can be determined as: TATGGTCGTCGA (SEQ ID NO: 1).

From the preliminary sequence (e.g., preliminary sequence 2510), the reverse complement (i.e., the template strand or the nucleic acid sequence of interest) can be readily determined. Further, the likelihood of this sequencing data set, given the TATGGTCGTCGA (SEQ ID NO: 1) sequence (or the reverse complement), can be determined as the product of the selected likelihood at each flow position.

When the pseudo-polyclonal beads generated via the workflow of FIG. 21B are sequenced, at the flow step interrogating an error site (e.g., artificial SNP locus), because different subsets of strands on the support have a different base, upon addition of a single base, the sequencing signals from that support may undergo phasing and cause an overall degradation in sequencing quality for that support. Phasing is an inherent issue across sequencing technologies.

The chemical process of incorporating nucleotides into an extending primer is often imperfect, causing desynchronization among strands within a sequencing cluster. As the primer strands within the cluster extend, the primers can become out of phase, for example due to leading strands (caused by an over-incorporation of nucleotides into the extending sequencing primer) or lagging strands (caused by an under-incorporation of nucleotides into the extending sequencing primer). Desynchronization may result in signal degradation (from that support undergoing such desynchronization), and therefore reduced accuracy, when detecting the presence or absence of nucleotide incorporation into the extending primer as the read length increases.

A pseudo-polyclonal bead will exhibit a phasing event at the error site. This phasing event that results from an artificial base mismatch error may not be distinguishable from a phasing event due to misincorporation of too many or too few nucleotides into a homopolymer region. In either case, phasing is likely to increase the error in data analysis (e.g., in base-calling from sequencing signal data or in alignment of sequencing reads to a reference genome). The degradation in sequencing quality from phasing may trigger the trimming of a sequencing read derived from the sequencing signals. In the illustrated example in FIG. 21B, upon trimming of the sequencing read, the artificial G/T locus and all downstream signals may simply be removed or ignored from base calling. Trimming will result in an overall increase in the sequencing quality for a support. Beneficially, such filtering of 'error' SNPs (false positive calls) may help distinguish 'true' SNPs and improve SNP calling.

IV. Data Analysis for Error Correction

Figure 24:
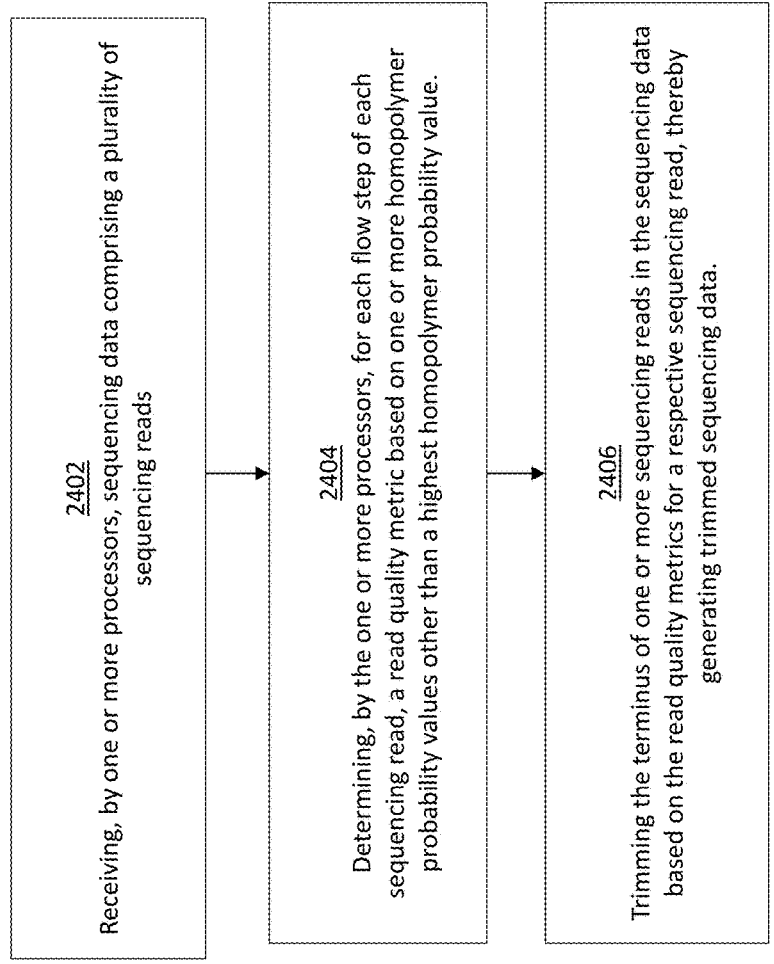
FIG. 24 illustrates an exemplary method for increasing sequencing read quality, in accordance with some embodiments.

FIG. 24 illustrates an exemplary method 2400 for increasing sequencing read quality, in accordance with some embodiments. In some embodiments, process 2400 is performed, for example, using one or more electronic devices implementing a software platform. In some examples, process 2400 is performed using a client-server system, and the blocks of process 2400 are divided up in any manner between the server and client device(s). In other examples, process 2400 is performed using only a client device or only multiple client devices. In process 2400, some blocks are, optionally, combined, the order of some blocks is, optionally, changed, and some blocks are, optionally, omitted. In some examples, additional steps may be performed in combination with the process 2400. Accordingly, the operations as illustrated and described herein are exemplary by nature and, as such, should not be viewed as limiting.

At block 2402, an exemplary system (e.g., one or more electronic devices) receives, by one or more processors, sequencing data comprising a plurality of sequencing reads. Each sequencing read of the plurality of sequencing reads can be generated according to a flow sequencing method as described herein.

At block 2404, the system determines, by the one or more processors, for each flow step of each sequencing read, a read quality metric. For example, with reference to FIG. 25A, for each flow step (i.e., each column in the flow gram), a read quality metric (also known as regressed residual) is calculated. For example, for flow step 2502, a read quality metric RQM1 is calculated; for flow step 2506, RQM3 is calculated.

In some embodiments, the read quality metric for each flow step of each sequencing read is calculated based on a second highest homopolymer probability value ($p_{2nd}$). For example, in flow step 2502 in FIG. 25A, the second highest probably value is 0.0010. In some embodiments, the read quality metric (i.e., $r_s$) is calculated as:

$$r_s = \log_{10}(p_{2nd}/\epsilon)/10, \quad (1)$$

Where $\epsilon$ is a scaling factor and $p_{2nd}$ is the second highest probability at the flow step (e.g., representing the second most likely h-mer). In some embodiments, $\epsilon$ can be set at a value between $1\times10^{-2}$ and $1\times10^{-4}$.

The read quality metric for a given flow step can be calculated using other techniques. In some embodiments, rather than $p_{2nd}$, $(1-p_{1st})$ is used in the formula above. In cases in which $p_{1st}+p_{2nd}=1$, the two formula variations would yield the same read quality metric. In cases in which $p_{1st}+p_{2nd}+p_{3rd}=1$, the two formula variations would yield different read quality metrics. In most cases, $p_{3rd}$, $p_{4th}$, $p_{5th}$, etc. are small numbers in comparison with $p_{1st}$ and $p_{2nd}$. In any such case, $p_{1st}+p_{2nd}+\ldots+p_{nth}=1$.

A higher read quality metric can be indicative a weaker signal. For example, a higher $p_{2nd}$ can indicate a lower $p_{1st}$. Because the base count associated with $p_{1st}$ is selected a lower $p_{1st}$ can indicate a lower confidence in the selected base count. Thus, the read quality metric is used to determine flows with low confidence, which can indicate deterioration in h-mer determination accuracy, in a sequencing read and determine where (e.g., at which flow) to trim the sequencing read, as described below.

It will be understood that the read quality metric could also be calculated, with appropriate modifications to the read quality metric function, using any h-mer probability value each flow step of each sequencing read (e.g., $p_{1st}$, $p_{2nd}$, $p_{3rd}\ldots, p_{nth}$). Calculating the read quality metric with, for example, a first highest homopolymer probability value can be performed thus:

$$r_s = \log_{10}((1-p_{1st})/\epsilon)/10, \quad (2)$$

where $\epsilon$ would be set as in equation (1).

Figure 22A:
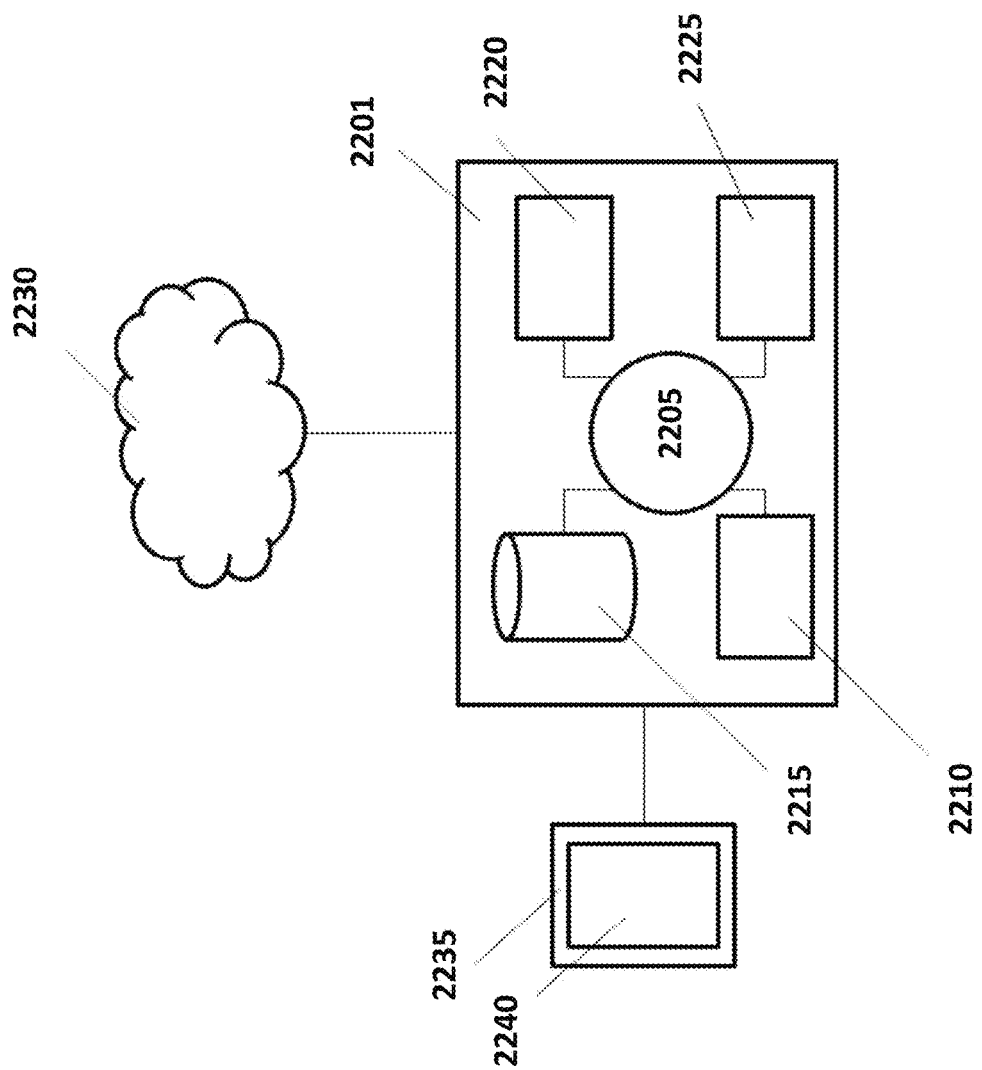
FIG. 22A shows a computer control system that is programmed or otherwise configured to implement methods provided herein.
Figures 22B, 22C:
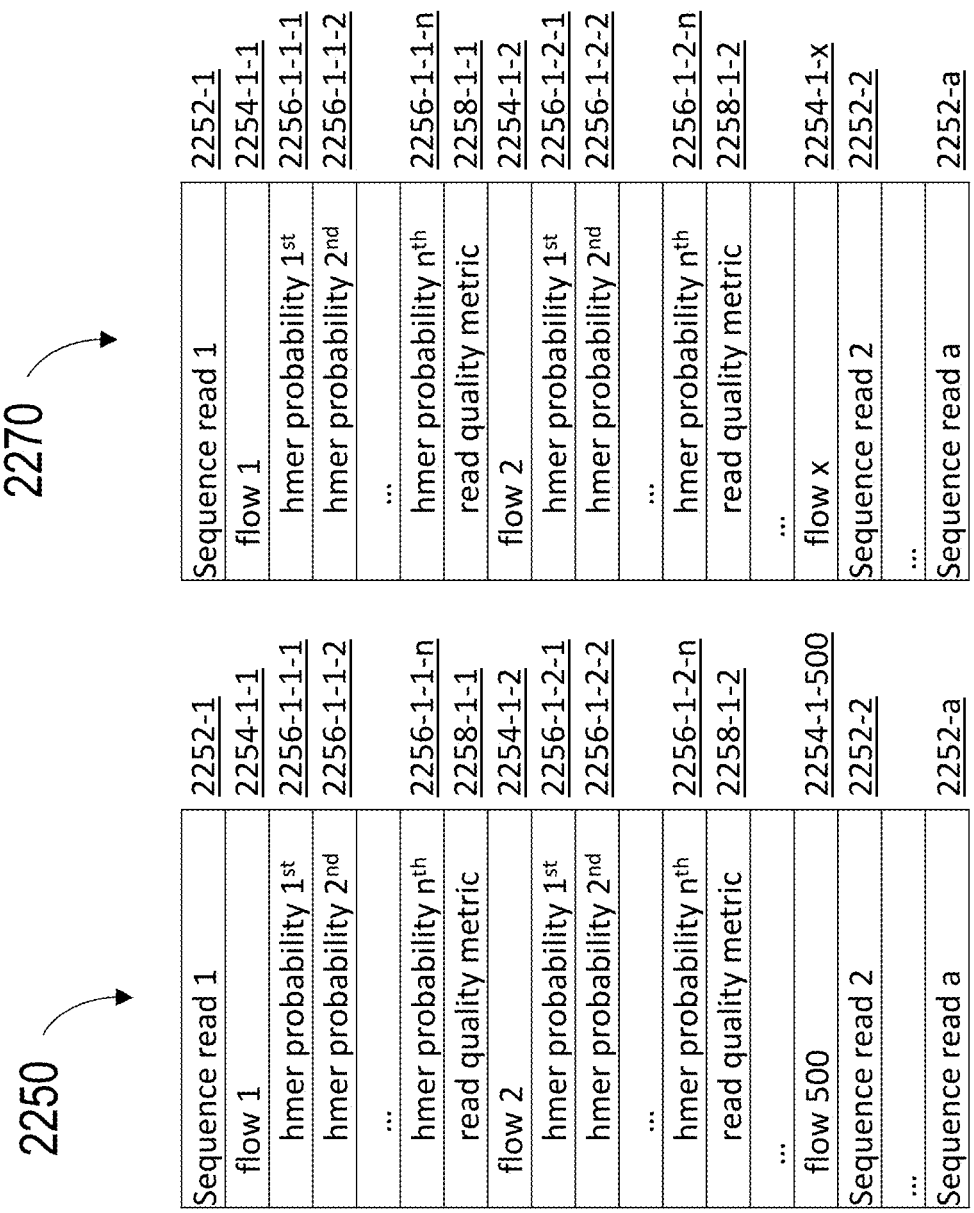
FIGS. 22B and 22C each illustrate an example block diagram of sequencing read data sets in accordance with embodiments described herein.

At block 2406, the system trims the terminus of one or more sequencing reads in the sequencing data based on the read quality metrics for a respective sequencing read, thereby generating trimmed sequencing data. With reference to FIGS. 22B and 22C, some of the sequencing reads are trimmed, thereby generating trimmed sequencing data.

In some embodiments, if a flow sequencing step produces a read quality metric below a predetermined threshold, the system can determine that deterioration has occurred in the sequencing read. Accordingly, the system can trim the sequencing read at or before the first flow sequencing step that produces a read quality metric below the threshold.

In some embodiments, the system uses an average of multiple read quality values to detect determination in the sequencing read. In some embodiments, the average is a moving average. Exemplary calculation of the moving average is described with reference to FIG. 25A. For example, at the third flow step, the system can calculate an average of RQM1, RQM2, and RQM3 (assuming the moving average is calculated using a sliding window of 3 flow steps); at the fourth flow step, the system can calculate an average of RQM2, RQM3, and RQM4. Thus, the moving average is a local quality measure.

In some embodiments, if the moving average exceeds a predetermined threshold, the system determines that deterioration (e.g., of read quality) has occurred and trims the sequencing read accordingly. In some embodiments, if a predefined number of moving averages are above the predetermined threshold, the system determines that deterioration has occurred. For example, the flow sequencing step that triggers trimming is the nth sequencing flow step having a moving average above a predetermined threshold, wherein n is a predefined number. That is, in some instances, the sequencing read is trimmed at the flow where the read quality moving average exceeds the predetermined threshold. In some instances, the sequencing read is trimmed at the nth-flow where the read quality moving average has exceeded the predetermined threshold. In some instances, trimming the sequencing read removes the indicated flow and all subsequent flows.

In some instances, the predetermined threshold is a fixed value that can be tuned. For example, the predetermined threshold can be set to an average quality of the first 100 flow steps in a flow sequencing method (e.g., based on an average read quality metric for each flow across all sequencing reads). In some embodiments, the predetermined threshold is around 0.3. In some embodiments, the predetermined threshold is about 0, 0.1, 0.2, 0.3, 0.4, or 0.5. In some embodiments, the predetermined threshold is a real number between any of 0, 0.1, 0.2, 0.3, 0.4, or 0.5. Likewise, the predetermined number n can be a tunable fixed value. For example, n can be set to 3, 5, 10, 15, or 20. In some instances, n is any whole number between 1 and 20.

V. Computer Systems

The present disclosure provides computer control systems that are programmed to implement methods of the disclosure. FIG. 22 shows a computer system 2201 that is programmed or otherwise configured to implement methods and systems of the present disclosure, such as performing nucleic acid sequence and sequence analysis.

The computer system 2201 includes a central processing unit (CPU, also "processor" and "computer processor" herein) 2205, which may be a single core or multi core processor, or a plurality of processors for parallel processing. The computer system 2201 also includes memory or memory location 2210 (e.g., random-access memory, read-only memory, flash memory), electronic storage unit 2215 (e.g., hard disk), communication interface 2220 (e.g., network adapter) for communicating with one or more other systems, and peripheral devices 2225, such as cache, other memory, data storage and/or electronic display adapters. The memory 2210, storage unit 2215, interface 2220 and peripheral devices 2225 are in communication with the CPU 2205 through a communication bus (solid lines), such as a motherboard. The storage unit 2215 may be a data storage unit (or data repository) for storing data. The computer system 2201 may be operatively coupled to a computer network ("network") 2230 with the aid of the communication interface 2220. The network 2230 may be the Internet, an internet and/or extranet, or an intranet and/or extranet that is in communication with the Internet. The network 2230 may be a telecommunication and/or data network. The network 2230 may include one or more computer servers, which may enable distributed computing, such as cloud computing. The network 2230, with the aid of the computer system 2201, may implement a peer-to-peer network, which may enable devices coupled to the computer system 2201 to behave as a client or a server.

The CPU 2205 may execute a sequence of machine-readable instructions, which may be embodied in a program or software. The instructions may be stored in a memory location, such as the memory 2210. The instructions may be directed to the CPU 2205, which may subsequently program or otherwise configure the CPU 2205 to implement methods of the present disclosure. Examples of operations performed by the CPU 2205 may include fetch, decode, execute, and writeback.

The CPU 2205 may be part of a circuit, such as an integrated circuit. One or more other components of the system 2201 may be included in the circuit. The circuit may be an application specific integrated circuit (ASIC).

The storage unit 2215 may store files, such as drivers, libraries and saved programs. The storage unit 2215 may store user data, e.g., user preferences and user programs. The computer system 2201 may include one or more additional data storage units that are external to the computer system 2201, such as located on a remote server that is in communication with the computer system 2201 through an intranet or the Internet.

The computer system 2201 may communicate with one or more remote computer systems through the network 2230. For instance, the computer system 2201 may communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user may access the computer system 2201 via the network 2230.

Methods as described herein may be implemented by way of machine (e.g., computer processor) executable code stored on an electronic storage location of the computer system 2201, such as, for example, on the memory 2210 or electronic storage unit 2215. The machine-executable or machine-readable code may be provided in the form of software. During use, the code may be executed by the processor 2205. The code may be retrieved from the storage unit 2215 and stored on the memory 2210 for ready access by the processor 2205. In some situations, the electronic storage unit 2215 may be precluded, and machine-executable instructions are stored on memory 2210.

The code may be pre-compiled and configured for use with a machine having a processer adapted to execute the code or may be compiled during runtime. The code may be supplied in a programming language that may be selected to enable the code to execute in a pre-compiled or as-compiled fashion.

While methods in accordance with the present disclosure have been disclosed above, more details as to the types of data that may be processed or provided by these methods are now described. FIGS. 22B-22C illustrate example block diagrams of sequencing read data sets in accordance with embodiments described herein. Sequencing data sets and methods of processing thereof are described in International Patent App. No. PCT/US2022/074056, which is herein incorporated by reference in its entirety.

FIG. 22B shows an example input sequencing read data set 2250. Input data set 2250 (e.g., comprising flow-based sequencing signal information for a plurality of sequencing reads) may include, for each sequencing read 2252 in the plurality of sequencing reads, for each sequencing flow 2254 in a plurality of sequencing flows, at least: i) at least two homopolymer (hmer) probabilities 2256 (e.g., each hmer probability represents a likelihood of a particular number (h) of consecutive nucleic acids of a single base type being detected for a respective flow), and ii) a read quality metric 2258, where the read quality metric is determined from the hmer probabilities. The plurality of sequencing reads comprises a number a of sequencing reads. In this example input data set 2250, the total number of sequencing flows is 500. As described elsewhere herein, a total number of sequencing flows may be any desired number. In some embodiments, an hmer probability is computed for each sequencing read, for each sequencing flow, for each value of h from 0-12. In some embodiments, an hmer probability is computed for each sequencing read, for each sequencing flow, for each value of h from 0-11, from 0-10, from 0-9, from 0-8, from 0-7, from 0-6, from 0-5, or from 0-4.

FIG. 22C shows an example of a trimmed or filtered sequencing read data set 2270. Trimmed data set 2270 is derived from input sequencing data set 2250 and comprises much of the same information (e.g., sequencing flows and homopolymer probabilities) for each sequence read. However, in FIG. 22C one or more sequence reads have been trimmed. That is, in one or more sequence reads, one or more sequencing flows have been determined to have a read quality metric below a predetermined threshold and have been discarded, as described herein. In some instances, for a respective sequencing read, all subsequent sequencing flows after the one or more sequencing flows with read quality metrics below the predetermined threshold are discarded (or trimmed). Thus, the one or more trimmed sequencing reads will have a different number of remaining sequencing flow steps than the total number of sequencing flows.

Aspects of the systems and methods provided herein, such as the computer system 2201, may be embodied in programming. Various aspects of the technology may be thought of as "products" or "articles of manufacture" typically in the form of machine (or processor) executable code and/or associated data that is carried on or embodied in a type of machine-readable medium. Machine-executable code may be stored on an electronic storage unit, such as memory (e.g., read-only memory, random-access memory, flash memory) or a hard disk. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2201 may include or be in communication with an electronic display 2235 that comprises a user interface (UI) 2240 for providing, for example, imaging results or results of nucleic acid sequencing (e.g., sequence reads, consensus sequences, etc.). Examples of UI's include, without limitation, a graphical user interface (GUI) and web-based user interface.

Methods and systems of the present disclosure may be implemented by way of one or more algorithms. An algorithm may be implemented by way of software upon execution by the central processing unit 2205. The algorithm can, for example, implement methods of the present disclosure.

EXAMPLES

Certain examples of the following examples illustrate various methods of making linkers and labeled substrates described herein. It is understood that one skilled in the art may be able to make these compounds by similar methods or by combining other methods known to one skilled in the art. It is also understood that one skilled in the art would be able to make other compounds in a similar manner as described below by using the appropriate starting materials and modifying synthetic routes as needed. In general, starting materials and reagents can be obtained from commercial vendors or synthesized according to sources known to those skilled in the art or prepared as described herein.

Unless otherwise noted, reagents and solvents used in synthetic methods described herein are obtained from commercial suppliers. Anhydrous solvents and oven-dried glassware may be used for synthetic transformations sensitive to moisture and/or oxygen. Yields may not be optimized. Reaction times may be approximate and may not be optimized. Materials and instrumentation used in synthetic procedures may be substituted with appropriate alternatives. Column chromatography and thin layer chromatography (TLC) may be performed on reverse-phase silica gel unless otherwise noted. Nuclear magnetic resonance (NMR) and mass spectra may be obtained to characterize reaction products and/or monitor reaction progress.

Example 1

Figure 5:
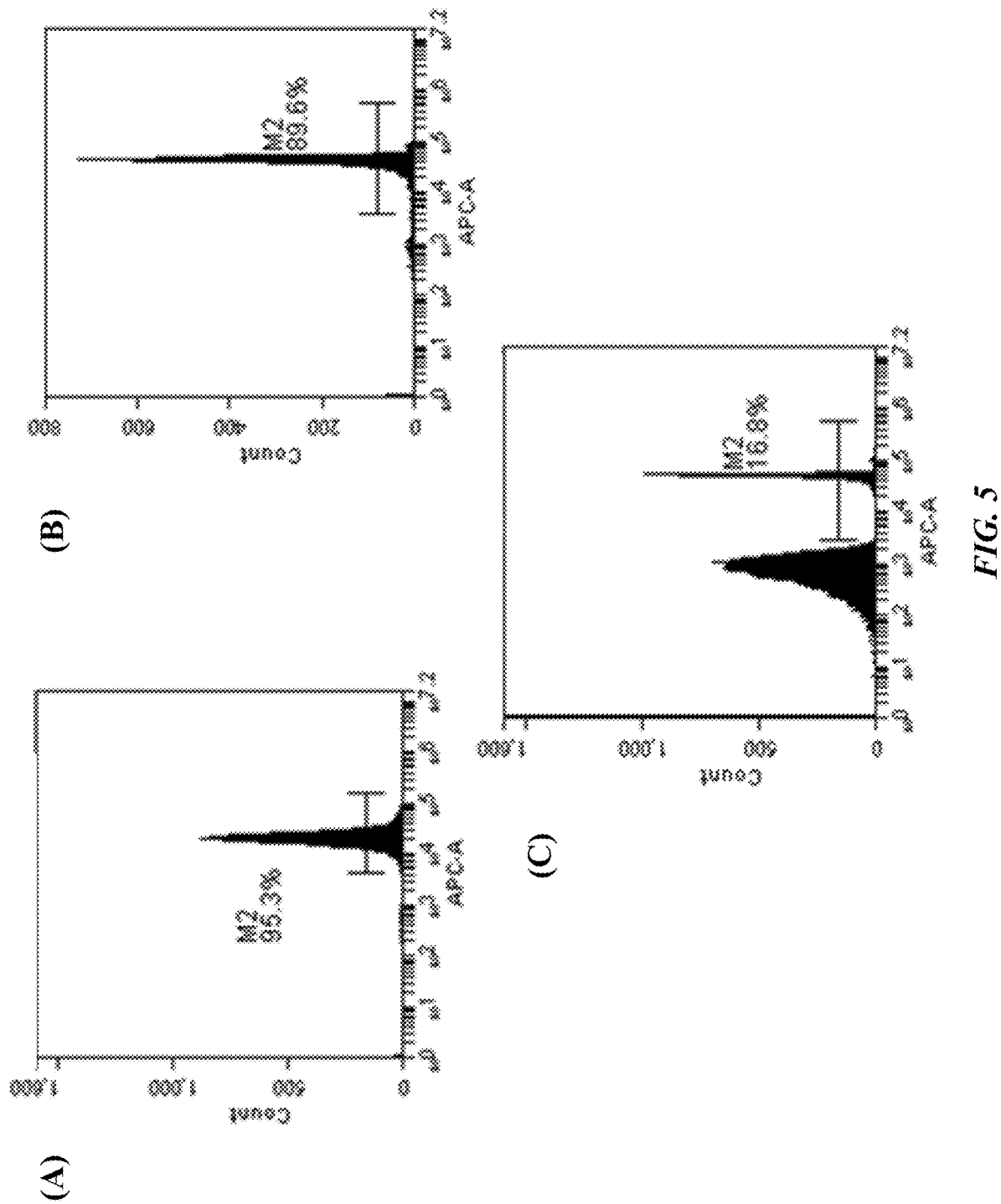
FIG. 5 shows in Panel (A) an *E. coli* library that was subjected to pre-enrichment procedures, in Panel (B) an artificial template library that was subjected to pre-enrichment procedures, and in Panel (C) an artificial template library that was subjected to control procedures (in absence of pre-enrichment), each graph showing a distribution of count vs. allophycocyanin (APC) fluorescence.

Table 1 below and FIG. 5 show the results of amplification using pre-enrichment (e.g., enriching a mixture of supports (e.g., beads), prior to clonal amplification, to use isolated and/or concentrated extended support mixtures for amplification) procedures against control procedures in absence of performing pre-enrichment procedures. Amplification was performed on *E. coli* Library templates and artificial templates.

TABLE 1

| Pre-enrichment vs Control Results | | | | |
|---|---|---|---|---|
| Process | Template | % Enrichment | % Amplification | % Polyclonal |
| Pre-enrichment | *E. coli* Library | 5 | 95 | N/A |
| Pre-enrichment | Artificial templates | 1.6 | 90 | 13.25 |

TABLE 1-continued

Pre-enrichment vs Control Results

| Process | Template | % Enrichment | % Amplification | % Polyclonal |
|---|---|---|---|---|
| Control | Artificial templates | N/A | 17 | 11 |

FIG. 5 shows in Panel (A) an *E. coli* library that was subjected to pre-enrichment procedures, in Panel (B) an artificial template library that was subjected to pre-enrichment procedures, and in Panel (C) an artificial template library that was subjected to control procedures (in absence of pre-enrichment). Each graph shows a distribution of count vs. allophycocyanin (APC) fluorescence. In each panel, the horizontal axis depicts fluorescence intensity levels (in log scale) and the vertical axis depicts the number of beads at certain intensity levels. Amplified beads are shown with higher intensity levels. As shown in Panel (A), the *E. coli* library (pre-enrichment) resulted in 5% enrichment (against a theoretical 10%), and 95.3% of total fluorescence intensity attributed to amplified beads. As shown in Panel (B), the artificial template library (pre-enrichment) resulted in 1.6% enrichment (against a theoretical 10%), and 89.6% of total fluorescence intensity from amplified beads. As shown in Panel (C), the artificial template library (control) resulted in only 16.8% of total fluorescence intensity from amplified beads. Approximately 13.25% of the pre-enrichment artificial template library population resulted in polyclonal amplification. Approximately 11% of the post-enrichment artificial template library population resulted in polyclonal amplification.

Example 2

Table 2 below summarizes data of pre-enrichment experiments based on the scheme depicted in FIG. 2A.

TABLE 2

Pre-enrichment by ligating template nucleic acid molecules to surface primers on beads

| Cleavable base type | Total beads (Millions) | Approximate [bead]: [template] | % of beads expected to be pre-enriched | % of beads actually pre-enriched |
|---|---|---|---|---|
| Uracil | 2079.8835 | 10:1 | 10% | 12.6 |
|  | 1741.4775 |  | 10% | 10.6 |
|  | 1779.96 |  | 10% | 10.8 |
|  | 1834.121 |  | 10% | 11.1 |
|  | 2032.938 |  | 10% | 12.3 |
|  | 1554.9435 |  | 10% | 9.4 |
| Ribo-nucleotide | 376.936 | 10:1 | 10% | 4.79 |
|  | 360.877 |  | 10% | 4.59 |
|  | 361.513 |  | 10% | 5.95 |
|  | 321.2065 |  | 10% | 5.28 |

The enrichment conditions for these different pre-enrichment experiments are similar. Commercial ISP beads at 60M/uL were mixed with template nucleic acid molecules at about 6M/uL.

In some embodiments, a reaction mixture for these experiments has a final volume of 250 microliters into which 5 picomolar (pM) of the template nucleic acid (from artificial templates) was mixed with 6.00×10⁷ beads/μL in the presence of Taq DNA polymerase. The mixture is then incubated at 45 degrees Celsius for 1 hour.

To enrich the beads bound with templates, the 250 μL of ligation reaction was diluted in 750 uL reaction buffer and mixed with 250 μL of streptavidin magnetic beads. This mixture was mixed and incubated for 2 hours at room temperature. The template bound beads (e.g., either a single bead type or multiple types of beads) would have the magnetic beads attached and were selected by an appropriate magnet (or magnets) until the solution was clear (e.g., all the beads are removed from solution), and the supernatant was then removed. The beads are washed in buffer by gentle resuspension. Each wash is followed by a magnetization operation, in which the beads are magnetized on an appropriate magnet (or magnets) until the solution is clear, and the supernatant is removed.

The enriched beads can be eluted by enzymatic cleavage. The mix of amplification product containing uracils and magnetic beads was resuspended in 100 μL of buffer and incubated at 37 degrees Celsius for 30 minutes. In experiments where ribonucleotides or RNA bases were used in constructing the template nucleic acid molecules, RNase HII was added to the template bound beads and incubated at 37 degrees Celsius for 30 minutes. In experiments where uracil bases were used in constructing the template nucleic acid molecules, USER enzyme was added to the template bound beads and incubated at 37 degrees Celsius for 30 minutes. After enzyme cleavage of the RNA bases or uracils, template bounds beads were released from magnetic beads, leaving avidin bound to streptavidin on the magnetic beads.

Flow cytometry was used to quantify the input beads and the beads recovered after pre-enrichment. Pre-enrichment using strand dissociation without enzymatic cleavage results in 1.6% enrichment (against a theoretical 10%—e.g., a theoretical maximum of 10% of the beads can be bound to template strands since a 10× excess of beads are added to the template solution). In contrast, a cleavage protocol using USER cleavage of uracils (e.g., corresponding to the schematic depicted in FIG. 2A) resulted in about 10% of the input beads being recovered after pre-enrichment, close to the theoretical maximum and indicating high efficiency. RNase H treatment produced approximately a 5% of input beads being enriched. This suggests that an alternative approach corresponding to the schematic depicted in FIG. 2A (except RNA bases instead of uracils were included in the adapters) also worked, albeit at a lower efficiency. These cleavable moiety methods, thus, can produce results significantly superior to the dissociation method.

The enriched beads according to any of the protocols described above can be subsequently used in emulsion PCR procedures. Libraries that were pre-enriched on beads following the procedures described above were found to be functional for downstream purposes.

Example 3

Cleavable moieties may be useful during or following pre-enrichment (e.g., 102, 104) and enable, for example, removal or elution of a support-bound template nucleic acid molecule following capture and/or enrichment. One example of a cleavable moiety is a C3 linker, which may be suitable as a substrate for an endonuclease such as APE1.

To evaluate the activity of the APE1 enzyme on various substrates, the following two synthetic oligonucleotide substrates were used:

```
Oligo #1:
                                    (SEQ ID NO: 3)
5' ACGGTTTCTCCATGXCACCTCC
``` where X represents a C3 linker (also referred to as C3 spacer), and the third T residue from the 3' end is modified by attachment of fluorescein. This oligo was used together with its fully complementary partner, the unmodified Oligo #3 as described below.

Oligo #2, a hairpin-type oligo is shown in FIG. 6A, where Y is a dSpacer residue (FIG. 6B) and the first T residue from the top-right hand side (highlighted) is modified by attachment of fluorescein. Both oligos were obtained from IDT. The chemical structures of the two modified residues are shown below. The structure of the C3 linker is shown in FIG. 6C.

Figure 7:
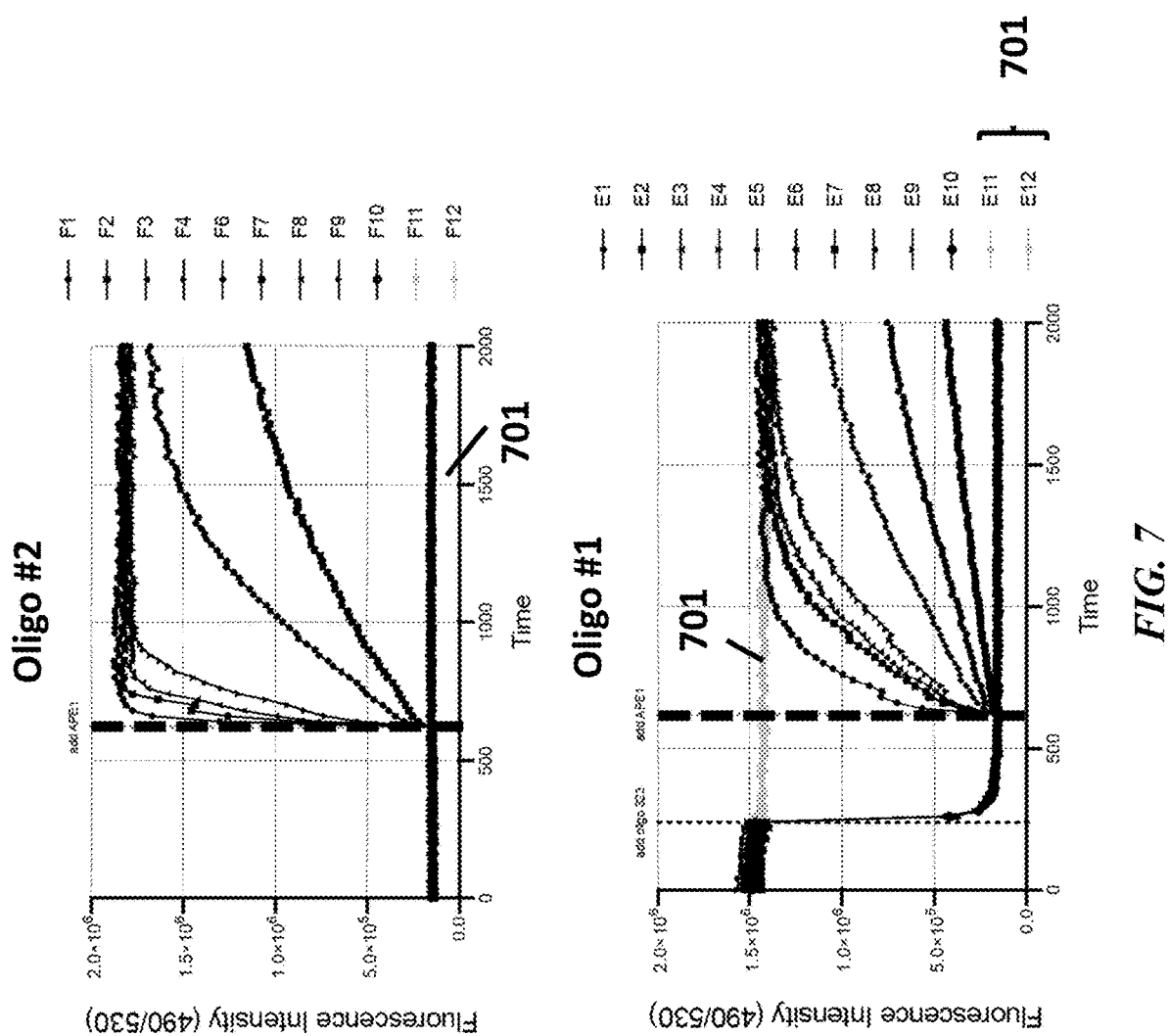
FIG. 7 illustrates example data of a cleavable moiety.

To perform the assay, 20 nM solutions of the two modified substrate oligos (Oligos #1 and #2) were prepared in 1× buffer 4 (NEB). Aliquots (50 µl) of these solutions were placed in individual wells of a 96 well plate and the plate was placed in a fluorescence plate reader, equilibrated at 37° C. The fluorescence emission of the fluorescein attached to the oligos was recorded continuously. To the wells containing the single-stranded Oligo #1 was added an excess of its complementary partner, Oligo #3 (the time of addition is indicated by a vertical black dotted line in FIG. 7). Upon formation of the double-stranded hybrid, the fluorescein of Oligo #1 is quenched and its intensity decreases. When a constant fluorescence level was reached, 2 µl of serial two-fold dilutions of the enzyme APE1 in buffer 4 were added to the first eight wells of each row of the plate (thick dotted line in the Figure). The highest final concentration of the enzyme (in wells E1 and F1, respectively) was 0.04 units/µl. No enzyme was added to wells E11, E12, F11, and F12 (701). The changes in fluorescence were recorded. An increase in fluorescence indicates successful cleavage of the substrates by APE1 at the modified positions. Such cleavage releases short, fluorescein labeled fragments (dSpacer-CTTCC and C3 linker-CACCTCC, respectively) which do not undergo quenching and are thus more highly fluorescent. As can be seen in FIG. 7, both oligos are functional substrates for the enzyme APE1, with the dSpacer-modified oligo #2 exhibiting somewhat faster cleavage kinetics than the C3 linker-containing hybrid of Oligos #1 and #3 (approx. 4-fold difference). In control experiments with oligonucleotides not containing the two linker moieties, no change in fluorescence was detected under identical conditions (not shown), thus demonstrating the specificity of the enzymatic reactions. In other experiments, it was also demonstrated that the APE1 enzyme is capable of cleaving at the C3 linker position within single-stranded oligos as well (not shown).

Example 4

In some instances, when attaching template nucleic acid molecules to supports (e.g., beads), a polymerase (e.g., Taq polymerase) and nucleotides (e.g., dNTPs) may be provided in addition to a ligase. Such a process may precede pre-enrichment; subsequent pre-enrichment efficiency may be calculated (e.g., amplifying sequences obtained from captured or enriched supports, counting the number of supports comprising amplified sequences, and normalizing to the number of starting supports). The pre-enrichment efficiency may be used to determine the ligation efficiency of the template nucleic acid molecules to the supports.

TABLE 3

Pre-enrichment efficiencies using a polymerase for attachment of template nucleic acid molecules to a support

| | MSB2FAM | | | PA30Atto | | | |
|---|---|---|---|---|---|---|---|
| | Count | CV FL1-A | Mean FL1-A | Count | Mean FL4-A | CV FL4-A | % amp |
| G01 B1273 std PE amp | 34,687 | 126.24% | 80,733.52 | 23,620 | 38,135.43 | 71.47% | 68.09 |
| G02 B1273 2 U Taq + dNTP amp | 44,196 | 128.10% | 76,538.00 | 36,667 | 35,488.12 | 72.79% | 82.96 |
| G03 B1273 10 U Taq + dNTP amp | 41,574 | 125.40% | 71,967.14 | 35,628 | 35,450.16 | 70.73% | 85.70 |
| G07 B1332 Std PE amp | 29,848 | 62.27% | 101,754.45 | 19,459 | 18,908.71 | 62.02% | 65.19 |
| G08 B1332 2 U Taq + dNTP amp | 33,422 | 71.28% | 96,319.17 | 24,356 | 14,907.46 | 58.87% | 72.87 |
| G09 B1332 10 U Taq + dNTP amp | 43,356 | 61.19% | 95,974.87 | 35,893 | 17,663.52 | 56.82% | 82.79 |
| G10 B1334 Std PE amp | 32,814 | 54.99% | 122,084.48 | 20,118 | 19,655.68 | 50.98% | 61.31 |
| G11 B1334 2 U Taq + dNTP amp | 40,919 | 54.60% | 110,189.26 | 30,334 | 19,254.32 | 51.34% | 74.13 |
| G12 B1334 10 U Taq + dNTP amp | 44,704 | 52.04% | 109,443.27 | 36,018 | 19,121.62 | 51.19% | 80.57 |

Table 3 illustrates example data of the pre-enrichment efficiencies (% amp) of bead samples (G01 to G03 and G07 to G12) with templates ligated thereto without Taq ("std PE amp") and with the addition of Taq polymerase at a concentration of 2 units or 10 units, along with nucleotides. B1273, B1332, and B1334 indicate different bead types. As seen in Table 3, the pre-enrichment efficiency (% amp) increases for multiple bead types (B31273, B1332, and B1334). For example, for B1273, the pre-enrichment efficiency, which may be indicative of the number of ligated templates to the beads, increases from 68.09% to 82.96% (for 2 units Taq) and 85.70% (for 10 units Taq). Similar increases in efficiency are perceived in the B1332 and B1334 beads.

Figure 8A:
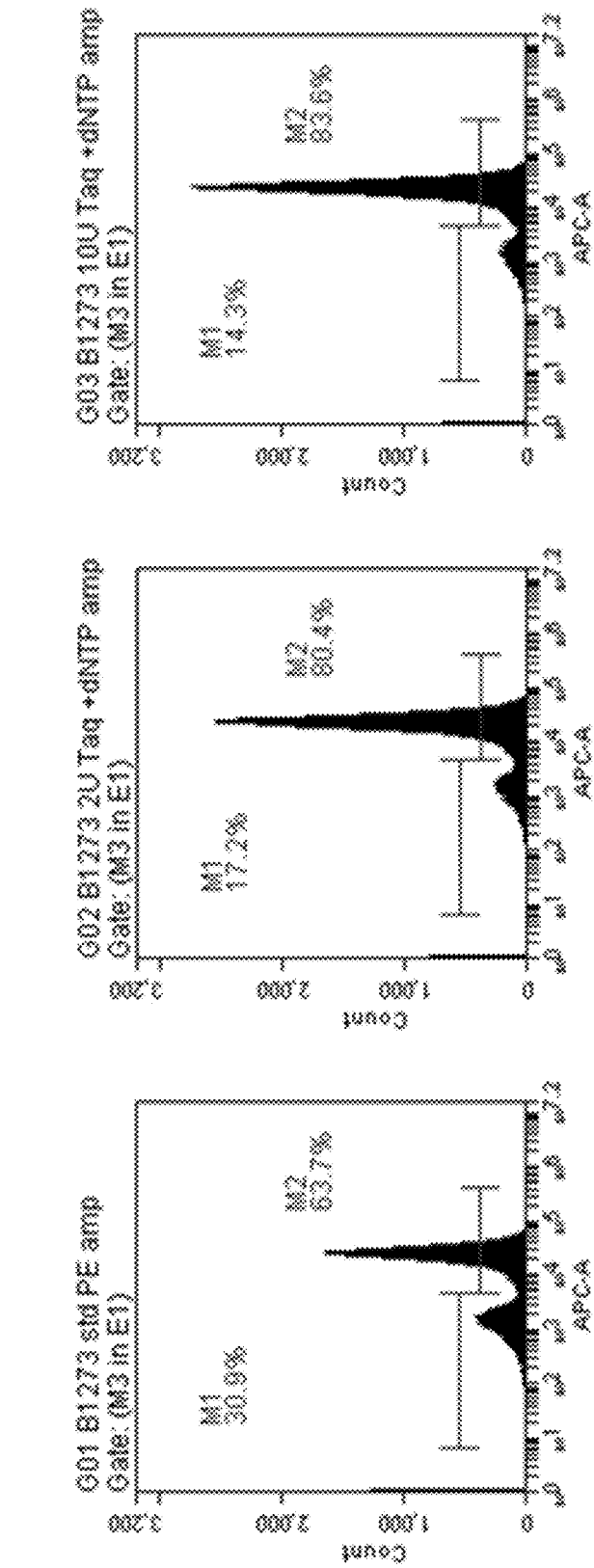
FIGS. 8A-8C illustrate example flow cytometry data demonstrating pre-enrichment efficiencies using a polymerase for attachment of template nucleic acid molecules to a support.
Figure 8B:
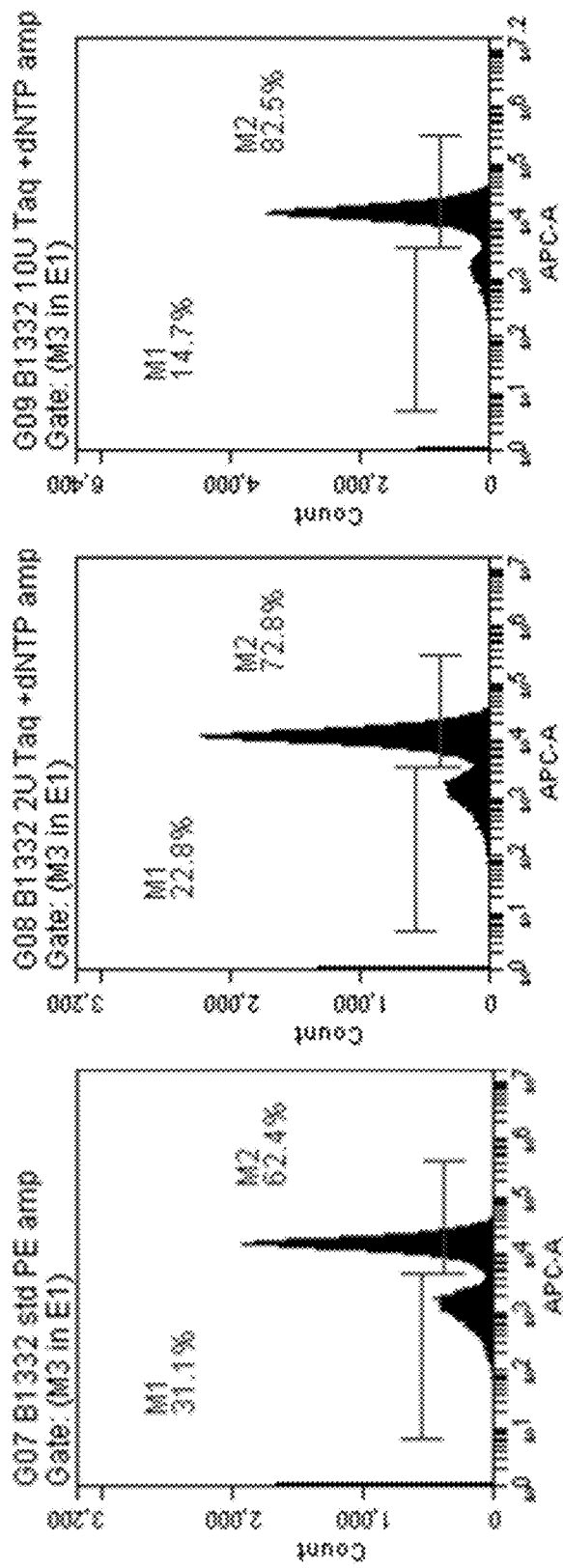
Figure 8C:
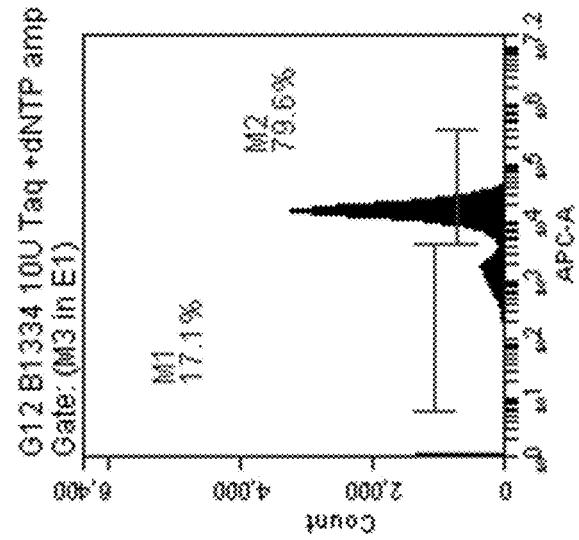
Figure 8C:
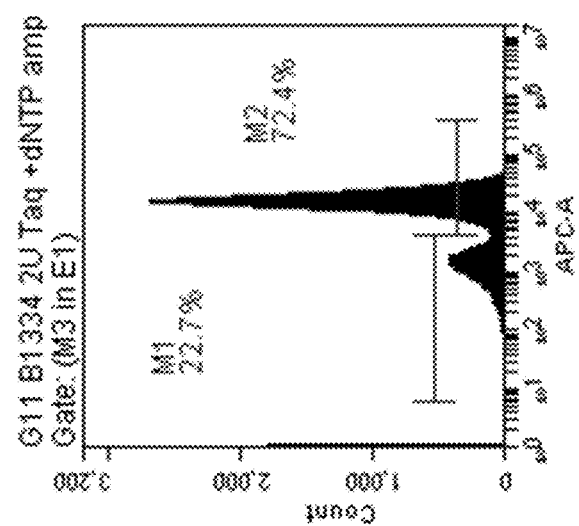
Figure 8C:
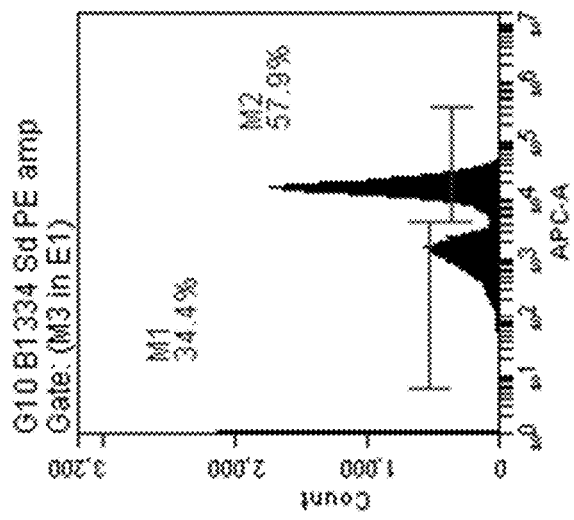

FIGS. 8A-8C show flow cytometry histograms (counts of fluorescence intensity of individual supports) of each bead type shown in Table 3. For each plot, the first peak (left-hand peak) indicates a non-amplified support (e.g., support lacking a template nucleic acid molecule ligated thereto), and the second peak (right-hand peak) indicates an amplified support. FIG. 8A shows flow cytometry results for bead B1273, FIG. 81B shows flow cytometry results for B1332, and FIG. 8C shows flow cytometry results for B1334.

beads). The bridge molecule and splint molecule, as shown in FIG. 10 may be provided at a known concentration that is lower than or approximately the same as the concentration

TABLE 4

Additional pre-enrichment efficiencies using a polymerase for attachment of template nucleic acid molecules to a support

| | PB30'FAM | | | | PA30Atto | | | | | Total | |
| --- | --- | --- | --- | --- | --- | --- | --- | --- | --- | --- | --- |
| | Count | Mean FL1-A | CV FL1-A | % aggr | Count | Mean FL4-A | CV FL4-A | % amp | [bead] | beads [M] | % recovery |
| H01 ePCR amp Std PE | 9,188 | 21,317.34 | 19.08% | 2.33 | 6,654 | 28,593.93 | 55.85% | 72.42 | 0.46 | 137.82 | 64.19 |
| H02 ePCR amp 50 uM dNTP | 12,557 | 21,087.55 | 20.09% | 3.10 | 9,065 | 27,692.90 | 57.05% | 72.19 | 0.63 | 188.36 | 74.94 |
| H03 ePCR amp 10 U Taq | 11,548 | 21,420.36 | 17.33% | 2.94 | 8,893 | 27,164.63 | 54.37% | 77.01 | 0.58 | 173.22 | 73.47 |
| H04 amp 10 U Taq + 50 um dNTP | 11,485 | 20,484.50 | 17.72% | 2.58 | 9,396 | 28,057.01 | 56.07% | 81.81 | 0.57 | 172.28 | 66.58 |
| H05 amp 20 U Taq + 50 um dNTP | 10,914 | 20,278.32 | 16.90% | 2.96 | 8,860 | 26,852.47 | 53.63% | 81.18 | 0.55 | 163.71 | 66.19 |
| H06 amp 50 U Taq + 50 um dNTP | 11,127 | 19,449.60 | 15.30% | 3.08 | 9,099 | 26,323.44 | 51.46% | 81.77 | 0.56 | 166.91 | 68.40 |

Figure 9:
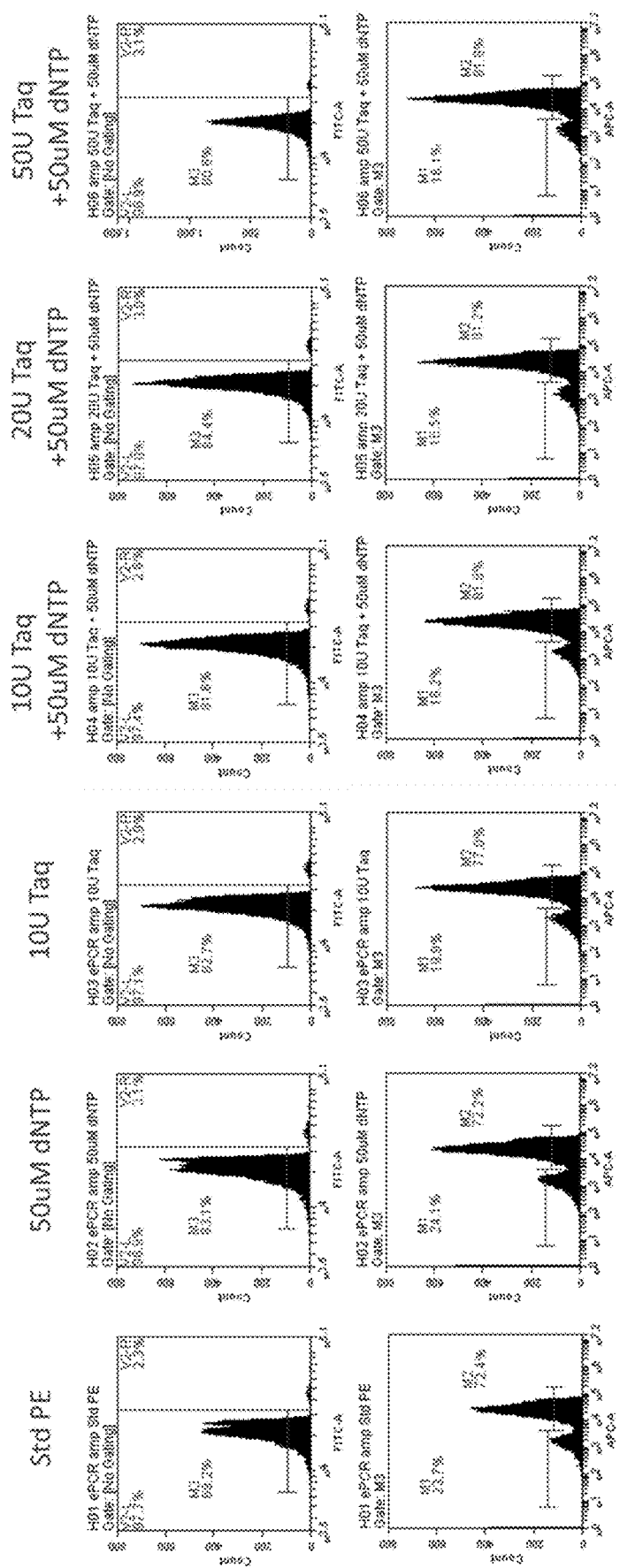
FIG. 9 illustrates additional example flow cytometry data demonstrating pre-enrichment efficiencies using a polymerase for attachment of template nucleic acid molecules to a support.

Table 4 illustrates additional example data of pre-enrichment efficiencies (% amp) of commercially available bead samples (H01 to H06) with templates ligated thereto with or without Taq and nucleotides. H01 has no nucleotides or Taq added ("Std PE amp"), which is a double-negative control; H02 has 50 micromolar nucleotides ("50 uM dNTP") but no Taq as a negative control; H03 has 10 units of Taq ("10 U Taq") with no nucleotides as a negative control; H04 has 10 units Taq and 50 micromolar of dNTPs added; H05 has 20 units Taq and 50 micromolar of dNTPs added; H06 has 50 units of Taq and 50 micromolar of dNTPs. As indicated in the pre-enrichment efficiency (% amp), the control groups (H01-H03) all have a pre-enrichment efficiency of 72-77%, whereas the groups with Taq and dNTPs have an increased pre-enrichment efficiency of 810%. FIG. 9 shows the flow cytometry histograms of the experimental groups shown in Table 4. Altogether, these results indicate that the addition of Taq polymerase and nucleotides may improve ligation efficiency of template nucleic acid molecules to supports.

Example 5

Template nucleic acid molecules may be attached to supports (e.g., beads) using an intermediary molecule, such as a splint oligonucleotide and/or a bridge molecule. An example workflow of using a splint and bridge molecule for attachment of a template nucleic acid molecule to a support is shown in FIG. 2E.

In some embodiments, the timing of the addition of splint molecules (and bridge molecules) to the reaction mix affects the speed of the reaction. In some embodiments, addition of the splint and bridge molecules during ligation will slow down the reaction (e.g., by slowing the reaction kinetics of template nucleic acid molecules attaching to supports). In some embodiments, the splint and bridge molecules are added to the reaction mix prior to ligation. This permits normalization of the ratio of template nucleic acid molecules to supports prior to the ligation reaction.

In an example, an excess of a template nucleic acid molecules may be provided as well as an excess of beads (e.g., at a 1:10 ratio of template nucleic acid molecules to of the template nucleic acid molecules. FIG. 11 shows an example of relative concentrations of a bridge molecule ("MS81-B2 Bridge"), a splint molecule ("MS82-PB28/B2 splint"), and the template nucleic acid molecules ("MSB2 library") in different experiments (S1-S7). The bridge and splint molecules may be provided at a concentration equivalent to or less than the concentration of the template nucleic acid molecules. The template nucleic acid molecules, splint molecules, and bridge molecules are hybridized to a support (e.g., bead) and optionally, ligated, to generate a plurality of support-template nucleic acid complexes. The support-template nucleic acid complexes are then pre-enriched (e.g., using a capture entity that can capture a sequence or capture moiety such as biotin), and the pre-enrichment percentage is calculated. As illustrated in FIG. 11, the enrichment percentages are as expected (~10%). The negative controls (S6 and S7) comprising either no splint (S6) or no splint and no bridge (S7) indicate a near-zero enrichment percentage, as expected. These results suggest that in the absence of the splint molecule, no template nucleic acid molecules ligate to the bead and thus no enrichment occurs, and that controlling the relative concentration of a splint and bridge molecule relative to the template nucleic acid molecules can determine the support-template nucleic acid molecule attachment ratio.

Such a process (e.g., controlling the relative ratios of the splint molecule, bridge molecule, and template nucleic acid molecules, and optionally, the support concentration), may be useful or advantageous in controlling the support-template nucleic acid molecule attachment, and thus the pre-enrichment ratio. Accordingly, in instances where the template nucleic acid molecule concentration is unknown (e.g., following amplification and cleavage of a cleavable moiety to render the molecule ligatable to the support), the attachment efficiency of the template nucleic acid molecule to the support may be controlled by determining the ratio of splints and bridges that are provided. In such an example, it may not be necessary to quantitate the template nucleic acid molecules present in a sample to enable efficient support attachment.

Example 6

Figure 12:
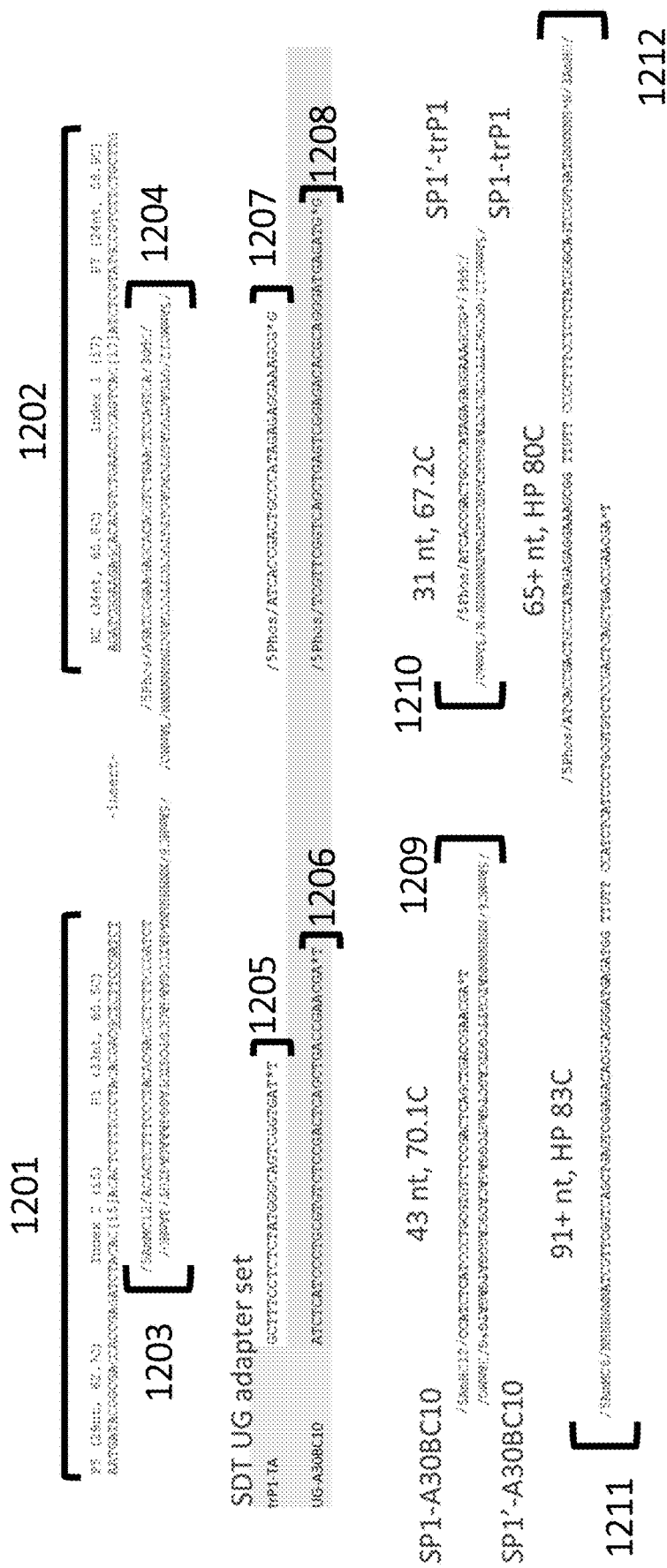
FIG. 12 illustrates example adapter sequences for generating template nucleic acid molecules (e.g., of a library of template nucleic acid molecules). Figure discloses SEQ ID NOS 4-8, 10, 9, 11-12, 14, 13, 15-16, 18, 17, 19-20 and 49, respectively, in order of appearance.

Adapter molecules may be attached to template sequence to generate template nucleic acid molecules. FIG. 12 shows example adapter sets (e.g., first adapters and second adapters) which may be ligated to a template sequence using a splint ligation approach (e.g., similar to the SPLAT or SRSLY approach), as described herein. The adapters may have the same or different annealing or melting temperatures, lengths and may comprise any number of useful functional sequences (e.g., primers such as index sequences, R1, R2, P5, P7 sequences, etc.) and functional moieties (e.g., blocking moieties, cleavable moieties, capture moieties). The adapters may comprise a random N-mer sequence which may be used to anneal the adapter to a portion of the template sequence.

Referring to FIG. 12, first and second adapters represented by segments 1203 and 1204 may be attached to a template sequence (the "insert") by ligating the two adapters to opposite ends of the template sequence. Additional primers, which may comprise one or more functional sequences, represented by segments 1201 and 1202, may be attached to the adapter-ligated template sequence, e.g., via hybridization and extension, to generate a template nucleic acid molecule.

Segment 1201 comprises functional sequences P5 (29 nt, 62.7° C.), Index 2 (i5), and R1 (33 nt, 65.5° C.):

```
                       (SEQ ID NOS 4-5, respectively, in order of appearance)
AATGATACGGCGACCACCGAGATCTACAC[i5]ACACTCTTTCCCTACACGACGCTCTTCCGAT
CT
``` respectively, in order of appearance) (24 nt, 58.9° C.):

Segment 1202 comprises functional sequences R2 (34 nt, 65.8° C.), Index 1 (i7), and P7 (24 nt, 58.9° C.):

```
                       (SEQ ID NOS 6-7, respectively, in order of appearance)
AGATCGGAAGAGCACACGTCTGAACTCCAGTCAC[i7]ATCTCGTATGCCGTCTTCTGCTTG
``` respectively, in order of appearance)

Below, segments 1203 and 1204 comprise a random N-mer sequence (e.g., NNNNNNN, where N represents a random base pair, e.g., adenine, guanine, cytosine, thymine).

Segment 1203 comprises atop strand comprising sequence:

```
                                                 (SEQ ID NO: 8)
/5AmMC12/ACACTCTTTCCCTACACGACGCTCTTCCGATCT
``` and a bottom strand comprising sequence:

```
                                                 (SEQ ID NO: 9)
/5AmMC6/NNNNNNNAGATCGGAAGAGCGTCGTGTAGGGAAAGAGTGT/
3AmMO/
```

Segment 1204 comprises atop strand comprising sequence:
```
                                                 (SEQ ID NO: 10)
/5Phos/AGATCGGAAGAGCACACGTCTGAACTCCAGTCA/3ddC/
``` and a bottom strand comprising sequence:

```
                                                 (SEQ ID NO: 11)
/5AmMC12/GTGACTGGAGTTCAGACGTGTGCTCTTCCGATCTNNNNNN
N/3AmMO/
```

Below shows the adapter set of 1205-1208.

Segment 1205 comprises sequence:

```
                                                 (SEQ ID NO: 12)
              GCTTTCCTCTCTATGGGCAGTCGGTGAT*T
```

Segment 1206 comprises sequence:

```
                                                 (SEQ ID NO: 13)
         ATCTCATCCCTGCGTGTCTCCGACTCAGCTGACCGAACGA*T
```

Segment 1207 comprises sequence:

```
                                                 (SEQ ID NO: 14)
         /5Phos/ATCACCGACTGCCCATAGAGAGGAAAGCG*G
```

Segment 1208 comprises sequence:

```
                                                 (SEQ ID NO: 15)
/5Phos/TCGTTCGGTCAGCTGAGTCGGAGACACGCAGGGATGAGATG*G
```

Below shows the adapter set of 1209-1210.

Segment 1209 (43 nt, 70.1° C.) comprises a top strand comprising sequence:

```
                                                 (SEQ ID NO: 16)
/5AmMC12/CCATCTCATCCCTGCGTGTCTCCGACTCAGCTGACCGAAC
GA*T
``` and a bottom strand comprising sequence:

```
                                                 (SEQ ID NO: 17)
/5AmMC6/NNNNNNNATCGTTCGGTCAGCTGAGTCGGAGACACGCAGGG
ATGAGATG*G/3AmMO/
```

Segment 1210 (31 nt, 67.2° C.) comprises a top strand comprising sequence:

```
                                                 (SEQ ID NO: 18)
         /5Phos/ATCACCGACTGCCCATAGAGAGGAAAGCGG*/3ddC/
``` and a bottom strand comprising sequence:

```
                                                 (SEQ ID NO: 19)
/5AmMC12/GCCGCTTTCCTCTCTATGGGCAGTCGGTGATNNNNNN*N/
3AmMO/
```

Below, segment 1211 (91+ nt, 83° C.) comprises sequence:

(SEQ ID NO: 49)
/5AmMC6/NNNNNNNATCGTTCGGTCAGCTGAGTCGGAGACACGCAGGG

ATGAGATGG TTUTT CCATCTCATCCCTGCGTGTCTCCGACTCAGCTG

ACCGAACGA*T

Segment 1212 (65+ nt, 80° C.) comprises sequence:

(SEQ ID NO: 21)
/5Phos/ATCACCGACTGCCCATAGAGAGGAAAGCGG TTUTT

CCGCTTTCCTCTCTATGGGCAGTCGGTGATNNNNNN*N/3AmMO

It will be appreciated that a sequence comprising a consecutive stretch of N bases may be of any and variable length.

For performing a ligation of the adapters, the materials may include: ET SSB (Extreme Thermostable Single-Stranded DNA Binding Protein), T4 DNA ligase, T4 DNA ligase buffer (e.g., comprising 50 mM Tris-HCl, 10 mM MgCl$_2$, 1 mM ATP, 10 mM DTT, at pH 7.5 at 25 degrees Celsius), T4 polynucleotide kinase, PEG-8000.
Protocol 1 nanogram of double-stranded DNA (dsDNA) may be provided. The ET SSB may be diluted in 10 mM Tris, pH 8 at a ratio of 1:62.5 to obtain a concentration of 8 ng/microliter. The dsDNA may be combined with 1 microliter often SSB, 10 mM Tris pH 8 to obtain 22 microliters, then incubated at 95 degrees Celsius for 3 minutes, then ice snap cooled for at least 2 minutes. Each adapter (e.g., N1NNNNN, where N represents a random base pair, e.g., adenine, guanine, cytosine, thymine) may be placed on ice and added to 1 microliter of 1 micromolar solution to obtain a 42 nanomolar concentration of the adapter. Master mix (e.g., PEG-8000 at 37%, T4 ligase buffer, T4 DNA ligase at 32 units/microliter, and T4 PNK at 0.4 units/microliter) may be added to total volume of 50 microliters and maintained on ice. The solution may be incubated at 37 degrees Celsius for 1 hour, then cleaned up (e.g., via a spin column) and eluted in 15 microliters of 10 mM Tris pH8. The resultant eluant may be amplified via PCR and cleaned up, e.g., using 1.2× AMPure clean, eluted in 20 microliters of 10 mM Tris pH 8.

Table 5 shows an example list of reagents and the final concentration and amounts for ligating adapters to a template sequence.

TABLE 5

List of reagents and final concentrations of reagents used for ligation of adapters to a template sequence.

| | Stock conc. | Final conc./ amount | Volume | Addition | |
|---|---|---|---|---|---|
| Final raction vol. | | | 50 ul | | |
| DNA prep vol. | | | 22 ul | | |
| DNA | 5 ng/ul | 5 ng | 1 ul | preMix 1 | 1 |
| ET SSB (diluted 1:62.5) | 8 ng/ul | 8 ng | 1 ul | preMix 1 | |
| 10 mM Tris pH8 | | | 20 ul | preMix1 | |
| Adapter 1 | 1 uM | 1 pmol | 1 ul | add to PM1 | 2 |
| Adapter 2 | 1 uM | 1 pmol | 1 ul | add to PM1 | 3 |
| Ligation Buffer | 10 X | 1 X | 5 ul | preMix2 | 4 |
| PEG-8000 | 50% | 18.5% v/v | 18.5 ul | preMix2 | |
| T4 DNA Ligase | 2000 U/ul | 800 U | 0.4 ul | | 6 |
| T4 PNK | 10 U/ul | 10 U | 1 ul | | 5 |
| Water | | | 1.1 ul | preMix2 | |
| Final raction vol. | | | 50 ul | | |
| DNA prep vol. | | | 17 ul | | |
| DNA | 5 ng/ul | 5 ng | 1 ul | preMix 1 | 1 |
| ET SSB (diluted 1:62.5) | 8 ng/ul | 8 ng | 1 ul | preMix 1 | |
| 10 mM Tris pH8 | | | 15 ul | preMix 1 | |
| Adapter 1 | 2 uM | 1 pmol | 0.5 ul | add to PM1 | 2 |
| Adapter 2 | 2 uM | 1 pmol | 0.5 ul | add to PM1 | 3 |
| Ligation Buffer | 10 X | 1 X | 5 ul | preMix2 | 4 |
| PEG-8000 | 37% | 18.5% v/v | 25 ul | preMix2 | |
| T4 DNA Ligase | 2000 U/ul | 800 U | 0.4 ul | | 6 |
| T4 PNK | 10 U/ul | 10 U | 1 ul | | 5 |
| Water | | | 0.6 ul | preMix2 | |

A splint ligation-based approach may also be used to attach a pair of adapters to a template sequence. FIG. 13A shows example adapters (1301 and 1302) which may be ligated to opposite ends of a template sequence to generate a precursor template nucleic acid molecule. Additional primers (1303 and 1304), which may comprise additional functional sequences (e.g., R1, R2, index sequences, etc.) may be attached to the precursor template nucleic acid molecule, e.g., via hybridization and extension, to generate a template nucleic acid molecule.

Segment 1304 comprises functional sequences P5 (29 nt, 62.7° C.), Index 2 (i5), and R1 (33 nt, 65.5° C.):

```
                        (SEQ ID NOS 4-5, respectively, in order of appearance)
AATGATACGGCGACCACCGAGATCTACAC[i5]ACACTCTTTCCCTACACGACGCTCTTCCGAT

CT
``` respectively, in order of appearance)

Segment 1303 comprises functional sequences R2 (34 nt, 65.8° C.), Index 1 (i7), and P7 (24 nt, 58.9° C.):

```
                        (SEQ ID NOS 6-7, respectively, in order of appearance)
AGATCGGAAGAGCACACGTCTGAACTCCAGTCAC[i7]ATCTCGTATGCCGTCTTCTGCTTG
``` respectively, in order of appearance)

Below, segments 1301 and 1302 comprise a random N-mer sequence (e.g., NNNNNNN, where N represents a random base pair, e.g., adenine, guanine, cytosine, thymine).

Segment 1302 comprises a top strand comprising sequence:

```
                                             (SEQ ID NO: 22)
          5'-ACACGACGCTCTTCCGATCT
``` and a bottom strand comprising sequence:

```
                                             (SEQ ID NO: 23)
          5'-NNNNNNNAGATCGGAAGAGCGTCGTGT
```

Segment 1301 comprises a top strand comprising sequence:

```
                                             (SEQ ID NO: 24)
          5'-P-AGATCGGAAGAGCACACGTC
``` and a bottom strand comprising sequence:

```
                                             (SEQ ID NO: 25)
5'-GACGTGTGCTCTTCCGATCTNNNNNNN-3'-aminoMod
```

The adapters may be prepared at a final concentration of 100 micromolar by dilution in 100 mM NaCl, 10 mM Tris-HCl (pH 8.0), 0.5 mM EDTA. Annealing may occur. Subsequently, the gDNA (template sequence) may be sheared to a size of ~300-400 base pairs and treated with bisulfite (e.g., Zymo gold). The adapter-template sequence complexes may be subjected to phosphorylation, e.g., by the addition of 100 ng of template DNA in 15 microliters with 5 units of PNK, T4 DNA ligase buffer for 15 minutes at 37 degrees Celsius, then 95 degrees Celsius for 3-5 minutes, then cooled in an ice bath. Ligation may then be performed. For example, for 3'-end ligation, the first adapter, at a concentration of 10 micromolar, may be added (30 microliter volume) to the template sequence with PEG4000 (5% w/v), 30 units of T4 DNA ligase, and incubated at 20 degrees Celsius for 1 hour. The molecule may then be purified (e.g., AMPure kit). The 5' end adapter may then be added, ligated, and then purified.

To test the efficiency of the adapter ligation using the SPLAT approach, two negative controls may be used as a comparison: (i) no template sequence and (ii) no adapters. The adapters may also be titrated (e.g., 0.5, 1, 5 nanograms). The expected results in such case may include "clean" controls (e.g., no DNA detected in the negative controls), and a higher concentration of adapters resulting in a greater number of DNA molecules detected.

Figures 13B, 13C:
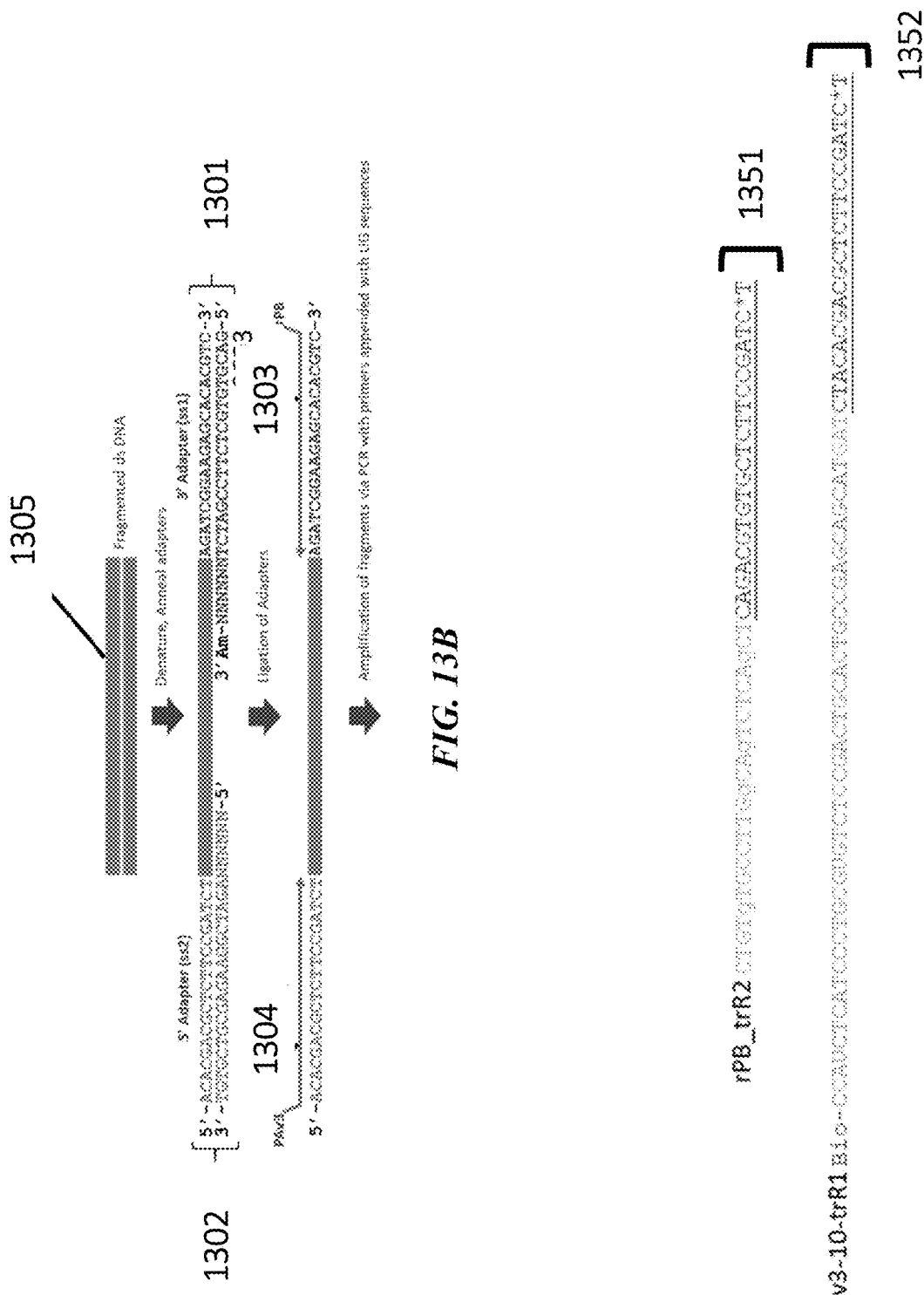
FIG. 13B shows an example workflow for generating a template nucleic acid molecule.
FIG. 13C shows example primers.

FIG. 13B shows another example of an adapter ligation approach. A template sequence 1305 (e.g., a fragmented double-stranded DNA molecule) may be denatured to generate a single-stranded template sequence and contacted with a first adapter (1301) and a second adapter (1302). The adapters (1301 and 1302) may comprise a random N-mer sequence, which may be used to anneal the adapters to a portion of the single-stranded template sequence. The adapters may comprise other moieties (e.g., capture moieties, blocking groups, etc.). The adapters may be ligated to the single-stranded template sequence. Additional primers (1303 and 1304) comprising sequences (e.g., trR1 (truncated R1), trR2 (truncated R2)) complementary to at least a portion of the first and second adapters (1301 and 1302) may be provided. Subsequent extension or amplification may be performed to generate template nucleic acid molecules, which may be further processed (e.g., subjected to pre-enrichment, sequencing, etc.).

FIG. 13C shows example primers (e.g., 1303 and 1304) comprising capture moieties (e.g., biotin), and other primer sequences (e.g., R1, trR1 (truncated R1), R2, trR2 (truncated R2)), which may be used to generate template nucleic acid molecules. The primers may comprise sequences that are complementary to sequences of the first and second adapters. Segment 1351 comprises sequence:

```
                                             (SEQ ID NO: 26)
CTGTGTGCCTTGGCAGTCTCAGCTCAGACGTGTGCTCTTCCGATC*T
```

Segment 1352 comprises sequence:
Biotin—

```
                                             (SEQ ID NO: 27)
Biotin-CCAUCTCATCCCTGCGUGTCTCCGACTGCACTGCCGAGCAGC

ATGATCTACACGACGCTCTTCCGATC*T
```

Figure 13D:
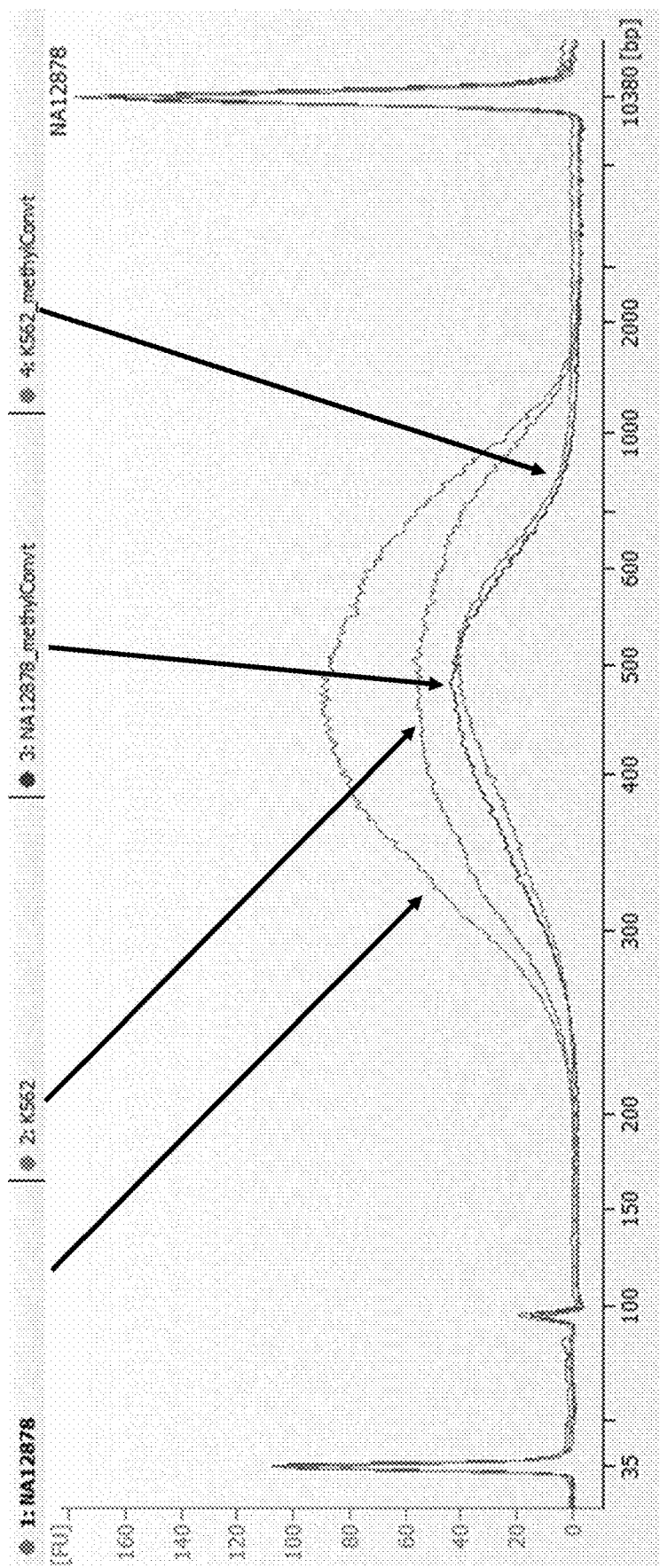
FIG. 13D shows example data resulting from the workflow of FIG. 13B. Figure discloses SEQ ID NOS 4-7, 22, 24, 50-51, 22, 52, 50, 53, 22, 52 and 26-27, respectively, in order of appearance.

FIG. 13D shows example data from the adapter ligation approach described above. The plot shows the fluorescence intensity as a function of nucleic acid length (base pairs). From left to right, the arrows point to the plots for NA12878, K562, NA12878_methylConvt, and K562_methylConvt. K562 and NA12878 represent commercially available cell samples that are used for extraction of genomic DNA for preparation of a library or template nucleic acid molecules. The traces from the plot illustrate successful preparation of a library of template nucleic acid molecules following amplification.

Example 7

Template nucleic acid molecules may be generated by ligating adapters to template sequences (also referred to herein as "insert" sequences) using, e.g., a SRSLY or SPLAT approach. In one example, ligation of adapters to template sequences may be useful in epigenetic analysis (e.g., DNA methylation analysis) of a sample (e.g., DNA sample). A DNA sample may be fragmented (e.g., enzymatically or mechanically) and subjected to conditions sufficient to convert methylated cytosines to uracils to generate template sequences comprising uracil. The template sequences comprising uracil may then be ligated to adapters, optionally comprising barcode sequences to generate template nucleic acid molecules. The template nucleic acid molecules may optionally be coupled to a bead. The template nucleic acid molecules may be sequenced to determine a degree of methylation in the DNA sample.

Figure 14:
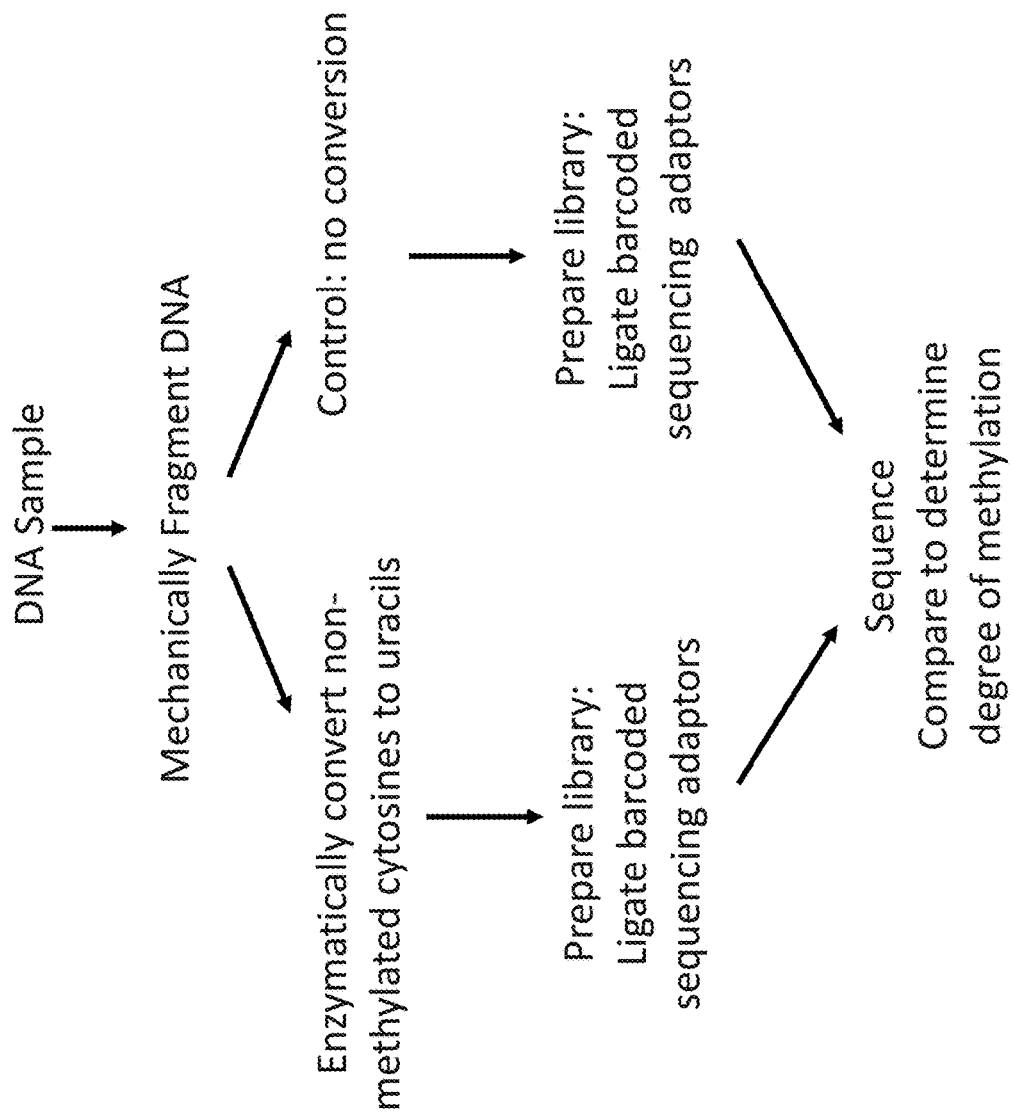
FIG. 14 shows an example workflow for analysis of a nucleic acid sample.

FIG. 14 shows an example workflow for epigenetic analysis of a sample. A DNA sample may be mechanically fragmented and separated into two groups: a sample group and a control group. The sample group may be enzymatically treated (e.g., with a cytosine deaminase) to convert non-methylated cytosines to uracils. Subsequently, library preparation may be performed, which may comprise ligating barcoded adapters comprising sequencing primers, and then sequencing the sample group to determine a degree of methylation. The control group may be non-treated (e.g., not converted), but subjected to the same library preparation and sequencing operations as the sample group. A comparison of the respective sequencing results of the sample group and the control group may indicate the degree of methylation of the DNA sample.

Figure 15:
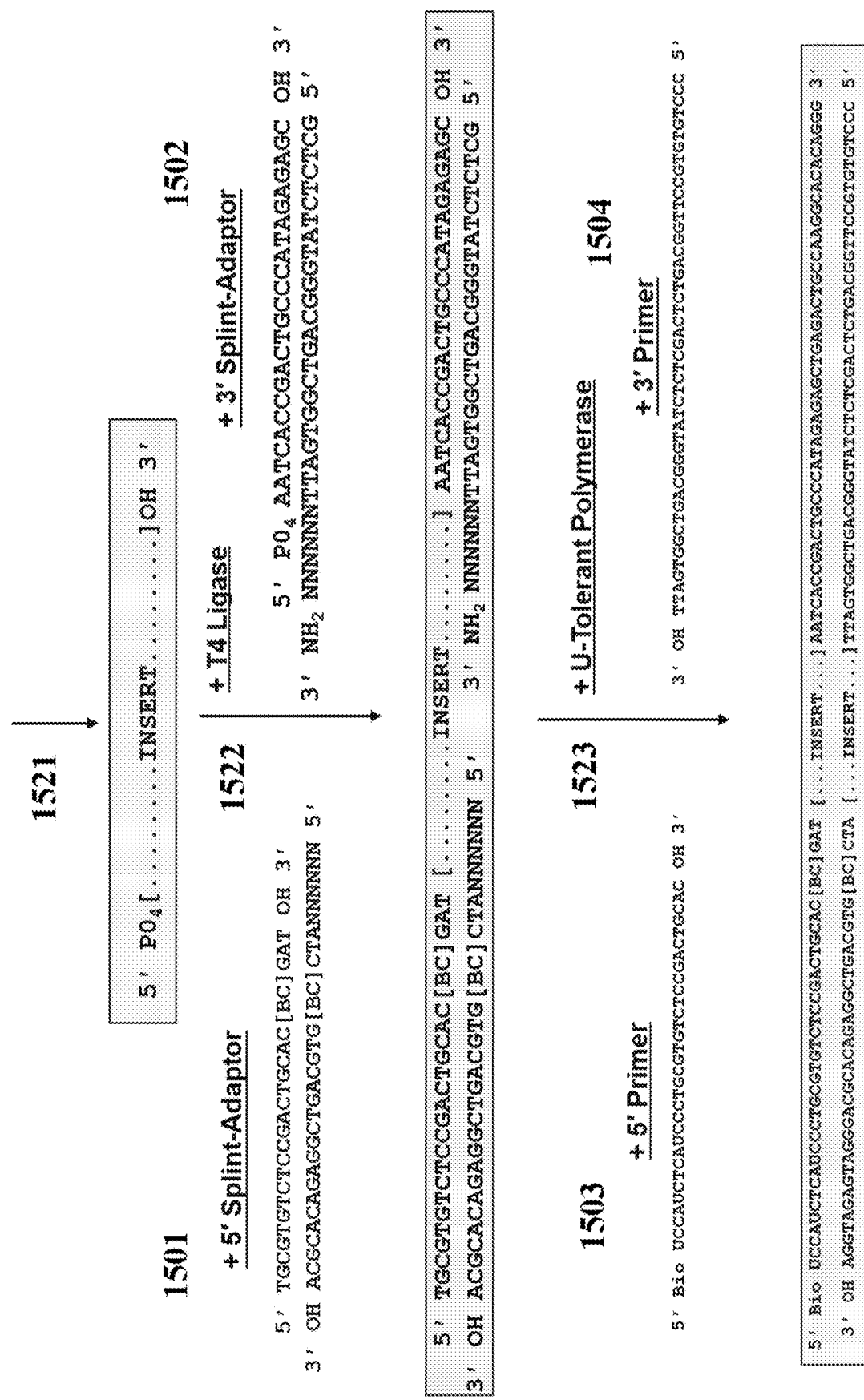
FIG. 15 shows an example workflow of generating a template nucleic acid molecule (e.g., of a library of template nucleic acid molecules) comprising a barcode sequence. Figure discloses SEQ ID NOS 30, 28, 31, 29, 54, 85, 31, 29 and 32-37, respectively, in order of appearance.
Figure 16:
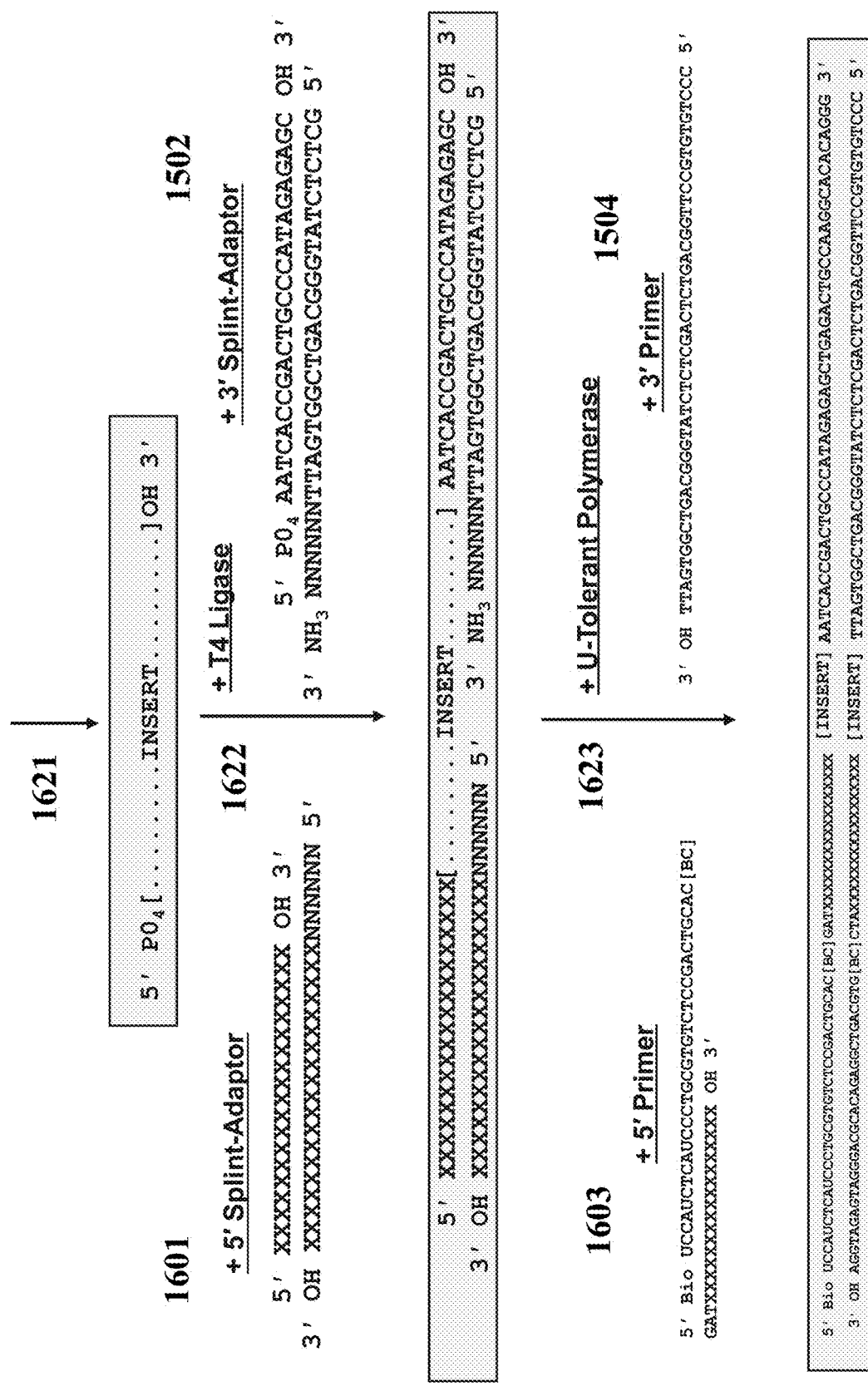
FIG. 16 shows another example workflow of generating a template nucleic acid molecule comprising a barcode sequence. Figure discloses SEQ ID NOS 28-29, 55, 84, 56, 33 and 57-60, respectively, in order of appearance.

FIGS. 15-17 illustrate examples of generating template nucleic acid molecules, e.g., for DNA analysis. The template nucleic acid molecules may be a part of a library of template nucleic acid molecules.

FIG. 15 shows an example of generating template nucleic acid molecules using partially double-stranded, barcoded adapters. A DNA sample may be subjected to fragmentation (e.g., Covaris® shearing) and optionally, enzymatic conversion of non-methylated cytosines to uracils (e.g., for methylation or epigenetic analysis). End polishing may be performed using a kinase, e.g., T4 PNK, which may phosphorylate a 5' end of the fragmented DNA molecule (or template sequence, also referred to herein as an "insert" molecule) and/or de-phosphorylate a 3' end of the fragmented DNA molecule (1521). An intermediary of the following structure (or at least order of segments thereof):

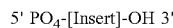
5' PO$_4$-[Insert]-OH 3' may be generated. A pair of adapters, such as a first adapter and a second adapter described herein, may be ligated to the fragmented DNA molecule. In one example, a first adapter 1502 ("3' splint adapter") may comprise an overhang sequence (e.g., random N-mer) and optionally, a blocking moiety, e.g., an amino group, which may prevent ligation of the first adapter to other first adapters. Thus, the first adapter 1502 may comprise a first strand with the following structure (or at least order of segments thereof):

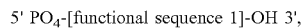
5' PO$_4$-[functional sequence 1]-OH 3', and a second strand with the structure (or at least order of segments thereof):

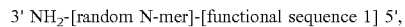
3' NH$_2$-[random N-mer]-[functional sequence 1] 5', where the functional sequences are any functional sequence described herein and at least a portion of the [random N-mer] is an overhang. A second adapter 1501 ("5' splint adapter") may comprise an overhang sequence (e.g., random N-mer) and may comprise a barcode sequence (denoted as "BC"). Thus, the second adapter 1501 may comprise a first strand with the structure (or at least order of segments thereof):

5' [functional sequence 2]-[BC]-[functional sequence 3]-OH 3', and a second strand with the structure (or at least order of segments thereof):

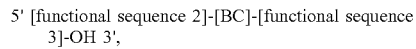
3' OH-[functional sequence 2]-[BC]-[functional sequence 3]-[random N-mer] 5', where the functional sequences are any functional sequence described herein and at least a portion of the [random N-mer] is an overhang. It will be appreciated that in the structural formulas described throughout this Example, for simplicity, a particular segment and its complementary segment (e.g., in the other strand) are described by the same segment descriptor: e.g., [functional sequence 2] in first strand and [functional sequence 2] in second strand are complementary sequences to each other.

In other examples, the first adapter may be single-stranded and may be annealed to a first splint molecule (e.g., bottom strand) comprising (i) a complementary sequence to a sequence of the first adapter and/or second adapter, and (ii) a sequence that binds to the template insert, and the second adapter may be single-stranded and may be annealed to a second splint molecule that may be the same or different from the first splint molecule.

The first adapter and the second adapter may be ligated to the fragmented DNA molecule (e.g., using a T4 ligase) to generate an adapter-ligated template nucleic acid molecule (1522). An intermediary with a first strand of the following structure (or at least order of segments thereof):

5' [functional sequence 2]-[BC]-[functional sequence 3]-[insert]-[functional sequence 1]-OH 3' bound on the 5' end and 3' end to two strands of the following structures (or at least order of segments thereof), respectively:

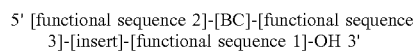
3' OH-[functional sequence 2]-[BC]-[functional sequence 3]-[random N-mer] 5'

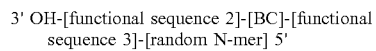
3' NH$_2$-[random N-mer]-[functional sequence 1] 5' may be generated. Optionally, the adapter-ligated template nucleic acid molecules may be amplified, e.g., using a polymerase that accepts uracils, and a pair of primers, such as a 5' primer 1503 and a 3' primer 1504, which comprise sequences corresponding to at least a portion of the first and second adapters, to generate a template nucleic acid molecule (1523). The 5' primer 1503 may comprise the following structure (or at least order of segments thereof):

5' [functional sequence 4]-[functional sequence 2]-OH 3', optionally with a biotin on the 5'. The 3' primer 1504 may comprise the following structure (or at least order of segments thereof):

3' OH-[functional sequence 1]-[functional sequence 5] 5'.

As described elsewhere herein, the adapters or primers may comprise additional useful moieties, e.g., excisable moieties, blocking moieties, capture moieties, etc. A template nucleic acid molecule comprising a strand of the following structure (or at least order of segments thereof):

5' [functional sequence 4]-[functional sequence 2]-
[BC]-[functional sequence 3]-[insert]-[functional sequence 1]-[functional sequence 5] 3' and/or its reverse complement, may be generated.

As shown in FIG. 15, first adapter 1502 ("3' splint adapter") comprises the following sequences in the top strand bottom strand, respectively:

(SEQ ID NO: 28)
5' PO$_4$ AATCACCGACTGCCCATAGAGAGC OH 3'

(SEQ ID NO: 29)
3' NH$_2$ NNNNNNTTAGTGGCTGACGGGTATCTCTCG 5'

Second adapter 1501 ("5' splint adapter") comprises the following sequences in the in the top strand bottom strand, respectively:

(SEQ ID NO: 30)
5' TGCGTGTCTCCGACTGCAC[BC]GAT OH 3'

(SEQ ID NO: 31)
3' OH ACGCACAGAGGCTGACGTG[BC]CTANNNNNN 5'

The 5' primer 1503 comprises the following sequence:

(SEQ ID NO: 32)
5' Bio UCCAUCTCAUCCCTGCGTGTCTCCGACTGCAC OH 3'

The 3' primer 1504 comprises the following sequence:

(SEQ ID NO: 33)
3' OH TTAGTGGCTGACGGGTATCTCTCGACTCTGACGGTTCCGTGTG TCCC 5'

The template nucleic acid molecule after PCR comprises the following sequence structure, in the top strand and bottom strand respectively:

(SEQ ID NOS 34-35, respectively, in order of appearance)
5' Bio UCCAUCTCAUCCCTGCGTGTCTCCGACTGCAC[BC]GAT[Insert]

AATCACCGACTGCCCATAGAGAGCTGAGACTGCCAAGGCACACAGGG 3' respectively, in order of appearance)

(SEQ ID NOS 36-37, respectively, in order of appearance)
3' OH AGGTAGAGTAGGGACGCACAGAGGCTGACGTG[BC]CTA[Insert]

TTAGTGGCTGACGGGTATCTCTCGACTCTGACGGTTCCGTGTGTCCC 5' respectively, in order of appearance)

In this workflow, the 5' splint adapter may be barcode specific and amino blockers may prevent self-ligation of the 3' splint adapters. Beneficially, any sequence added between the barcode sequence and the insert sequence (e.g., [functional sequence 3]: e.g., "GAT"/"CTA") is minimal (e.g., less than 5 bases, 4 bases, 3 bases, 2 bases, 1 bases, none), and provides for efficient sequencing of meaningful segments. Further both adapters may be added in a single step.

FIG. 16 shows another example of generating template nucleic acid molecules using partially double-stranded adapters followed by addition of barcode sequences. Similar to the example of FIG. 15, FIG. 16 shows that a DNA sample may be subjected to fragmentation (e.g., Covaris® shearing) and optionally, enzymatic conversion of non-methylated cytosines to uracils (e.g., for methylation or epigenetic analysis). End polishing may be performed using a kinase, e.g., T4 PNK, which may phosphorylate a 5' end of the fragmented DNA molecule (or template sequence, also referred to herein as an "insert" molecule) and/or de-phosphorylate a 3' end of the fragmented DNA molecule (1621). An intermediary of the following structure (or at least order of segments thereof):

5' PO$_4$-[Insert]-OH 3' may be generated. A pair of adapters, such as a first adapter and a second adapter described herein, may be ligated to the fragmented DNA molecule. In one example, a first adapter 1502 ("3' splint adapter") may comprise an overhang sequence (e.g., random N-mer) and optionally, a blocking moiety, which may prevent ligation of the first adapter to other first adapters. The first adapter 1502 may correspond to that described with respect to FIG. 15. Thus, the first adapter 1502 may comprise a first strand with the following structure (or at least order of segments thereof):

5' PO$_4$-[functional sequence 1]-OH 3', and a second strand with the structure (or at least order of segments thereof):

3' NH$_2$-[random N-mer]-[functional sequence 1] 5', where the functional sequences are any functional sequence described herein and at least a portion of the [random N-mer] is an overhang. A second adapter 1601 ("5' splint adapter") may comprise an overhang sequence (e.g., random N-mer) and may comprise a universal sequence. Thus, the second adapter 1601 may comprise a first strand with the structure (or at least order of segments thereof):

5' [universal seq]-OH 3', and a second strand with the structure (or at least order of segments thereof):

3' OH-[universal seq]-[random N-mer] 5', where the functional sequences are any functional sequence described herein and at least a portion of the [random N-mer] is an overhang.

The first adapter and the second adapter may be ligated to the fragmented DNA molecule (e.g., using a T4 ligase) to generate an adapter-ligated template nucleic acid molecule (1622). An intermediary with a first strand of the following structure (or at least order of segments thereof):

5' [universal seq]-[insert]-[functional sequence 1]-OH 3' bound on the 5' end and 3' end to two strands of the following structures (or at least order of segments thereof), respectively:

3' OH-[universal seq]-[random N-mer] 5'

3' NH$_2$-[random N-mer]-[functional sequence 1] 5' may be generated. Optionally, the adapter-ligated template nucleic acid molecules may be amplified, e.g., using a polymerase that accepts uracils, and a pair of primers, such as a 5' primer 1603 and a 3' primer 1504, which comprise sequences corresponding to at least a portion of the first and second adapters, to generate a template nucleic acid molecule (1623). In some examples, one or more primers may comprise a barcode sequence and a complementary universal sequence, such that amplification with the one or more primers generates a template nucleic acid molecule comprising a barcode sequence. The 5' primer 1603 may comprise the following structure (or at least order of segments thereof):

5' [functional sequence 4]-[functional sequence 2]-[BC]-[functional sequence 3]-[universal seq]-OH 3', optionally with a biotin on the 5'. The 3' primer 1504 may comprise the following structure (or at least order of segments thereof):

3' OH-[functional sequence 1]-[functional sequence 5] 5'.

As described elsewhere herein, the adapters or primers may comprise additional useful moieties, e.g., excisable moieties, blocking moieties, capture moieties, etc. A template nucleic acid molecule comprising a strand of the following structure (or at least order of segments thereof):

5' [functional sequence 4]-[functional sequence 2]-[BC]-[functional sequence 3]-[universal seq]-[insert]-[functional sequence 1]-[functional sequence 5] 3' and/or its reverse complement, may be generated.

In this workflow, the 5' splint adapter may comprise a universal sequence, in contrast to being barcode specific as in FIG. 15, and amino blockers may prevent self-ligation of the 3' splint adapters. The 5' primer 1603 may comprise the barcode sequence such that the template nucleic acid molecule after amplification comprises the barcode sequence. Further both adapters may be added in a single step.

Figure 17A:
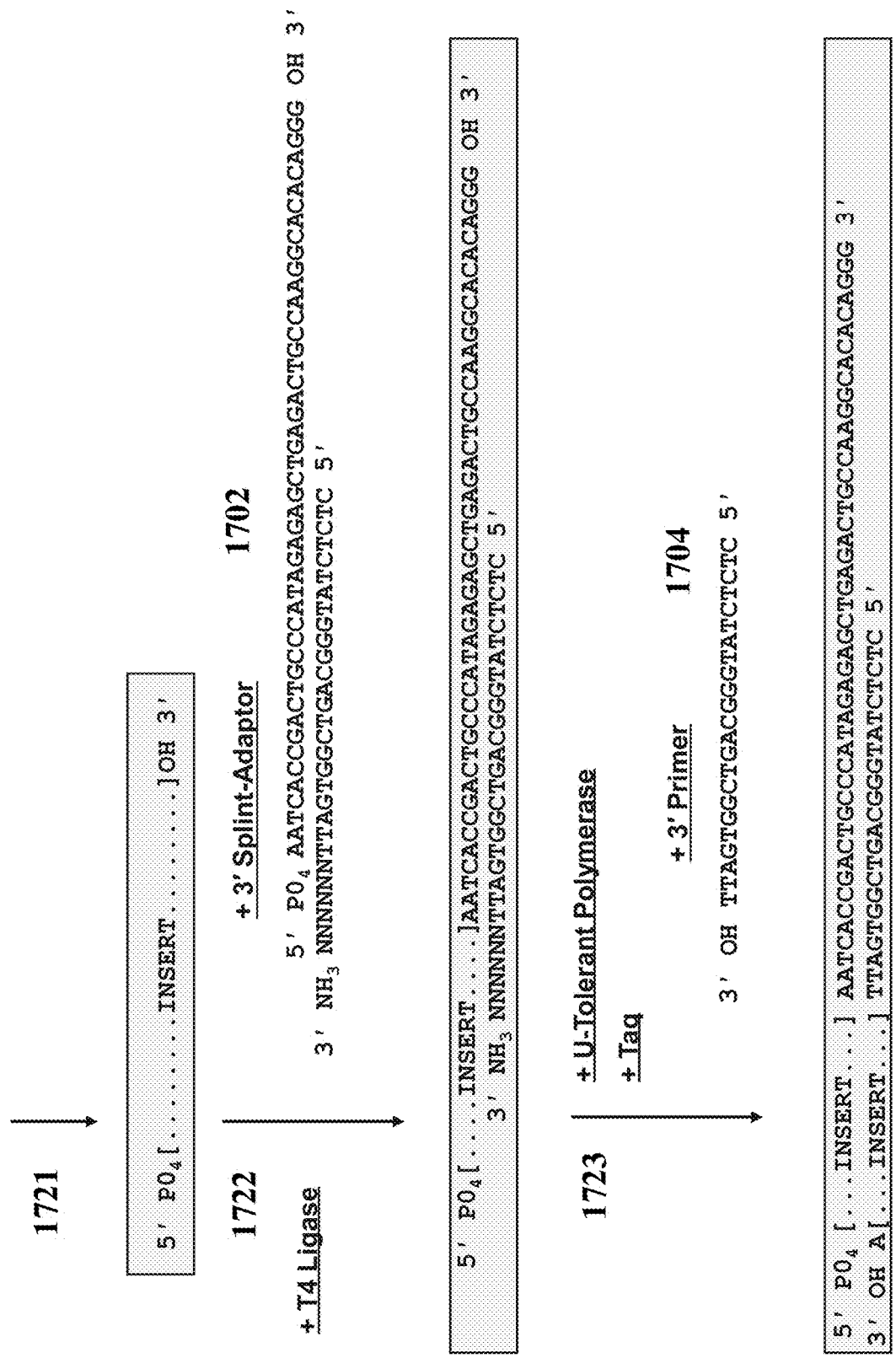
FIGS. 17A-17B show an example workflow for generating a template nucleic acid molecule comprising a barcode sequence using a multi-step approach.
Figure 17B:
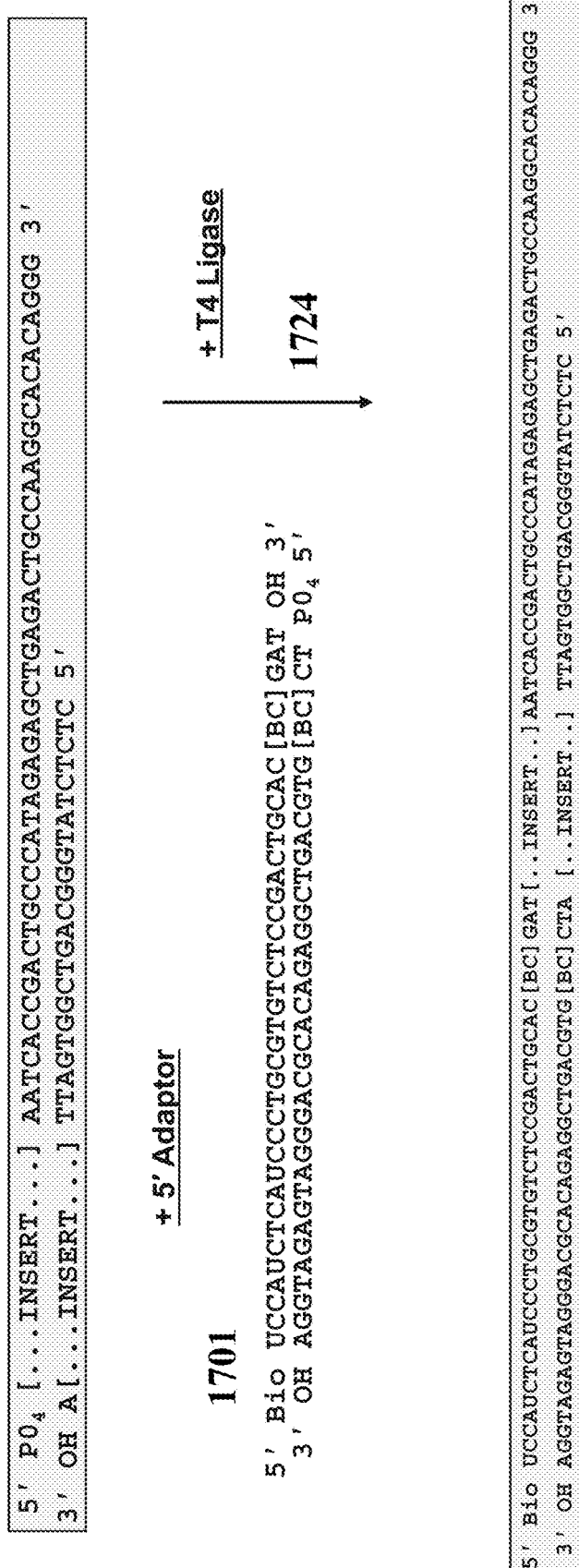

FIGS. 17A-17B shows another example of generating template nucleic acid molecules using a multi-step approach, which, in some instances, may obviate the need for amplification in order to generate the template nucleic acid molecules. In FIG. 17A, a DNA sample may be subjected to fragmentation (e.g., Covaris® shearing) and optionally, enzymatic conversion of non-methylated cytosines to uracils (e.g., for methylation or epigenetic analysis). End polishing may be performed using a kinase, e.g., T4 PNK, which may phosphorylate a 5' end of the fragmented DNA molecule (or template sequence, also referred to herein as an "insert" molecule) and/or de-phosphorylate a 3' end of the fragmented DNA molecule (1721). An intermediary of the following structure (or at least order of segments thereof):

5' PO$_4$-[Insert]-OH 3' may be generated. An adapter 1702 ("3' splint adapter") may be ligated to the fragmented DNA molecule. The adapter may comprise an overhang sequence (e.g., random N-mer) and optionally, a blocking moiety, which may prevent ligation of the adapter to other adapters. Thus, the adapter 1702 may comprise a first strand with the following structure (or at least order of segments thereof):

5' PO$_4$-[functional sequence 1]-[functional sequence 5]-OH 3', and a second strand with the structure (or at least order of segments thereof):

3' NH$_2$-[random N-mer]-[functional sequence 1] 5', where the functional sequences are any functional sequence described herein and at least a portion of the [random N-mer] is an overhang.

The adapter may be ligated to the fragmented DNA molecule (e.g., using a T4 ligase) to generate an adapter-ligated template nucleic acid molecule (1722). An intermediary with a first strand of the following structure (or at least order of segments thereof):

5' PO$_4$-[insert]-[functional sequence 1]-[functional sequence 5]-OH 3' bound to a second strand with the following structure (or at least order of segments thereof):

3' NH$_2$-[random N-mer]-[functional sequence 1] 5' may be generated.

The adapter-ligated template nucleic acid molecule may be hybridized to a primer 1704 ("3' primer") comprising a sequence that corresponds or is complementary to a sequence of the adapter 1702 (e.g., via denaturation of the adapter-ligated template nucleic acid molecule and re-annealing with the primer in excess). The 3' primer 1704 may comprise the following structure (or at least order of segments thereof):

3' OH-[functional sequence 1] 5'

Optionally, an extension reaction or amplification may be performed, e.g., using a polymerase that accepts uracil. In some instances, a Taq polymerase may be used to perform A-tailing on the amplified or extended product, thereby generating a precursor template nucleic acid molecule (1723). An intermediary with a first strand of the following structure (or at least order of segments thereof):

5' PO$_4$-[insert]-[functional sequence 1]-[functional sequence 5] 3' bound to a second strand with the following structure (or at least order of segments thereof):

3' OH-[A]-[insert]-[functional sequence 1] 5' may be generated.

As shown in FIG. 17B, a second adapter 1701 ("5' adapter"), optionally comprising a barcode sequence, may be ligated to the precursor template nucleic acid molecule to generate the template nucleic acid molecule (1724). The second adapter 1701 may comprise a first strand with the structure (or at least order of segments thereof):

5' [functional sequence 4]-[functional sequence 2]-[BC]-[functional sequence 3]-OH 3' optionally with a biotin on the 5', and a second strand with the structure (or at least order of segments thereof):

3' [functional sequence 4]-[functional sequence 2]-[BC]-[functional sequence 3]-PO$_4$ 5', where the functional sequences are any functional sequence described herein and at least a portion of the [random N-mer] is an overhang.

In this workflow, the 5' splint adapter may comprise a single, universal sequence amongst 5' splint adapters in contrast to being barcode specific as in FIG. 15, and amino blockers may prevent self-ligation of the 3' splint adapters. Furthermore, beneficially, any sequence added between the barcode sequence and the insert sequence (e.g., [functional sequence 3]: e.g., "GAT"/"CTA") is minimal (e.g., less than 5 bases, 4 bases, 3 bases, 2 bases, 1 bases, none), and provides for efficient sequencing of meaningful segments.

As described herein, the adapters or primers may additionally comprise useful moieties, e.g., excisable moieties, blocking moieties, capture moieties, etc. It will be appreciated that amino-blocking groups (e.g., NH$_2$) may be added to any unblocked 3' ends and/or 5' ends of any of the splint adapters described herein. For example, the second adapter 1701 and/or 5' primer's (1503, 1603) may comprise one or more uracil moieties, which may be excisable or cleavable, such as in [functional sequence 4]. The excisable moieties may be useful, for example, in generating an overhang sequence which may subsequently anneal to a sequence of a bead or support, as well as in cleaving off any capture moieties that may have been used for enrichment (e.g., pre-enrichment) purposes. The excision may be performed, for example, by performing an amplification to convert the uracil moieties to thymines and digesting using an enzyme (e.g., RNAse), an excising enzyme (e.g., UDG or USER), or by removing a strand (e.g., via denaturation or degradation) comprising the excisable moieties.

The methods described with respect to FIG. 15-17B may further comprise attaching the generated template nucleic acid molecule, or derivative thereof, to a support (e.g., bead, other substrate). This may be achieved via hybridizing a single-stranded portion of the generated template nucleic acid molecule or its derivative (e.g., an overhang generated from cleaving excisable moieties, the derivative is single-stranded, etc.) to an oligonucleotide comprising a complementary sequence (e.g., [functional sequence 4]) and ligating and/or extending. Alternatively, splints and/or bridge molecules described herein may be employed. The methods described with respect to FIG. 15-17B may further comprise pre-enrichment, in which bead-template assemblies are isolated from negative beads which did not bind to any template (or its derivatives). In some cases, a majority of beads may be bound to at most one template (or its derivative).

Figure 18:
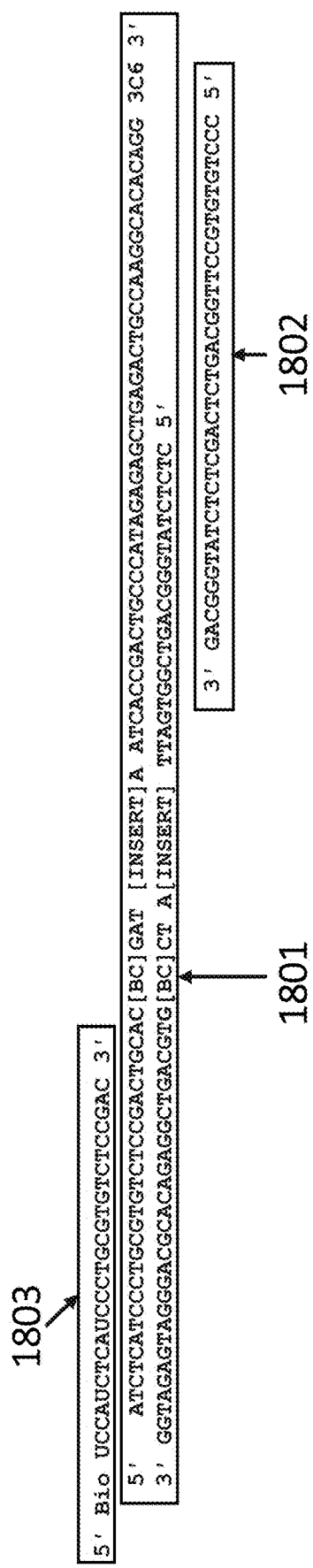
FIG. 18 shows an example of a precursor template nucleic acid molecule and primers for generating a template nucleic acid molecule. Figure discloses SEQ ID NOS 43, 38-39, 73-74 and 42, respectively, in order of appearance.

FIG. 18 shows an example of a precursor template nucleic acid molecule 1801 comprising a barcode sequence, which may be generated using one of the approaches described herein (e.g., as shown in FIGS. 15-17B). The precursor template nucleic acid molecule may be amplified using one or more primers, e.g., first primer 1802 and second primer 1803, optionally comprising additional moieties such as excisable moieties, capture moieties, etc. to generate a template nucleic acid molecule. The template nucleic acid molecule may subsequently be coupled to a bead or support, as described elsewhere herein. Precursor template nucleic acid molecule 1801 comprises the following sequences in the two strands, respectively:

First primer 1802 comprises the following sequence:

(SEQ ID NO: 42)
3' GACGGGTATCTCTCGACTCTGACGGTTCCGTGTGTCCC 5'

Second primer 1803 comprises the following sequence:

(SEQ ID NO: 43)
5' Bio UCCAUCTCAUCCCTGCGTGTCTCCGAC 3'

Figure 19:
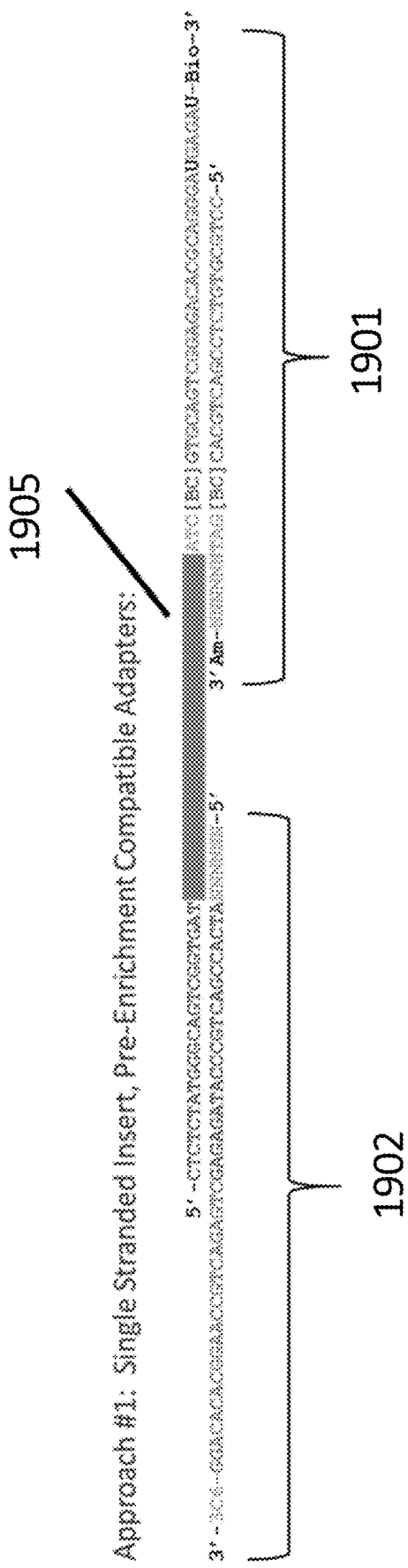
FIG. 19 shows an example of a template nucleic acid molecule comprising a barcode sequence. Figure discloses SEQ ID NOS 75-78, respectively, in order of appearance.

FIG. 19 shows another example of a template nucleic acid molecule which may be generated without the use of amplification. A template sequence 1905 may be ligated to a first adapter 1901 and a second adapter 1902. The first adapter 1901 may be a partially double-stranded molecule comprising an overhang sequence (e.g., random N-mer) and optionally, a blocking moiety, which may prevent ligation of the adapter to other adapters. The first adapter 1901 may optionally comprise other functional sequences or moieties, e.g., barcode sequences, blocking moieties, cleavable moieties (e.g., uracil), capture moieties (e.g., capture oligos, biotin molecules), etc. The second adapter 1902 may be a partially double-stranded molecule and may comprise an overhang sequence (e.g., random N-mer). The second adapter 1902 may optionally comprise other functional sequences or moieties.

Figure 20:
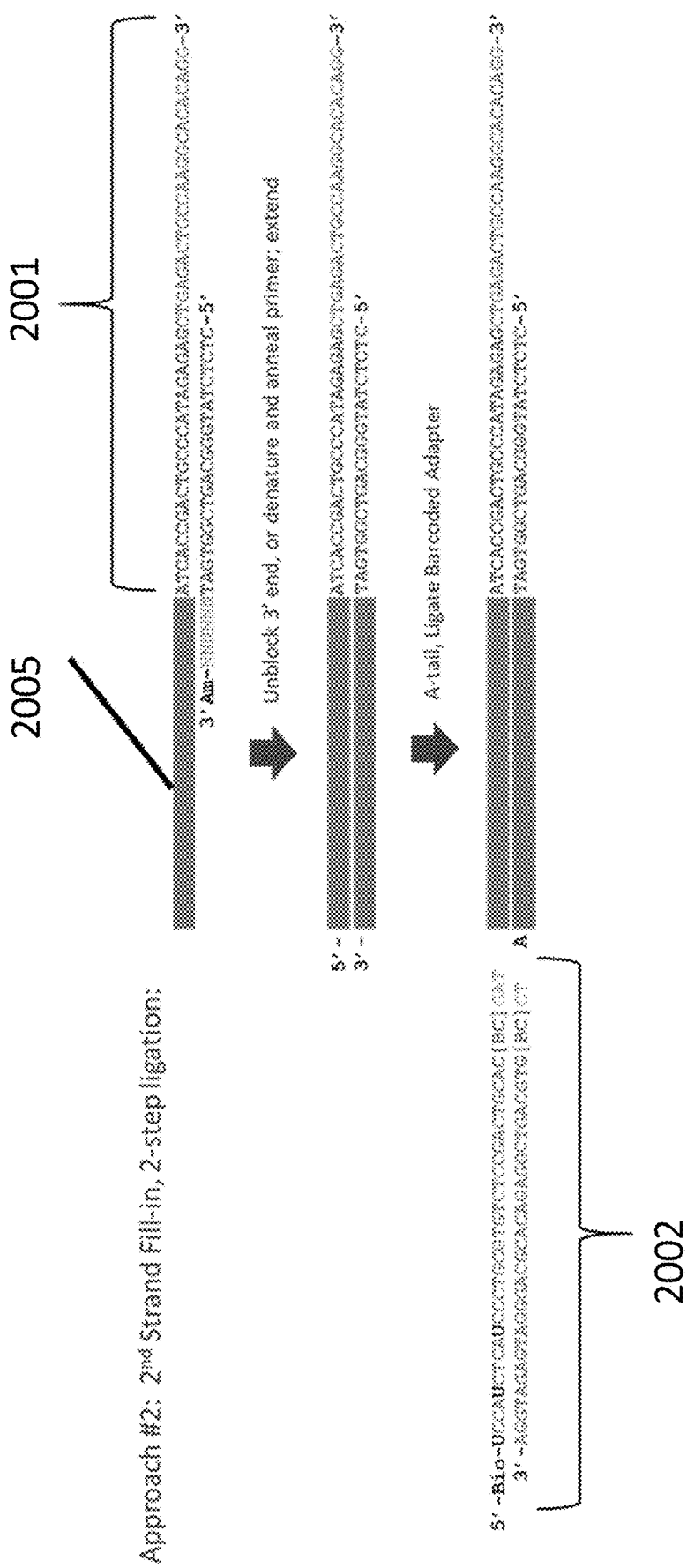
FIG. 20 shows an example workflow for generating a template nucleic acid molecule comprising a barcode sequence using a multi-step approach. Figure discloses SEQ ID NOS 79-80, 79, 75, 81, 79, 82 and 75, respectively, in order of appearance.

FIG. 20 shows another example workflow for generating template nucleic acid molecules, which, in some instances, may obviate the need for amplification during library preparation. A template sequence 2005 may be ligated to a first adapter 2001. The first adapter 2001 may be a partially double-stranded molecule comprising an overhang sequence (e.g., random N-mer) and optionally, a blocking moiety (e.g., a 3' amino group), may prevent ligation of the adapter to other adapters. Optionally, the first adapter 2001 may comprise functional sequences or moieties, e.g., barcode sequences, blocking moieties, cleavable moieties (e.g., uracil), capture moieties (e.g., capture oligos, biotin molecules), etc. Following ligation of the first adapter 2001 to the template sequence 2005, the blocking moiety may be removed, and the first adapter 2001 may be extended, using the template sequence 2005 as a template. Subsequent A-tailing may be performed, along with annealing and ligation of a second adapter 2002 to generate a template nucleic acid molecule. In some instances, the second adapter 2002 may comprise a thymine or poly-T sequence that may allow for annealing of the second adapter 2002 to a portion of the template sequence 2005 or complement thereof (e.g., an A-tail that is added at a 3' end opposite the template sequence 2005 strand). The first adapter 2001 or the second (SEQ ID NOS 38-39, respectively, in order of appearance)
5' ATCTCATCCCTGCGTGTCTCCGACTGCAC-[BC]-GAT-[INSERT]-A

ATCACCGACTGCCCATAGAGAGCTGAGACTGCCAAGGCACACAGG-3C6 3' respectively, in order of appearance)

(SEQ ID NOS 40-41, respectively, in order of appearance)
3' GGTAGAGTAGGGACGCACAGAGGCTGACGTG-[BC]-CT A-[INSERT]-

TTAGTGGCTGACGGGTATCTCTC 5' respectively, in order of appearance)

adapter 2002 may comprise additional functional sequences or moieties, e.g., cleavable moieties, capture moieties, barcode sequences, etc.

Example 8

Figure 23:
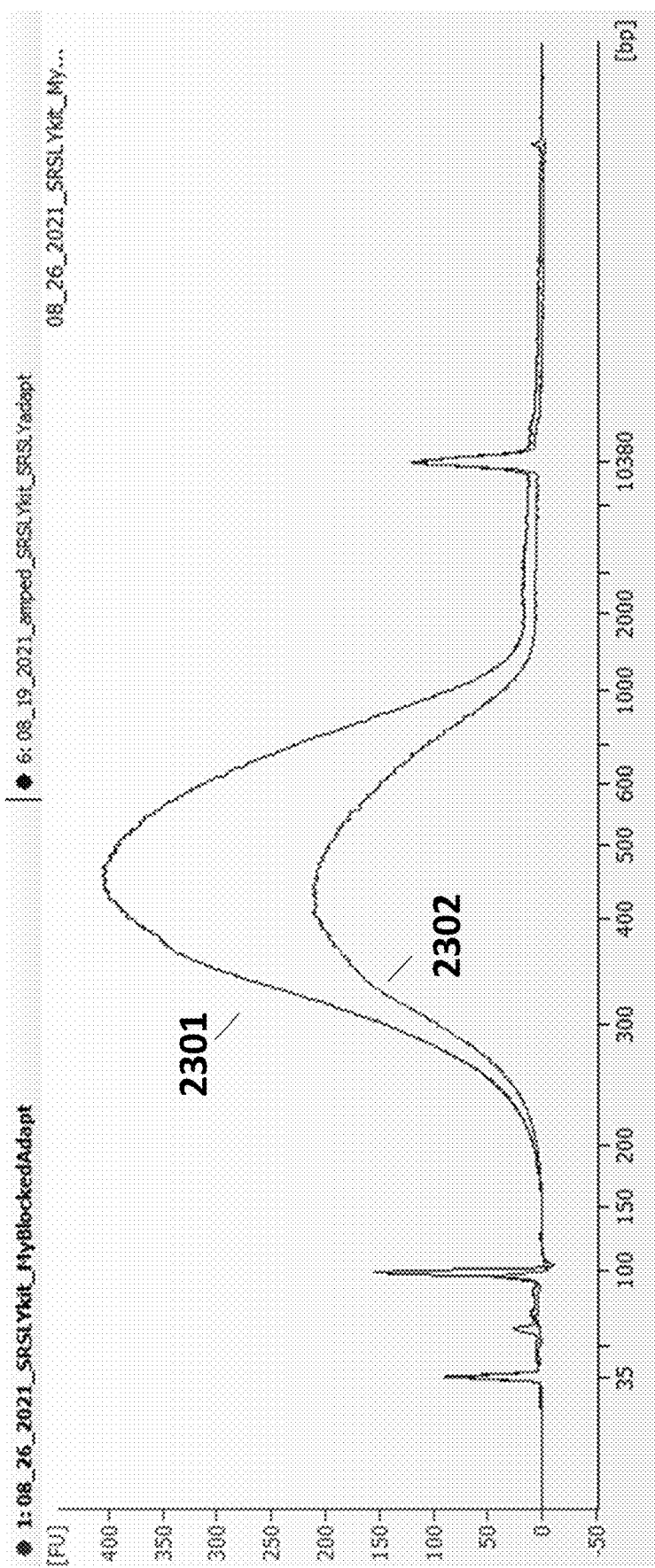
FIG. 23 shows example data resulting from carrying out a splint ligation workflow using different adapter sets.

FIG. 23 shows example data resulting from carrying out a splint ligation workflow, generally described with respect to FIG. 16, using different adapter sets. Line 2302 plots the data for using adapter sets using the adapters described in FIG. 16 (1601, 1502). Line 2301 plots the data for using adapter sets from a Claretbio SRSLY® kit. The two lines only differ by about 2-fold, which corresponds to 1 PCR cycle. This indicates that the adapter sets described in FIG. 16 are compatible with a splint ligation workflow.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

```
                        SEQUENCE LISTING

Sequence total quantity: 85
SEQ ID NO: 1           moltype = DNA  length = 12
FEATURE                Location/Qualifiers
source                 1..12
                       mol_type = other DNA
                       organism = synthetic construct
SEQUENCE: 1
tatggtcgtc ga                                                        12

SEQ ID NO: 2           moltype = DNA  length = 25
FEATURE                Location/Qualifiers
source                 1..25
                       mol_type = other DNA
                       organism = synthetic construct
SEQUENCE: 2
atgcatgcat gatgatgatg catgc                                          25

SEQ ID NO: 3           moltype = DNA  length = 14
FEATURE                Location/Qualifiers
source                 1..14
                       mol_type = other DNA
                       organism = synthetic construct
modified_base          14
                       mod_base = OTHER
                       note = This nucleotide is linked at the 3' end to a
                         nucleotide having an 5' end of CACCTCC and a C3
                         linker/spacer sequence of undefined length
SEQUENCE: 3
acggtttctc catg                                                      14

SEQ ID NO: 4           moltype = DNA  length = 29
FEATURE                Location/Qualifiers
source                 1..29
                       mol_type = other DNA
                       organism = synthetic construct
modified_base          29
                       mod_base = OTHER
                       note = cytosine is linked to adenine in position 1 of SEQ
                         ID NO: 5 via an i5 barcode sequence of undefined length
SEQUENCE: 4
aatgatacgg cgaccaccga gatctacac                                      29

SEQ ID NO: 5           moltype = DNA  length = 33
FEATURE                Location/Qualifiers
source                 1..33
                       mol_type = other DNA
                       organism = synthetic construct
modified_base          1
                       mod_base = OTHER
                       note = adenine is linked to cytosine in position 29 of SEQ
                         ID NO: 4 via an i5 barcode sequence of undefined length
SEQUENCE: 5
acactctttc cctacacgac gctcttccga tct                                 33
```

```
SEQ ID NO: 6              moltype = DNA  length = 34
FEATURE                   Location/Qualifiers
source                    1..34
                          mol_type = other DNA
                          organism = synthetic construct
modified_base             34
                          mod_base = OTHER
                          note = cytosine is linked to adenine in position 1 of SEQ
                           ID NO: 7 via an i7 barcode sequence of undefined length
SEQUENCE: 6
agatcggaag agcacacgtc tgaactccag tcac                                      34

SEQ ID NO: 7              moltype = DNA  length = 24
FEATURE                   Location/Qualifiers
source                    1..24
                          mol_type = other DNA
                          organism = synthetic construct
modified_base             1
                          mod_base = OTHER
                          note = adenine is linked to cytosine in position 34 of SEQ
                           ID NO: 6 via an i7 barcode sequence of undefined length
SEQUENCE: 7
atctcgtatg ccgtcttctg cttg                                                 24

SEQ ID NO: 8              moltype = DNA  length = 33
FEATURE                   Location/Qualifiers
source                    1..33
                          mol_type = other DNA
                          organism = synthetic construct
modified_base             1
                          mod_base = OTHER
                          note = 5' Amino Modifier C12 nucleotide
SEQUENCE: 8
acactctttc cctacacgac gctcttccga tct                                       33

SEQ ID NO: 9              moltype = DNA  length = 40
FEATURE                   Location/Qualifiers
source                    1..40
                          mol_type = other DNA
                          organism = synthetic construct
misc_difference           1
                          note = 5' Amino Modifier C6 adenosine, guanosine, cytidine,
                           or thymidine
misc_difference           2
                          note = a, g, c or t
misc_difference           3
                          note = a, g, c or t
misc_difference           4
                          note = a, g, c or t
misc_difference           5
                          note = a, g, c or t
misc_difference           6
                          note = a, g, c or t
misc_difference           7
                          note = a, g, c or t
SEQUENCE: 9
nnnnnnnaga tcggaagagc gtcgtgtagg gaaagagtgt                                40

SEQ ID NO: 10             moltype = DNA  length = 34
FEATURE                   Location/Qualifiers
source                    1..34
                          mol_type = other DNA
                          organism = synthetic construct
modified_base             1
                          mod_base = OTHER
                          note = 5'-phosphorylated nucleotide
modified_base             34
                          mod_base = OTHER
                          note = 3'Dideoxycytidine
SEQUENCE: 10
agatcggaag agcacacgtc tgaactccag tcac                                      34

SEQ ID NO: 11             moltype = DNA  length = 41
FEATURE                   Location/Qualifiers
source                    1..41
                          mol_type = other DNA
                          organism = synthetic construct
modified_base             1
```

```
                        mod_base = OTHER
                        note = 5' Amino Modifier C12 nucleotide
misc_difference         35
                        note = a, g, c or t
misc_difference         36
                        note = a, g, c or t
misc_difference         37
                        note = a, g, c or t
misc_difference         38
                        note = a, g, c or t
misc_difference         39
                        note = a, g, c or t
misc_difference         40
                        note = a, g, c or t
misc_difference         41
                        note = a, g, c or t
SEQUENCE: 11
gtgactggag ttcagacgtg tgctcttccg atctnnnnnn n                         41

SEQ ID NO: 12           moltype = DNA   length = 29
FEATURE                 Location/Qualifiers
source                  1..29
                        mol_type = other DNA
                        organism = synthetic construct
modified_base           28
                        mod_base = OTHER
                        note = internucleotide phosphorothioate linkage
SEQUENCE: 12
gctttcctct ctatgggcag tcggtgatt                                       29

SEQ ID NO: 13           moltype = DNA   length = 41
FEATURE                 Location/Qualifiers
source                  1..41
                        mol_type = other DNA
                        organism = synthetic construct
modified_base           40
                        mod_base = OTHER
                        note = internucleotide phosphorothioate linkage
SEQUENCE: 13
atctcatccc tgcgtgtctc cgactcagct gaccgaacga t                         41

SEQ ID NO: 14           moltype = DNA   length = 30
FEATURE                 Location/Qualifiers
source                  1..30
                        mol_type = other DNA
                        organism = synthetic construct
modified_base           1
                        mod_base = OTHER
                        note = 5'-phosphorylated nucleotide
modified_base           29
                        mod_base = OTHER
                        note = internucleotide phosphorothioate linkage
SEQUENCE: 14
atcaccgact gcccatagag aggaaagcgg                                      30

SEQ ID NO: 15           moltype = DNA   length = 42
FEATURE                 Location/Qualifiers
source                  1..42
                        mol_type = other DNA
                        organism = synthetic construct
modified_base           1
                        mod_base = OTHER
                        note = 5'-phosphorylated nucleotide
modified_base           41
                        mod_base = OTHER
                        note = internucleotide phosphorothioate linkage
SEQUENCE: 15
tcgttcggtc agctgagtcg gagacacgca gggatgagat gg                        42

SEQ ID NO: 16           moltype = DNA   length = 43
FEATURE                 Location/Qualifiers
source                  1..43
                        mol_type = other DNA
                        organism = synthetic construct
modified_base           1
                        mod_base = OTHER
                        note = 5' Amino Modifier C12 nucleotide
modified_base           42
                        mod_base = OTHER
```

```
                           note = internucleotide phosphorothioate linkage
SEQUENCE: 16
ccatctcatc cctgcgtgtc tccgactcag ctgaccgaac gat                    43

SEQ ID NO: 17              moltype = DNA  length = 50
FEATURE                    Location/Qualifiers
source                     1..50
                           mol_type = other DNA
                           organism = synthetic construct
misc_difference            1
                           note = 5' Amino Modifier C6 adenosine, guanosine, cytidine,
                            or thymidine
misc_difference            2
                           note = a, g, c or t
misc_difference            3
                           note = a, g, c or t
misc_difference            4
                           note = a, g, c or t
misc_difference            5
                           note = a, g, c or t
misc_difference            6
                           note = a, g, c or t
misc_difference            7
                           note = a, g, c or t
modified_base              49
                           mod_base = OTHER
                           note = internucleotide phosphorothioate linkage
SEQUENCE: 17
nnnnnnnatc gttcggtcag ctgagtcgga gacacgcagg gatgagatgg             50

SEQ ID NO: 18              moltype = DNA  length = 31
FEATURE                    Location/Qualifiers
source                     1..31
                           mol_type = other DNA
                           organism = synthetic construct
modified_base              1
                           mod_base = OTHER
                           note = 5'-phosphorylated nucleotide
modified_base              30
                           mod_base = OTHER
                           note = internucleotide phosphorothioate linkage
modified_base              31
                           mod_base = OTHER
                           note = 3'Dideoxycytidine
SEQUENCE: 18
atcaccgact gcccatagag aggaaagcgg c                                 31

SEQ ID NO: 19              moltype = DNA  length = 38
FEATURE                    Location/Qualifiers
source                     1..38
                           mol_type = other DNA
                           organism = synthetic construct
modified_base              1
                           mod_base = OTHER
                           note = 5' Amino Modifier C12 nucleotide
misc_difference            32
                           note = a, g, c or t
misc_difference            33
                           note = a, g, c or t
misc_difference            34
                           note = a, g, c or t
misc_difference            35
                           note = a, g, c or t
misc_difference            36
                           note = a, g, c or t
misc_difference            37
                           note = adenosine, guanosine, cytidine, or thymidine
                            phosphorothioate
misc_difference            38
                           note = a, g, c or t
SEQUENCE: 19
gccgctttcc tctctatggg cagtcggtga tnnnnnnn                          38

SEQ ID NO: 20              moltype = DNA  length = 72
FEATURE                    Location/Qualifiers
source                     1..72
                           mol_type = other DNA
                           organism = synthetic construct
modified_base              1
```

```
                           mod_base = OTHER
                           note = 5'-phosphorylated nucleotide
modified_base              33
                           mod_base = OTHER
                           note = uracil
misc_difference            66
                           note = a, g, c or t
misc_difference            67
                           note = a, g, c or t
misc_difference            68
                           note = a, g, c or t
misc_difference            69
                           note = a, g, c or t
misc_difference            70
                           note = a, g, c or t
misc_difference            71
                           note = adenosine, guanosine, cytidine, or thymidine
                            phosphorothioate
misc_difference            72
                           note = a, g, c or t
SEQUENCE: 20
atcaccgact gcccatagag aggaaagcgg tttttccgct ttcctctcta tgggcagtcg    60
gtgatnnnnn nn                                                        72

SEQ ID NO: 21              moltype = DNA  length = 72
FEATURE                    Location/Qualifiers
source                     1..72
                           mol_type = other DNA
                           organism = synthetic construct
modified_base              1
                           mod_base = OTHER
                           note = 5'-phosphorylated nucleotide
modified_base              33
                           mod_base = OTHER
                           note = uracil
misc_difference            66
                           note = a, g, c or t
misc_difference            67
                           note = a, g, c or t
misc_difference            68
                           note = a, g, c or t
misc_difference            69
                           note = a, g, c or t
misc_difference            70
                           note = a, g, c or t
misc_difference            71
                           note = adenosine, guanosine, cytidine, or thymidine
                            phosphorothioate
misc_difference            72
                           note = a, g, c or t
SEQUENCE: 21
atcaccgact gcccatagag aggaaagcgg tttttccgct ttcctctcta tgggcagtcg    60
gtgatnnnnn nn                                                        72

SEQ ID NO: 22              moltype = DNA  length = 20
FEATURE                    Location/Qualifiers
source                     1..20
                           mol_type = other DNA
                           organism = synthetic construct
SEQUENCE: 22
acacgacgct cttccgatct                                                20

SEQ ID NO: 23              moltype = DNA  length = 27
FEATURE                    Location/Qualifiers
source                     1..27
                           mol_type = other DNA
                           organism = synthetic construct
misc_difference            1
                           note = a, g, c or t
misc_difference            2
                           note = a, g, c or t
misc_difference            3
                           note = a, g, c or t
misc_difference            4
                           note = a, g, c or t
misc_difference            5
                           note = a, g, c or t
misc_difference            6
                           note = a, g, c or t
```

```
misc_difference        7
                       note = a, g, c or t
SEQUENCE: 23
nnnnnnnaga tcggaagagc gtcgtgt                                              27

SEQ ID NO: 24          moltype = DNA  length = 20
FEATURE                Location/Qualifiers
source                 1..20
                       mol_type = other DNA
                       organism = synthetic construct
modified_base          1
                       mod_base = OTHER
                       note = 5'-phosphorylated nucleotide
SEQUENCE: 24
agatcggaag agcacacgtc                                                      20

SEQ ID NO: 25          moltype = DNA  length = 27
FEATURE                Location/Qualifiers
source                 1..27
                       mol_type = other DNA
                       organism = synthetic construct
misc_difference        21
                       note = a, g, c or t
misc_difference        22
                       note = a, g, c or t
misc_difference        23
                       note = a, g, c or t
misc_difference        24
                       note = a, g, c or t
misc_difference        25
                       note = a, g, c or t
misc_difference        26
                       note = a, g, c or t
misc_difference        27
                       note = a, g, c or t
SEQUENCE: 25
gacgtgtgct cttccgatct nnnnnnn                                              27

SEQ ID NO: 26          moltype = DNA  length = 46
FEATURE                Location/Qualifiers
source                 1..46
                       mol_type = other DNA
                       organism = synthetic construct
modified_base          45
                       mod_base = OTHER
                       note = internucleotide phosphorothioate linkage
SEQUENCE: 26
ctgtgtgcct tggcagtctc agctcagacg tgtgctcttc cgatct                         46

SEQ ID NO: 27          moltype = DNA  length = 69
FEATURE                Location/Qualifiers
source                 1..69
                       mol_type = other DNA
                       organism = synthetic construct
modified_base          1
                       mod_base = OTHER
                       note = Biotin nucleotide
modified_base          4
                       mod_base = OTHER
                       note = uracil
modified_base          17
                       mod_base = OTHER
                       note = uracil
modified_base          68
                       mod_base = OTHER
                       note = internucleotide phosphorothioate linkage
SEQUENCE: 27
ccatctcatc cctgcgtgtc tccgactgca ctgccgagca gcatgatcta cacgacgctc          60
ttccgatct                                                                  69

SEQ ID NO: 28          moltype = DNA  length = 24
FEATURE                Location/Qualifiers
source                 1..24
                       mol_type = other DNA
                       organism = synthetic construct
modified_base          1
                       mod_base = OTHER
                       note = 5'-phosphorylated nucleotide
modified_base          24
```

```
                        mod_base = OTHER
                        note = hydroxy nucleotide
SEQUENCE: 28
aatcaccgac tgcccataga gagc                                            24

SEQ ID NO: 29           moltype = DNA  length = 30
FEATURE                 Location/Qualifiers
source                  1..30
                        mol_type = other DNA
                        organism = synthetic construct
misc_difference         25
                        note = a, g, c or t
misc_difference         26
                        note = a, g, c or t
misc_difference         27
                        note = a, g, c or t
misc_difference         28
                        note = a, g, c or t
misc_difference         29
                        note = a, g, c or t
misc_difference         30
                        note = adenosine, guanosine, cytidine, or thymidine amine
SEQUENCE: 29
gctctctatg ggcagtcggt gattnnnnnn                                      30

SEQ ID NO: 30           moltype = DNA  length = 19
FEATURE                 Location/Qualifiers
source                  1..19
                        mol_type = other DNA
                        organism = synthetic construct
modified_base           19
                        mod_base = OTHER
                        note = cytosine is linked to GAT via a barcode sequence of
                         undefined length
SEQUENCE: 30
tgcgtgtctc cgactgcac                                                  19

SEQ ID NO: 31           moltype = DNA  length = 19
FEATURE                 Location/Qualifiers
source                  1..19
                        mol_type = other DNA
                        organism = synthetic construct
modified_base           1
                        mod_base = OTHER
                        note = guanine is linked to NNNNNNATC via a barcode
                         sequence of undefined length
modified_base           19
                        mod_base = OTHER
                        note = hydroxy nucleotide
SEQUENCE: 31
gtgcagtcgg agacacgca                                                  19

SEQ ID NO: 32           moltype = DNA  length = 32
FEATURE                 Location/Qualifiers
source                  1..32
                        mol_type = other DNA
                        organism = synthetic construct
modified_base           1
                        mod_base = OTHER
                        note = Biotin uridine
modified_base           5
                        mod_base = OTHER
                        note = uracil
modified_base           10
                        mod_base = OTHER
                        note = uracil
modified_base           32
                        mod_base = OTHER
                        note = hydroxy nucleotide
SEQUENCE: 32
tccatctcat ccctgcgtgt ctccgactgc ac                                   32

SEQ ID NO: 33           moltype = DNA  length = 47
FEATURE                 Location/Qualifiers
source                  1..47
                        mol_type = other DNA
                        organism = synthetic construct
modified_base           47
                        mod_base = OTHER
```

```
                              note = hydroxy nucleotide
SEQUENCE: 33
ccctgtgtgc cttggcagtc tcagctctct atgggcagtc ggtgatt             47

SEQ ID NO: 34         moltype = DNA   length = 32
FEATURE               Location/Qualifiers
source                1..32
                      mol_type = other DNA
                      organism = synthetic construct
modified_base         1
                      mod_base = OTHER
                      note = Biotin uridine
modified_base         5
                      mod_base = OTHER
                      note = uracil
modified_base         10
                      mod_base = OTHER
                      note = uracil
modified_base         32
                      mod_base = OTHER
                      note = cytosine is linked to GAT via a BC barcode sequence
                       of undefined length which is linked via position 1 of SEQ
                       ID NO: 35 via an INSERT barcode sequence of undefined
                       length
SEQUENCE: 34
tccatctcat ccctgcgtgt ctccgactgc ac                             32

SEQ ID NO: 35         moltype = DNA   length = 47
FEATURE               Location/Qualifiers
source                1..47
                      mol_type = other DNA
                      organism = synthetic construct
modified_base         1
                      mod_base = OTHER
                      note = adenine is linked to GAT via an INSERT barcode
                       sequence of undefined length which is linked via position
                       32 of SEQ ID NO: 34 via a BC barcode sequence of undefined
                       length
SEQUENCE: 35
aatcaccgac tgcccataga gagctgagac tgccaaggca cacaggg             47

SEQ ID NO: 36         moltype = DNA   length = 32
FEATURE               Location/Qualifiers
source                1..32
                      mol_type = other DNA
                      organism = synthetic construct
modified_base         1
                      mod_base = OTHER
                      note = guanine is linked to ATC via a BC barcode sequence
                       of undefined length which is linked via position 47 of SEQ
                       ID NO: 37 via an INSERT barcode sequence of undefined
                       length
modified_base         32
                      mod_base = OTHER
                      note = hydroxy nucleotide
SEQUENCE: 36
gtgcagtcgg agacacgcag ggatgagatg ga                             32

SEQ ID NO: 37         moltype = DNA   length = 47
FEATURE               Location/Qualifiers
source                1..47
                      mol_type = other DNA
                      organism = synthetic construct
modified_base         47
                      mod_base = OTHER
                      note = adenine is linked to ATC via an INSERT barcode
                       sequence of undefined length which is linked via position
                       1 of SEQ ID NO: 35 via a BC barcode sequence of undefined
                       length
SEQUENCE: 37
ccctgtgtgc cttggcagtc tcagctctct atgggcagtc ggtgatt             47

SEQ ID NO: 38         moltype = DNA   length = 29
FEATURE               Location/Qualifiers
source                1..29
                      mol_type = other DNA
                      organism = synthetic construct
modified_base         29
                      mod_base = OTHER
```

```
                        note = cytosine is linked to GAT via a BC barcode sequence
                           of undefined length which is linked via position 1 of SEQ
                           ID NO: 39 via an INSERT barcode sequence of undefined
                           length
SEQUENCE: 38
atctcatccc tgcgtgtctc cgactgcac                                              29

SEQ ID NO: 39           moltype = DNA  length = 46
FEATURE                 Location/Qualifiers
source                  1..46
                        mol_type = other DNA
                        organism = synthetic construct
modified_base           1
                        mod_base = OTHER
                        note = adenine is linked to GAT via an INSERT barcode
                           sequence of undefined length which is linked via position
                           29 of SEQ ID NO: 38 via a BC barcode sequence of undefined
                           length
modified_base           46
                        mod_base = OTHER
                        note = 3' Hexanediol nucleotide
SEQUENCE: 39
aatcaccgac tgcccataga gagctgagac tgccaaggca cacagg                           46

SEQ ID NO: 40           moltype = DNA  length = 31
FEATURE                 Location/Qualifiers
source                  1..31
                        mol_type = other DNA
                        organism = synthetic construct
modified_base           1
                        mod_base = OTHER
                        note = guanine is linked to ATC via a BC barcode sequence
                           of undefined length which is linked via position 23 of SEQ
                           ID NO: 41 via an INSERT barcode sequence of undefined
                           length
SEQUENCE: 40
gtgcagtcgg agacacgcag ggatgagatg g                                           31

SEQ ID NO: 41           moltype = DNA  length = 23
FEATURE                 Location/Qualifiers
source                  1..23
                        mol_type = other DNA
                        organism = synthetic construct
modified_base           23
                        mod_base = OTHER
                        note = thymine is linked to ATC via an INSERT barcode
                           sequence of undefined length which is linked via position
                           1 of SEQ ID NO: 40 via a BC barcode sequence of undefined
                           length
SEQUENCE: 41
ctctctatgg gcagtcggtg att                                                    23

SEQ ID NO: 42           moltype = DNA  length = 38
FEATURE                 Location/Qualifiers
source                  1..38
                        mol_type = other DNA
                        organism = synthetic construct
SEQUENCE: 42
ccctgtgtgc cttggcagtc tcagctctct atgggcag                                    38

SEQ ID NO: 43           moltype = DNA  length = 27
FEATURE                 Location/Qualifiers
source                  1..27
                        mol_type = other DNA
                        organism = synthetic construct
modified_base           1
                        mod_base = OTHER
                        note = Biotin uridine
modified_base           5
                        mod_base = OTHER
                        note = uracil
modified_base           10
                        mod_base = OTHER
                        note = uracil
SEQUENCE: 43
tccatctcat ccctgcgtgt ctccgac                                                27

SEQ ID NO: 44           moltype = DNA  length = 37
FEATURE                 Location/Qualifiers
```

```
source                    1..37
                          mol_type = other DNA
                          organism = synthetic construct
modified_base             32
                          mod_base = OTHER
                          note = 1',2'-Dideoxyribose nucleotide
SEQUENCE: 44
ggaaggccgc tgacagtttt tctgtcagcg gncttcc                              37

SEQ ID NO: 45             moltype = DNA  length = 80
FEATURE                   Location/Qualifiers
source                    1..80
                          mol_type = other DNA
                          organism = synthetic construct
SEQUENCE: 45
cctatcccct gtgtgccttg gcagtctccc gcctcgctgt cacctgctgc tgatttctct     60
ctctatgggc agtcggtgat                                                 80

SEQ ID NO: 46             moltype = DNA  length = 73
FEATURE                   Location/Qualifiers
source                    1..73
                          mol_type = other DNA
                          organism = synthetic construct
modified_base             28
                          mod_base = OTHER
                          note = uracil
modified_base             39
                          mod_base = OTHER
                          note = uracil
modified_base             58
                          mod_base = OTHER
                          note = uracil
modified_base             72
                          mod_base = OTHER
                          note = internucleotide phosphorothioate linkage
modified_base             73
                          mod_base = OTHER
                          note = 3' Hexanediol nucleotide
SEQUENCE: 46
atcaccgact gcccatagag agagaaatca gcagcaggtg acagcgaggc gggagactgc     60
caaggcacac agg                                                        73

SEQ ID NO: 47             moltype = DNA  length = 30
FEATURE                   Location/Qualifiers
source                    1..30
                          mol_type = other DNA
                          organism = synthetic construct
modified_base             1
                          mod_base = OTHER
                          note = 5'-phosphorylated nucleotide
SEQUENCE: 47
ccgcctcgct gtcacctgct gctgatttct                                      30

SEQ ID NO: 48             moltype = RNA  length = 30
FEATURE                   Location/Qualifiers
source                    1..30
                          mol_type = other RNA
                          organism = synthetic construct
modified_base             1
                          mod_base = OTHER
                          note = 5'-phosphorylated nucleotide
modified_base             29
                          mod_base = OTHER
                          note = internucleotide phosphorothioate linkage
modified_base             30
                          mod_base = OTHER
                          note = 3' Hexanediol nucleotide
SEQUENCE: 48
gcgaggcggg agactgccaa ggcacacagg                                      30

SEQ ID NO: 49             moltype = DNA  length = 98
FEATURE                   Location/Qualifiers
source                    1..98
                          mol_type = other DNA
                          organism = synthetic construct
misc_difference           1
                          note = 5' Amino Modifier C6 adenosine, guanosine, cytidine,
                          or thymidine
misc_difference           2
```

```
                        note = a, g, c or t
misc_difference         3
                        note = a, g, c or t
misc_difference         4
                        note = a, g, c or t
misc_difference         5
                        note = a, g, c or t
misc_difference         6
                        note = a, g, c or t
misc_difference         7
                        note = a, g, c or t
modified_base           53
                        mod_base = OTHER
                        note = uracil
modified_base           97
                        mod_base = OTHER
                        note = internucleotide phosphorothioate linkage
SEQUENCE: 49
nnnnnnnatc gttcggtcag ctgagtcgga gacacgcagg gatgagatgg tttttccatc   60
tcatccctgc gtgtctccga ctcagctgac cgaacgat                            98

SEQ ID NO: 52           moltype = DNA  length = 26
FEATURE                 Location/Qualifiers
source                  1..26
                        mol_type = other DNA
                        organism = synthetic construct
misc_difference         1
                        note = a, g, c or t
misc_difference         2
                        note = a, g, c or t
misc_difference         3
                        note = a, g, c or t
misc_difference         4
                        note = a, g, c or t
misc_difference         5
                        note = a, g, c or t
misc_difference         6
                        note = a, g, c or t
SEQUENCE: 50
nnnnnnagat cggaagagcg tcgtgt                                          26

SEQ ID NO: 51           moltype = DNA  length = 26
FEATURE                 Location/Qualifiers
source                  1..26
                        mol_type = other DNA
                        organism = synthetic construct
misc_difference         21
                        note = a, g, c or t
misc_difference         22
                        note = a, g, c or t
misc_difference         23
                        note = a, g, c or t
misc_difference         24
                        note = a, g, c or t
misc_difference         25
                        note = a, g, c or t
misc_difference         26
                        note = a, g, c or t
SEQUENCE: 51
gacgtgtgct cttccgatct nnnnnn                                          26

SEQ ID NO: 52           moltype = DNA  length = 20
FEATURE                 Location/Qualifiers
source                  1..20
                        mol_type = other DNA
                        organism = synthetic construct
SEQUENCE: 52
agatcggaag agcacacgtc                                                 20

SEQ ID NO: 53           moltype = DNA  length = 26
FEATURE                 Location/Qualifiers
source                  1..26
                        mol_type = other DNA
                        organism = synthetic construct
misc_difference         21
                        note = a, g, c or t
misc_difference         22
                        note = a, g, c or t
misc_difference         23
```

```
                        note = a, g, c or t
misc_difference         24
                        note = a, g, c or t
misc_difference         25
                        note = a, g, c or t
misc_difference         26
                        note = a, g, c or t
SEQUENCE: 53
gacgtgtgct cttccgatct nnnnnn                                                26

SEQ ID NO: 54           moltype = DNA  length = 19
FEATURE                 Location/Qualifiers
source                  1..19
                        mol_type = other DNA
                        organism = synthetic construct
modified_base           19
                        mod_base = OTHER
                        note = cytosine is linked to GAT via a BC barcode sequence
                         of undefined length which is linked to position 1 of SEQ
                         ID NO: 55 via an INSERT barcode sequence of undefined
                         length
SEQUENCE: 54
tgcgtgtctc cgactgcac                                                        19

SEQ ID NO: 55           moltype = DNA  length = 24
FEATURE                 Location/Qualifiers
source                  1..24
                        mol_type = other DNA
                        organism = synthetic construct
modified_base           24
                        mod_base = OTHER
                        note = hydroxy nucleotide
SEQUENCE: 55
aatcaccgac tgcccataga gagc                                                  24

SEQ ID NO: 56           moltype = DNA  length = 32
FEATURE                 Location/Qualifiers
source                  1..32
                        mol_type = other DNA
                        organism = synthetic construct
modified_base           1
                        mod_base = OTHER
                        note = Biotin uridine
modified_base           5
                        mod_base = OTHER
                        note = uracil
modified_base           10
                        mod_base = OTHER
                        note = uracil
SEQUENCE: 56
tccatctcat ccctgcgtgt ctccgactgc ac                                         32

SEQ ID NO: 57           moltype = DNA  length = 32
FEATURE                 Location/Qualifiers
source                  1..32
                        mol_type = other DNA
                        organism = synthetic construct
modified_base           1
                        mod_base = OTHER
                        note = Biotin uridine
modified_base           5
                        mod_base = OTHER
                        note = uracil
modified_base           10
                        mod_base = OTHER
                        note = uracil
modified_base           32
                        mod_base = OTHER
                        note = cytosine is linked to GATXXXXXXXXXXXXXXXXX via a BC
                         barcode sequence of undefined length which is linked to
                         position 1 of SEQ ID NO: 58 via an INSERT barcode sequence
                         of undefined length
SEQUENCE: 57
tccatctcat ccctgcgtgt ctccgactgc ac                                         32

SEQ ID NO: 58           moltype = DNA  length = 47
FEATURE                 Location/Qualifiers
source                  1..47
                        mol_type = other DNA
```

```
                             organism = synthetic construct
modified_base                1
                             mod_base = OTHER
                             note = adenine is linked to GATXXXXXXXXXXXXXXXXXX via an
                              INSERT barcode sequence of undefined length which is
                              linked to position 32 of SEQ ID NO: 57 via BC barcode
                              sequence of undefined length
SEQUENCE: 58
aatcaccgac tgcccataga gagctgagac tgccaaggca cacaggg                         47

SEQ ID NO: 59                moltype = DNA   length = 32
FEATURE                      Location/Qualifiers
source                       1..32
                             mol_type = other DNA
                             organism = synthetic construct
modified_base                1
                             mod_base = OTHER
                             note = guanine is linked to XXXXXXXXXXXXXXXXXXATC via a BC
                              barcode sequence of undefined length which is linked to
                              position 47 of SEQ ID NO: 60 via an INSERT barcode
                              sequence of undefined length
modified_base                32
                             mod_base = OTHER
                             note = hydroxy nucleotide
SEQUENCE: 59
gtgcagtcgg agacacgcag ggatgagatg ga                                         32

SEQ ID NO: 60                moltype = DNA   length = 47
FEATURE                      Location/Qualifiers
source                       1..47
                             mol_type = other DNA
                             organism = synthetic construct
modified_base                47
                             mod_base = OTHER
                             note = thymine is linked to XXXXXXXXXXXXXXXXXXATC via an
                              INSERT barcode sequence of undefined length which is
                              linked to position 1 of SEQ ID NO: 59 via a BC barcode
                              sequence of undefined length
SEQUENCE: 60
ccctgtgtgc cttggcagtc tcagctctct atgggcagtc ggtgatt                         47

SEQ ID NO: 61                moltype = DNA   length = 47
FEATURE                      Location/Qualifiers
source                       1..47
                             mol_type = other DNA
                             organism = synthetic construct
modified_base                1
                             mod_base = OTHER
                             note = 5'-phosphorylated nucleotide
modified_base                47
                             mod_base = OTHER
                             note = hydroxy nucleotide
SEQUENCE: 61
aatcaccgac tgcccataga gagctgagac tgccaaggca cacaggg                         47

SEQ ID NO: 62                moltype = DNA   length = 29
FEATURE                      Location/Qualifiers
source                       1..29
                             mol_type = other DNA
                             organism = synthetic construct
misc_difference              24
                             note = a, g, c or t
misc_difference              25
                             note = a, g, c or t
misc_difference              26
                             note = a, g, c or t
misc_difference              27
                             note = a, g, c or t
misc_difference              28
                             note = a, g, c or t
misc_difference              29
                             note = adenosine, guanosine, cytidine, or thymidine amide
SEQUENCE: 62
ctctctatgg gcagtcggtg attnnnnnn                                             29

SEQ ID NO: 63                moltype = DNA   length = 47
FEATURE                      Location/Qualifiers
source                       1..47
                             mol_type = other DNA
```

```
                            organism = synthetic construct
modified_base               47
                            mod_base = OTHER
                            note = hydroxy nucleotide
SEQUENCE: 63
aatcaccgac tgcccataga gagctgagac tgccaaggca cacaggg            47

SEQ ID NO: 64               moltype = DNA   length = 23
FEATURE                     Location/Qualifiers
source                      1..23
                            mol_type = other DNA
                            organism = synthetic construct
modified_base               23
                            mod_base = OTHER
                            note = hydroxy nucleotide
SEQUENCE: 64
ctctctatgg gcagtcggtg att                                       23

SEQ ID NO: 65               moltype = DNA   length = 47
FEATURE                     Location/Qualifiers
source                      1..47
                            mol_type = other DNA
                            organism = synthetic construct
SEQUENCE: 65
aatcaccgac tgcccataga gagctgagac tgccaaggca cacaggg            47

SEQ ID NO: 66               moltype = DNA   length = 23
FEATURE                     Location/Qualifiers
source                      1..23
                            mol_type = other DNA
                            organism = synthetic construct
modified_base               23
                            mod_base = OTHER
                            note = thymine is linked to an adenine-hydroxy via an
                             INSERT barcode sequence of undefined length
SEQUENCE: 66
ctctctatgg gcagtcggtg att                                       23

SEQ ID NO: 67               moltype = DNA   length = 32
FEATURE                     Location/Qualifiers
source                      1..32
                            mol_type = other DNA
                            organism = synthetic construct
modified_base               1
                            mod_base = OTHER
                            note = Biotin uridine
modified_base               5
                            mod_base = OTHER
                            note = uracil
modified_base               10
                            mod_base = OTHER
                            note = uracil
modified_base               32
                            mod_base = OTHER
                            note = cytosine is linked to GAT via a BC barcode sequence
                             of undefined length
SEQUENCE: 67
tccatctcat ccctgcgtgt ctccgactgc ac                             32

SEQ ID NO: 68               moltype = DNA   length = 32
FEATURE                     Location/Qualifiers
source                      1..32
                            mol_type = other DNA
                            organism = synthetic construct
modified_base               1
                            mod_base = OTHER
                            note = guanine is linked to TC via a BC barcode sequence of
                             undefined length
modified_base               32
                            mod_base = OTHER
                            note = hydroxy nucleotide
SEQUENCE: 68
gtgcagtcgg agacacgcag ggatgagatg ga                             32

SEQ ID NO: 69               moltype = DNA   length = 32
FEATURE                     Location/Qualifiers
source                      1..32
                            mol_type = other DNA
                            organism = synthetic construct
```

```
modified_base           1
                        mod_base = OTHER
                        note = Biotin uridine
modified_base           5
                        mod_base = OTHER
                        note = uracil
modified_base           10
                        mod_base = OTHER
                        note = uracil
modified_base           32
                        mod_base = OTHER
                        note = cytosine is linked to GAT via a BC barcode sequence
                          of undefined length which is linked to position 1 of SEQ
                          ID NO: 70 via an INSERT barcode sequence of undefined
                          length
SEQUENCE: 69
tccatctcat ccctgcgtgt ctccgactgc ac                                           32

SEQ ID NO: 70           moltype = DNA   length = 47
FEATURE                 Location/Qualifiers
source                  1..47
                        mol_type = other DNA
                        organism = synthetic construct
modified_base           1
                        mod_base = OTHER
                        note = adenine is linked to GAT via an INSERT barcode
                          sequence of undefined length which is linked to position
                          32 of SEQ ID NO: 69 via a BC barcode sequence of undefined
                          length
SEQUENCE: 70
aatcaccgac tgcccataga gagctgagac tgccaaggca cacaggg                           47

SEQ ID NO: 71           moltype = DNA   length = 32
FEATURE                 Location/Qualifiers
source                  1..32
                        mol_type = other DNA
                        organism = synthetic construct
modified_base           1
                        mod_base = OTHER
                        note = guanine is linked to ATC via a BC barcode sequence
                          of undefined length which is linked to position 23 of SEQ
                          ID NO: 72 via an INSERT barcode sequence of undefined
                          length
modified_base           32
                        mod_base = OTHER
                        note = hydroxy nucloetide
SEQUENCE: 71
gtgcagtcgg agacacgcag ggatgagatg ga                                           32

SEQ ID NO: 72           moltype = DNA   length = 23
FEATURE                 Location/Qualifiers
source                  1..23
                        mol_type = other DNA
                        organism = synthetic construct
modified_base           23
                        mod_base = OTHER
                        note = thymine is linked to ATC via an INSERT barcode
                          sequence of undefined length which is linked to position 1
                          of SEQ ID NO: 71 via a BC barcode sequence of undefined
                          length
SEQUENCE: 72
ctctctatgg gcagtcggtg att                                                     23

SEQ ID NO: 73           moltype = DNA   length = 31
FEATURE                 Location/Qualifiers
source                  1..31
                        mol_type = other DNA
                        organism = synthetic construct
modified_base           1
                        mod_base = OTHER
                        note = guanine is linked to ATC via a BC barcode sequence
                          of undefined length which is linked to position 23 of SEQ
                          ID NO: 74 via an INSERT barcode sequence of undefined
                          length
SEQUENCE: 73
gtgcagtcgg agacacgcag ggatgagatg g                                            31

SEQ ID NO: 74           moltype = DNA   length = 23
FEATURE                 Location/Qualifiers
```

```
source              1..23
                    mol_type = other DNA
                    organism = synthetic construct
modified_base       23
                    mod_base = OTHER
                    note = thymine is linked to ATC via an INSERT barcode
                     sequence of undefined length which is linked to position 1
                     of SEQ ID NO: 73 via a BC barcode sequence of undefined
                     length
SEQUENCE: 74
ctctctatgg gcagtcggtg att                                                23

SEQ ID NO: 75       moltype = DNA  length = 22
FEATURE             Location/Qualifiers
source              1..22
                    mol_type = other DNA
                    organism = synthetic construct
SEQUENCE: 75
ctctctatgg gcagtcggtg at                                                 22

SEQ ID NO: 76       moltype = DNA  length = 29
FEATURE             Location/Qualifiers
source              1..29
                    mol_type = other DNA
                    organism = synthetic construct
modified_base       1
                    mod_base = OTHER
                    note = guanine is linked to ATC via a BC barcode sequence
                     of undefined length
modified_base       24
                    mod_base = OTHER
                    note = uracil
modified_base       29
                    mod_base = OTHER
                    note = uridine biotin
SEQUENCE: 76
gtgcagtcgg agacacgcag ggatgagat                                          29

SEQ ID NO: 77       moltype = DNA  length = 51
FEATURE             Location/Qualifiers
source              1..51
                    mol_type = other DNA
                    organism = synthetic construct
misc_difference     1
                    note = a, g, c or t
misc_difference     2
                    note = a, g, c or t
misc_difference     3
                    note = a, g, c or t
misc_difference     4
                    note = a, g, c or t
misc_difference     5
                    note = a, g, c or t
misc_difference     6
                    note = a, g, c or t
modified_base       51
                    mod_base = OTHER
                    note = 3' Hexanediol nucleotide
SEQUENCE: 77
nnnnnnatca ccgactgccc atagagagct gagactgcca aggcacacag g                 51

SEQ ID NO: 78       moltype = DNA  length = 21
FEATURE             Location/Qualifiers
source              1..21
                    mol_type = other DNA
                    organism = synthetic construct
modified_base       21
                    mod_base = OTHER
                    note = cytosine is linked to GATNNNNNN via a BC barcode
                     sequence of undefined length
SEQUENCE: 78
cctgcgtgtc tccgactgca c                                                  21

SEQ ID NO: 79       moltype = DNA  length = 45
FEATURE             Location/Qualifiers
source              1..45
                    mol_type = other DNA
                    organism = synthetic construct
SEQUENCE: 79
```

```
atcaccgact gcccatagag agctgagact gccaaggcac acagg            45

SEQ ID NO: 80           moltype = DNA  length = 28
FEATURE                 Location/Qualifiers
source                  1..28
                        mol_type = other DNA
                        organism = synthetic construct
misc_difference         23
                        note = a, g, c or t
misc_difference         24
                        note = a, g, c or t
misc_difference         25
                        note = a, g, c or t
misc_difference         26
                        note = a, g, c or t
misc_difference         27
                        note = a, g, c or t
misc_difference         28
                        note = a, g, c or t
SEQUENCE: 80
ctctctatgg gcagtcggtg atnnnnnn                                28

SEQ ID NO: 81           moltype = DNA  length = 32
FEATURE                 Location/Qualifiers
source                  1..32
                        mol_type = other DNA
                        organism = synthetic construct
modified_base           1
                        mod_base = OTHER
                        note = Biotin uridine
modified_base           5
                        mod_base = OTHER
                        note = uracil
modified_base           10
                        mod_base = OTHER
                        note = uracil
modified_base           32
                        mod_base = OTHER
                        note = cytosine is linked to GAT via a BC barcode sequence
                         of undefined length
SEQUENCE: 81
tccatctcat ccctgcgtgt ctccgactgc ac                           32

SEQ ID NO: 82           moltype = DNA  length = 32
FEATURE                 Location/Qualifiers
source                  1..32
                        mol_type = other DNA
                        organism = synthetic construct
modified_base           1
                        mod_base = OTHER
                        note = guanine is linked to TC via a BC barcode sequence of
                         undefined length
SEQUENCE: 82
gtgcagtcgg agacacgcag ggatgagatg ga                           32

SEQ ID NO: 83           moltype = DNA  length = 20
FEATURE                 Location/Qualifiers
source                  1..20
                        mol_type = other DNA
                        organism = synthetic construct
SEQUENCE: 83
tacgtacgta cgtacgtacg                                         20

SEQ ID NO: 84           moltype = DNA  length = 30
FEATURE                 Location/Qualifiers
source                  1..30
                        mol_type = other DNA
                        organism = synthetic construct
misc_difference         25
                        note = a, g, c or t
misc_difference         26
                        note = a, g, c or t
misc_difference         27
                        note = a, g, c or t
misc_difference         28
                        note = a, g, c or t
misc_difference         29
                        note = a, g, c or t
misc_difference         30
```

```
                        note = adenosine, guanosine, cytidine, or thymidine amide
SEQUENCE: 84
gctctctatg ggcagtcggt gattnnnnnn                                            30

SEQ ID NO: 85           moltype = DNA  length = 24
FEATURE                 Location/Qualifiers
source                  1..24
                        mol_type = other DNA
                        organism = synthetic construct
modified_base           1
                        mod_base = OTHER
                        note = adenine is linked to GAT via an INSERT barcode
                          sequence of undefined length which is linked to position
                          19 of SEQ ID NO: 54 via a BC barcode sequence of undefined
                          length
modified_base           24
                        mod_base = OTHER
                        note = hydroxy nucleotide
SEQUENCE: 85
aatcaccgac tgcccataga gagc                                                  24
```

What is claimed is:

1. A method for sequencing error correction by preserving sequences of both strands of a nucleic acid molecule during amplification, comprising:
   (a) providing a double-stranded nucleic acid molecule attached to a support, wherein the support comprises a plurality of surface primers, wherein the double-stranded nucleic acid molecule comprises a first strand and a second strand at least partially hybridized to the first strand, the first strand attached to a first surface primer of the plurality of surface primers;
   (b) detaching the second strand, or derivative thereof, from the first strand and annealing the second strand, or the derivative thereof, to a second surface primer of the plurality of surface primers; and
   (c) extending the second surface primer using the second strand, or the derivative thereof, as a template, to generate an extended second surface primer comprising a reverse complement copy of the second strand, or the derivative thereof, thereby generating an amplified support comprising the support attached to both (1) the first strand and (2) the extended second surface primer comprising the reverse complement copy of the second strand, or the derivative thereof.

2. The method of claim 1, wherein the second strand comprises a cleavage site adjacent to a 3' end, and wherein the derivative of the second strand is generated by (i) cleaving at the cleavage site to produce a 3'-hydroxyl terminus at the second strand, and (ii) extending the second strand from the 3'-hydroxyl terminus using the first strand as a template, to generate an extended second strand.

3. The method of claim 2, wherein the cleavage site: (1) comprises a uracil residue and the cleaving comprises using Uracil-DNA glycosylase (UDG) and Apurinic/apyrimidinic Endonuclease 1 (APE1) enzymes, or (2) comprises a ribonucleotide and the cleaving comprises using ribonuclease HII (Rnase HII) and the APE1 enzymes.

4. The method of claim 1, further comprising, subsequent to detaching the second strand, or the derivative thereof, from the first strand in (b), (i) annealing a primer to the first strand, (ii) extending the primer using the first strand as a template, to generate an extended primer comprising a reverse complement copy of the first strand, (iii) detaching the extended primer from the first strand and annealing the extended primer to a third surface primer of the plurality of surface primers, and (iv) extending the third surface primer to generate an extended third surface primer comprising a copy of the first strand.

5. The method of claim 1, wherein the extending in (c) is performed in a partition.

6. The method of claim 5, wherein the partition is a droplet in an emulsion or a well.

7. The method of claim 1, wherein the extending in (c) is performed in a bulk solution.

8. The method of claim 1, further comprising performing one or more additional extension reactions to generate the amplified support, wherein the amplified support comprises the support attached to a plurality of nucleic acid molecules comprising both (1) a plurality of copies of at least a portion of the first strand and (2) a plurality of reverse complement copies of at least a portion of the second strand.

9. The method of claim 8, wherein the ratio of the plurality of copies of the first strand in the plurality of nucleic acid molecules on the amplified support is between about 0.4 and 0.6.

10. The method of claim 8, further comprising sequencing the plurality of nucleic acid molecules attached to the amplified support to generate a sequencing dataset.

11. The method of claim 10, wherein the sequencing comprises flow-based sequencing comprising a plurality of flow steps, wherein each nucleic acid molecule of the plurality of nucleic acid molecules is annealed to a sequencing primer and the sequencing primer is extended stepwise with distinct flow steps of the plurality of flow steps, wherein a distinct flow step comprises flowing in nucleotides of a single base and detecting sequencing signals, or lack thereof, that are indicative of incorporation of the nucleotides or lack thereof.

12. The method of claim 10, wherein the double-stranded nucleic acid molecule comprises an artificial base mismatch error that is not present in a native template nucleic acid molecule that the double-stranded nucleic acid molecule derives from, and further comprising identifying the artificial base mismatch error from the sequencing dataset.

13. The method of claim 12, wherein the artificial base mismatch error is artificially introduced in the double-stranded nucleic acid molecule by a deamination reaction.

14. The method of claim 12, wherein a locus of the artificial base mismatch error is identified as an error single nucleotide polymorphism (SNP), wherein error SNPs are filtered from true SNPs.

15. The method of claim 12, further comprising trimming a sequencing read from the sequencing dataset by identifying a phasing event derived from the artificial base mismatch error.

16. The method of claim 15, wherein the phasing event comprises a difference in analog signals obtained from the plurality of copies of the at least the portion of the first strand and analog signals obtained from the plurality of reverse complement copies of the at least the portion of the second strand, or the derivative thereof.

17. The method of claim 10, wherein the plurality of nucleic acid molecules attached to the amplified support is sequenced while the amplified support is immobilized to a substrate.

18. The method of claim 1, further comprising:
(d) providing an amplified cluster of a plurality of nucleic acid molecules attached to the amplified support, wherein the plurality of nucleic acid molecules is derived from the double-stranded nucleic acid molecule, wherein a first subset of the plurality of nucleic acid molecules each comprises a copy of at least a portion of the first strand and a second subset of the plurality of nucleic acid molecules each comprises a copy of at least a portion of the reverse complement copy of the second strand, and wherein the double-stranded nucleic acid molecule comprises an artificial base mismatch error that is not present in a native template nucleic acid molecule that the double-stranded nucleic acid molecule derives from;
(e) sequencing the plurality of nucleic acid molecules in the amplified cluster by collecting a plurality of sequencing signals from a location of the amplified cluster; and
(f) generating a sequencing read for the double-stranded nucleic acid molecule from the plurality of sequencing signals, wherein the sequencing read does not include a base call at a locus of the artificial base mismatch error based on identifying a phasing event from the plurality of sequencing signals.

19. The method of claim 1, further comprising:
(d) obtaining a plurality of sequencing signals corresponding to a plurality of nucleic acid molecules derived from the double-stranded nucleic acid molecule attached to the support, performing a plurality of sequential sequencing flow steps on the amplified support comprising the plurality of nucleic acid molecules covalently bound thereto, wherein a first subset of the plurality of nucleic acid molecules each comprises a copy of at least a portion of the first strand and a second subset of the plurality of nucleic acid molecules each comprises a copy of at least a portion of the reverse complement copy of the second strand;
(e) determining presence of phasing at a particular sequencing flow step of the plurality of sequential sequencing flow steps;
(f) ignoring or removing sequencing signals collected at that particular sequencing flow step and downstream of the particular sequencing flow step from base calling; and
(g) generating a sequencing read from non-removed sequencing signals of the plurality of sequencing signals.

20. The method of claim 19, further comprising identifying a base mismatch error at the particular sequencing flow step.

* * * * *